United States Patent
Enders et al.

(10) Patent No.: US 9,157,124 B2
(45) Date of Patent: Oct. 13, 2015

(54) SYSTEMS AND METHODS FOR DIAGNOSING A PREDISPOSITION TO DEVELOP COLON CANCER

(71) Applicant: Institute for Cancer Research, Philadelphia, PA (US)

(72) Inventors: Greg H. Enders, Villanova, PA (US); Mark Andrake, Huntingdon Valley, PA (US); Michael J. Hall, Glenside, PA (US); Biao Luo, Princeton, NJ (US); Timothy J. Yen, Haverford, PA (US)

(73) Assignee: Institute for Cancer Research, Philadelphia, PA (US)

( * ) Notice: Subject to any disclaimer, the term of this patent is extended or adjusted under 35 U.S.C. 154(b) by 38 days.

(21) Appl. No.: 13/833,946

(22) Filed: Mar. 15, 2013

(65) Prior Publication Data
US 2014/0080124 A1 Mar. 20, 2014

Related U.S. Application Data

(60) Provisional application No. 61/702,423, filed on Sep. 18, 2012, provisional application No. 61/731,506, filed on Nov. 30, 2012.

(51) Int. Cl.
| | | |
|---|---|---|
| *G01N 33/48* | (2006.01) | |
| *C12Q 1/68* | (2006.01) | |
| *G01N 33/574* | (2006.01) | |
| *G06F 19/10* | (2011.01) | |

(52) U.S. Cl.
CPC ........ *C12Q 1/6886* (2013.01); *G01N 33/57446* (2013.01); *C12Q 2600/156* (2013.01); *G06F 19/10* (2013.01)

(58) Field of Classification Search
CPC ...................................................... G06F 19/10
USPC .......................................................... 702/19
See application file for complete search history.

(56) References Cited

U.S. PATENT DOCUMENTS

| | | |
|---|---|---|
| 2008/0253632 A1 | 10/2008 | Halazonetis |
| 2012/0021935 A1 | 1/2012 | Cazaux et al. |
| 2012/0220645 A1 | 8/2012 | Gollin et al. |

FOREIGN PATENT DOCUMENTS

WO 2012109500 8/2012

OTHER PUBLICATIONS

Wood., L., et al., "The Genomic Landscapes of Human Breast and Colorectal Cancers", Science, vol. 318, Nov. 16, 2007, pp. 1108-1113.
Kucherlapati, et al., "Comprehensive Molecular Characterization of Human Colon and Rectal Cancer", Nature, 2012, 487(7407), pp. 330-337.
Cimino, et al., "Aneuploidy in mammalian somatic cells in vivo", Mutation Research, 167 (1986), pp. 107-122.
Oka, et al., "DNA damage signaling is activated during cancer progression in human colorectal carcinoma", Cancer Biol. Ther., 2010, 9(3):246-52.
Ivashkevich, et al., "gammaH2AX foci as a measure of DNA damage: a computational approach to automatic analysis", Mutat. Res. ePub, Jan. 7, 2011, 711 (1-2):49-60.
Sedelnikova, et al., "y-H2AX in Cancer Cells: A potential biomarker for cancer diagnostics, prediction and recurrence" Cell Cycle, 2006, 5(24): 2909-2913.
Redon, et al., "Histone gammaH2AX and poly(ADP-ribose) as clinical pharmacodynamic biomarkers", Clin. Cancer Res., 2010, 16(18):4532-4542.
Novotna, et al., "Role of [gamma]-H2AX in DNA-Damage Response and its Possible Clinical Applications", Mil. Med. Sci. Lett. (Voj. Zdrav. Listy), 2011, 80(4):169-177.
Venook, et al., "Is there currently an established role for the use of predictive or prognostic molecular markers in the management of colorectal cancer? A point/counterpoint." Apr. 20, 2010, pp. 193-200.
Kennedy, et al., "Development and independent validation of a prognostic assay for stage II colon cancer using formalin-fixed paraffin-embedded tissue", J. Clin. Oncol., 2011, 29(35):4620-6.
Salazar, et al., "Gene expression signature to improve prognosis prediction of stage II and III colorectal cancer", J. Clin. Oncol., 2011, 29:17-24.
Agesenm et al., "ColoGuideEx: a robust gene classifier specific for stage II colorectal cancer prognosis", Gut Epub Jan. 2, 2010, 61(11):1560-7.
Tan, et al., "Genetics: an 18-gene signauture (ColoPrint) for colon cancer prognosis", Nat. Rev. Clin. Oncol., 2011, 8:131-133.
Muslimovic, et al., Measurement of H2AX Phosphorylation as a Marker of Ionizing Radiation Induced Cell Damage, Jul. 3, 2012, pp. 3-21.
Cai, et al., "Computational analysis of the number, area and density of gamma-H2AX foci in breast cancer cells exposed to (111)In-DTPA-hEGF or gamma-rays using Image-J software", Int. J. Radiat. Biol., 2009, 85(3):262-71.
Zlobinskaya, et al., "Induction and repair of DNA double-strand breaks assessed by y-H2AX foci after irradiation with pulsed or continuous proton beams", Radiat. Environ. Biophys., Epub Jan. 7, 2012, 51(1):23-32.

(Continued)

*Primary Examiner* — Jerry Lin
(74) *Attorney, Agent, or Firm* — Stradley Ronon Stevens & Young, LLP

(57) ABSTRACT

Systems and methods for diagnosing or characterizing a predisposition to colon cancer are provided. Cell nuclei may be evaluated for the presence or quantity of gamma-H2AX foci. Nucleic acids may be evaluated for the presence, type, or quantity of genomic instability or surrogates of dsDNA breaks such as ataxia telangiectasia mutated (ATM), Rad3-related protein (ATR), and Tumor suppressor p53-binding protein 1 (53BP1) in gamma-H2AX foci. Nucleic acids comprising a germline nucleic acid sequence of the ERCC6, WRN, TERT, and FAAP100 genes may be sequenced or probed to determine if the nucleic acid sequence includes one or more alterations that cause genomic instability, dsDNA breaks, or gamma-H2AX foci or otherwise predispose a subject to develop colon cancer.

8 Claims, 7 Drawing Sheets

(56) References Cited

OTHER PUBLICATIONS

Runge, et al., "Fully automated interpretation of ionizing radiation-induced [gamma]H2AX foci by the novel pattern recognition system AKLIDES," Int. J. Radiat. Biol., Epub Mar. 26, 2012, 88(5):439-447. Abstract only.

Risques, et al., "Ulcerative colitis is a disease of accelerated colon aging: evidence from telomere attrition and DNA damage", Gastroenterology, 2008, 135(2):410-8.

Cattaneo, et al., "Pathways and Crossroads to Colorectal Cancer," Pre-Invasive Disease: Pathogenesis and Clinical Management, 2011, pp. 369-394.

Takabayashi, et al., "Alteration of the DNA damage response in colorectal tumor progression", Human Pathology, Jun. 2013, 44(6):1038-1046.

International Search Report and Written Opinion dated Feb. 21, 2014 issued in PCT/US13/60264.

```
                          ↓
   50408761   50408771   50408781   50408791
ATTCTGAATCACC*TTATTATACTTCTGTCGTTTTACAGA
.............    ....W......................
.............*..........................
,,,,,,,,,,,,,*,,,,a,,,,,,,,,,,,,,,,,,,,,
.............*..........................
.............*..........................
.............*....A.....................
,,,,,,,,,,,,,*,,,,,,,,,,,,,,,,,,,,,,,,,,
,,,,,,,,,,,,,*,,,,a,,,,,,,,,,,,,,,,,,,,,
.............*....A.....................
.............*..........................
,,,,,,,,,,,,,*,,,,,,g,,,,,,,,,,,,,,,,,,,
.............*..........................
.............*...C......................
,,,,,,,,,,,,,*,,,,a,,,,,,,,,,,,,,,,,,,,,
.............*..........................
.............*..........................
,,,,,,,,,,,,,*,,,,a,,,,,,,,,,,,,,,,,,,,,
             *
```

FIG. 3

MPNEGIPHSSQTQEQDCLQSQPVSNNEEMAIKQESGGDGE
VEEY

LSFRSVGDGLSTSAVGCASAAPRRGPALLHIDRHQIQAVEPSA
QALELQGLGVDVYDQ

DVLEQGVLQQVDNAIHEASRASQLVDVEKEYRSVLDDLTSCT
TSLRQINKIIEQLSPQ

↓
AATSRDINRKLDSVKRQKYNKEQQLKKITAKQKHLQAILGGA
EVKIELDHASLEEDAE

PGPSSLGSMLMPVQETAWEELIRTGQMTPFG**TQIPQKQEKK
PRKIMLNEASGFEKYLA

DQAKLSFERKKQGCNKRAARKAPAPVTPPAPVQNKNKPNKK
ARVLSKKEERLKKHIKK

LQKRALQFQGKVGLPKARRPWESDMRPEAEGDSEGEESEYF
PTEEEEEEDDEVGAE     (SEQ ID NO:4)

FIG. 4

```
                            ↓
31088681   31088691   31088701   310887
CGTTGCACTTACTGCTACTGCAAGTTCTTCAATCCG
....................Y...............
....................T...............
....................................
....................T...............
....................................
,,,,,,,,,,,,,,,,,,,,t,,,,,,,,,,,,,,,,
....................T...............
 ...................T...............
....................................
...  ...............T...............
...  ...............................
.....  ..............T...............
........  ...........................
.........  .........T...............
..........  ........T...............
```

FIG. 5

```
                                    ↓
                       31134461  31134471  31134481  31134491
                       TGACAATTGGCATGCACTTATCCCAAGC*GGTGAAAGCTGG
                       .....................M......  ..........
                       ............................*...........
                       ,,,,,,,,,,,,,,,,,,,,,a,,,,,,*,,,,,,,,,,,
                       ............................*...........
                       ,,,,,,,,,,,,,,,,,,,,,,,,,,,,*,,,,,,,,,,,
                       ............................*...........
                       ,,,,,,,,,,,,,,,,,,,,,a,,,,,,*,,,,,,,,,,,
                       .....................A......*...........
                        ....................A......*...........
                       ,,,,,,,,,,,,,,,,,,,,,a,,,,,,*,,,,,,,,,,,
                       ,,,,,,,,,,,,,,,,,,,,,,,,,,,,*,,,,,,,,,,,
                       .  ...................A......*...........
                       .  ,,,,,,,,,,,,,,,,,,,,,a,,,,,,*,,,,,,,,,,,
                       ,  ,,,,,,,,,,,,,,,,,,,,,,,,,,,,*,,,,,,,,,,,
                       ...  .................A......*...........
                       .... ,,,,,,,,,,,,,,,,,,,,,,,,,,*,,,,,,,,,,,
                       .... ,,,,,,,,,,,,,,,,,,a,,,,,,*,,,,,,,,,,,
                       ..... ,,,,,,,,,,,,,,,,,a,,,,,,*,,,,,,,,,,,
                       ....... .....................*...........
```

SYSTEMS AND METHODS FOR DIAGNOSING A PREDISPOSITION TO DEVELOP COLON CANCER

CROSS REFERENCE TO RELATED APPLICATIONS

This application claims priority to U.S. Provisional Application No. 61/702,423, filed on Sep. 18, 2012, and U.S. Provisional Application No. 61/731,506, filed on Nov. 30, 2012, the contents of each application are incorporated by reference herein, in their entirety and for all purposes.

REFERENCE TO A SEQUENCE LISTING

This application includes a Sequence Listing submitted electronically as a text file named CC Genomic Instability_ST25.txt, created on Mar. 10, 2013 with a size of 180,000 bytes. The Sequence Listing is incorporated by reference herein.

FIELD OF THE INVENTION

The invention relates generally to the field of cancer diagnostics. More particularly, the invention relates to methods for diagnosing a predisposition to develop colon cancer. The invention also relates to arrays, systems, polynucleotides, and polypeptides, which may be used for practicing diagnostic methods.

BACKGROUND OF THE INVENTION

Various publications, including patents, published applications, accession numbers, technical articles and scholarly articles are cited throughout the specification. Each of these cited publications is incorporated by reference, in its entirety and for all purposes, in this document.

Colon cancer is the second most common fatal cancer in the United States. About one quarter of colon cancer appears to have an inherited predisposition in that families show a greater frequency of the disease than the general population (e.g., the cancer is familial), and/or the cancer manifests an early age of onset (less than age 50). In most such cases, the molecular cause of the predisposition to cancer is unknown.

Currently, in the absence of such insight, many patients who are suspected of a predisposition to develop colon cancer but do not carry an increased risk needlessly receive frequent invasive and expensive colon examinations, while others who harbor an unrecognized predisposition fail to receive potentially life-saving colon examinations. There is a need for better diagnostics for predicting patient risk factors for developing colon cancer that may aid in early detection, facilitate screening of patients at risk, and reduce the need for invasive tests on patients with reduced risk factors.

SUMMARY OF THE INVENTION

The invention features methods for diagnosing a predisposition to develop colon cancer. The methods may, for example, comprise determining the quantity of gamma-H2AX foci in a cell or cell nucleus sample obtained from a subject, comparing the determined quantity with reference values for a quantity of gamma-H2AX foci indicative of a predisposition to develop colon cancer, and optionally with reference values for a quantity of gamma-H2AX indicative of a lack of a predisposition to develop colon cancer, and diagnosing whether the subject has a predisposition to develop colon cancer based on the comparison. The methods may comprise determining genomic instability in a nucleic acid sample obtained from a subject, comparing the type of genomic instability with reference values for a type of genomic instability indicative of a predisposition to develop colon cancer, and optionally with reference values for a type of genomic instability indicative of a lack of a predisposition to develop colon cancer, and diagnosing whether the subject has a predisposition to develop colon cancer based on the comparison. The methods may comprise determining double stranded DNA breaks in a nucleic acid sample obtained from a subject, comparing the determined quantity of breaks with reference values for a quantity of breaks indicative of a predisposition to develop colon cancer, and optionally with reference values for a quantity or location of breaks indicative of a lack of a predisposition to develop colon cancer, and diagnosing whether the subject has a predisposition to develop colon cancer based on the comparison. The methods may comprise determining a surrogate of double stranded DNA breaks such as a quantity of one or more of phosphorylated ataxia telangiectasia mutated (ATM), Rad3-related protein (ATR), and Tumor suppressor p53-binding protein 1 (53BP1) in gamma-H2AX foci, comparing the determined quantity of ATM, ATR, and/or 53BP1 in the gamma-H2AX foci with reference values for a quantity of ATM, ATR, and/or 53BP1 in gamma-H2AX foci indicative of a predisposition to develop colon cancer, and optionally with reference values for a quantity of ATM, ATR, and/or 53BP1 in gamma-H2AX foci indicative of a lack of a predisposition to develop colon cancer, and diagnosing whether the subject has a predisposition to develop colon cancer based on the comparison.

The comparing step may be carried out using a processor programmed to compare determined quantities of gamma-H2AX foci with reference values of a quantity of gamma-H2AX foci, or programmed to compare determined types of genomic instability with reference values of types of genomic instability, programmed to compare a determined quantity or location of double stranded DNA breaks with reference values of quantities or locations of double stranded DNA breaks, or programmed to compare a determined quantity of ATM, ATR, and/or 53BP1 in gamma-H2AX foci with reference values for ATM, ATR, and/or 53BP1 in gamma-H2AX foci. The reference values may indicate a high, moderate, low, or no significant probability of a subject having a predisposition to develop colon cancer. The methods may further comprise determining variations in one or more of the ERCC6 gene, the WRN gene, the TERT gene, or the FAAP100 gene associated with causing genomic instability, a DNA damage response, or a predisposition to develop colon cancer. In some aspects, the variations may be any variation described or exemplified herein. Determining such gene variations may be carried out according to any method described or exemplified herein.

In some aspects, the methods comprise determining whether a nucleic acid comprising the ERCC6 gene obtained from a subject encodes a tyrosine at position 180 of the Cockayne Syndrome B protein, and diagnosing whether the subject has a predisposition to develop colon cancer based on the presence or absence of a nucleic acid sequence encoding tyrosine at position 180. In some aspects, the methods comprise determining whether a nucleic acid comprising the WRN gene obtained from a subject encodes an isoleucine at position 705 of the Werner protein, or encodes a tyrosine at position 1292 of the Werner protein, and diagnosing whether the subject has a predisposition to develop colon cancer based on the presence or absence of a nucleic acid sequence encoding isoleucine at position 705 or a nucleic acid sequence encoding tyrosine at position 1292. In some aspects, the methods comprise determining whether a nucleic acid comprising the TERT gene obtained from a subject encodes an arginine at position 198 of the Telomerase Reverse Transcriptase protein, and diagnosing whether the subject has a predisposition to develop colon cancer based on the presence or absence of a nucleic acid sequence encoding arginine at position 198. In some aspects, the methods comprise determining whether a nucleic acid comprising the FAAP100 gene obtained from a subject encodes a leucine at position 466 of the Fanconi anemia associated protein of 100 kD protein, and diagnosing whether the subject has a predisposition to develop colon cancer based on the presence or absence of a nucleic acid sequence encoding leucine at position 466.

The determining step may comprise determining the sequence of the nucleic acid comprising the ERCC6 gene, comparing the determined sequence with one or more reference nucleic acid sequences encoding a tyrosine at position 180 of the Cockayne Syndrome B protein and optionally one or more reference nucleic acid sequences that do not encode a tyrosine at position 180 of the Cockayne Syndrome B protein, and determining whether the determined sequence encodes a tyrosine at position 180 based on the comparison. The determining step may comprise determining the sequence of the nucleic acid comprising the WRN gene, comparing the determined sequence with one or more reference nucleic acid sequences encoding an isoleucine at position 705 of the Werner protein or one or more reference nucleic acid sequences encoding a tyrosine at position 1292 of the Werner protein, and optionally one or more reference nucleic acid sequences that do not encode an isoleucine at position 705 or a tyrosine at position 1292 of the Werner protein, and determining whether the determined sequence encodes an isoleucine at position 705 or a tyrosine at position 1292 based on the comparison. The determining step may comprise determining the sequence of the nucleic acid comprising the TERT gene, comparing the determined sequence with one or more reference nucleic acid sequences encoding an arginine at position 198 of the Telomerase Reverse Transcriptase protein and optionally one or more reference nucleic acid sequences that do not encode an arginine at position 198 of the Telomerase Reverse Transcriptase protein, and determining whether the determined sequence has the alteration based on the comparison. The determining step may comprise determining the sequence of the nucleic acid comprising the FAAP100 gene, comparing the determined sequence with one or more reference nucleic acid sequences encoding a leucine at position 466 of the Fanconi anemia associated protein of 100 kD and optionally one or more reference nucleic acid sequences that do not encode a leucine at position 466 of the Fanconi anemia associated protein of 100 kD, and determining whether the determined sequence encodes a leucine at position 466 based on the comparison. The comparing step may be carried out using a processor programmed to compare determined nucleic acid sequences and reference nucleic acid sequences.

The determining step may comprise contacting the nucleic acid obtained from a subject with one or more polynucleotide probes having a nucleic acid sequence complementary to a nucleic acid sequence encoding a tyrosine at position 180 of the Cockayne Syndrome B protein under stringent conditions, and optionally contacting the nucleic acid obtained from a subject with one or more reference polynucleotide probes having a nucleic acid sequence complementary to a nucleic acid sequence that does not encode a tyrosine at position 180 of the Cockayne Syndrome B protein under stringent conditions, determining whether the one or more probes, and optionally, whether the one or more reference polynucleotide probes, have hybridized with the nucleic acid obtained from the subject, and determining whether the subject has a predisposition to develop colon cancer based on the determination of whether the probes or reference probes have hybridized with the nucleic acid. The determining step may comprise contacting the nucleic acid obtained from a subject with one or more polynucleotide probes having a nucleic acid sequence complementary to a nucleic acid sequence encoding an isoleucine at position 705 of the Werner protein under stringent conditions, or one or more polynucleotide probes having a nucleic acid sequence complementary to a nucleic acid sequence encoding a tyrosine at position 1292 of the Werner protein under stringent conditions, and optionally contacting the nucleic acid obtained from a subject with one or more polynucleotide probes having a nucleic acid sequence complementary to a nucleic acid sequence that does not encode an isoleucine at position 705 or a tyrosine at position 1292 of the Werner protein, determining whether the one or more probes, and optionally, whether the one or more reference probes, have hybridized with the nucleic acid obtained from the subject, and determining whether the subject has a predisposition to develop colon cancer based on the determination of whether the probes have hybridized with the nucleic acid. The determining step may comprise contacting the nucleic acid obtained from a subject with one or more polynucleotide probes having a nucleic acid sequence complementary to a nucleic acid sequence encoding an arginine at position 198 of the Telomerase Reverse Transcriptase protein under stringent conditions, and optionally contacting the nucleic acid obtained from a subject with one or more polynucleotide probes having a nucleic acid sequence complementary to a nucleic acid sequence that does not encode an arginine at position 198 of the Telomerase Reverse Transcriptase protein under stringent conditions, determining whether the one or more probes, and optionally, whether the one or more reference probes, have hybridized with the nucleic acid obtained from the subject, and determining whether the subject has a predisposition to develop colon cancer based on the determination of whether the probes have hybridized with the nucleic acid. The determining step may comprise contacting the nucleic acid obtained from a subject with one or more polynucleotide probes having a nucleic acid sequence complementary to a nucleic acid sequence encoding a leucine at position 466 of the Fanconi anemia associated protein of 100 kD under stringent conditions, and optionally contacting the nucleic acid obtained from a subject with one or more reference polynucleotide probes having a nucleic acid sequence complementary to a nucleic acid sequence that does not encode a leucine at position 466 of the Fanconi anemia associated protein of 100 kD under stringent conditions, determining whether the one or more probes, and optionally, whether the one or more reference polynucleotide probes, have hybridized with the nucleic acid obtained from the subject, and determining whether the subject has a predisposition to develop colon cancer based on the determination of whether the probes or reference probes have hybridized with the nucleic acid. The nucleic acid may be comprised within a cell, and the method may comprise contacting the nucleic acid in the cell with the one or more polynucleotide probes, and optionally with the one or more reference polynucleotide probes. If more than one probe was contacted with the nucleic acid, the method may comprise the step of identifying which of the probes hybridized with the nucleic acid.

The methods may further comprise determining the presence or absence of genomic instability in subjects determined to have one or more of the ERCC6, WRN, TERT, or FAAP100 gene alterations described or exemplified herein. Genomic instability may comprise aneuploidy or polyploidy among the subject's chromosomes. Genomic instability may comprise one or more of chromosomal translocations, chromosomal inversions, chromosome deletions, broken DNA chains, or abnormal DNA structure. Genomic instability may comprise double stranded DNA breaks. Determining the presence or absence of genomic instability may be carried out using any methodology suitable in the art, including those described or exemplified herein. Such methods include, without limitation, karyotyping, metaphase spreads, flow cytometry of propidium iodide-stained cells, immunofluorescence, immunohistochemistry, and determination of the activation of a DNA damage response.

A nucleic acid sequence encoding tyrosine at position 180 may comprise an A to T substitution in the codon encoding asparagine at position 180 of the Cockayne Syndrome B protein. The A to T substitution may occur at a position corresponding to position number 50,408,777 in the ERCC6 gene locus of human chromosome number 10. The Cockayne Syndrome B protein may comprise the amino acid sequence of SEQ ID N0:5.

A nucleic acid sequence encoding an isoleucine at position 705 of the Werner protein may comprise a C to T substitution in the codon encoding threonine at position 705 of the Werner protein. The C to T substitution may occur at a position corresponding to position number 31,088,698 in the WRN gene locus of human chromosome number 8. A nucleic acid sequence encoding a tyrosine at position 1292 of the Werner protein may comprises a C to A substitution in the codon encoding serine at position 1292 of the Werner protein. The C to A substitution may occur at a position corresponding to position number 31,134,481 in the WRN gene locus of human chromosome number 8. The Werner protein may comprise the amino acid sequence of SEQ ID N0:10.

A nucleic acid sequence encoding arginine at position 198 may comprise a G to C substitution in the codon encoding glycine at position 198 of the Telomerase Reverse Transcriptase protein. The G to C substitution may occur at a position corresponding to position number 1,347,409 in the TERT gene locus of human chromosome number 5. The Telomerase Reverse Transcriptase protein may comprise the amino acid sequence of SEQ ID NO:19.

A nucleic acid sequence encoding leucine at position 466 may comprise a C to T substitution in the codon encoding serine at position 466 of the Fanconi anemia associated protein of 100 kD. The C to T substitution may occur at a position corresponding to position number 77,124,711 in the FAAP100 gene locus of human chromosome number 17. The Fanconi anemia associated protein of 100 kD may comprise the amino acid sequence of SEQ ID NO:24.

The invention also features isolated polynucleotides. The polynucleotides may be affixed to a support, including an array. In some aspects, an isolated polynucleotide comprises the ERCC6 gene comprising a nucleic acid sequence encoding a tyrosine at position 180 of the Cockayne Syndrome B protein. The ERCC6 gene may comprise an A to T substitution at a position corresponding to position number 50,408,777 in the ERCC6 gene locus of human chromosome number 10. The nucleic acid sequence may comprise SEQ ID NO:1. The nucleic acid sequence may encode the amino acid sequence of SEQ ID NO:4.

In some aspects, an isolated polynucleotide comprises the WRN gene comprising a nucleic acid sequence encoding an isoleucine at position 705 of the Werner protein. The WRN gene may comprises a C to T substitution at a position corresponding to position number 31,088,698 in the WRN gene locus of human chromosome number 8. The nucleic acid sequence may comprise SEQ ID NO:6. The nucleic acid sequence may encode the amino acid sequence of SEQ ID NO:9.

In some aspects, an isolated polynucleotide comprises the WRN gene comprising a nucleic acid sequence encoding a tyrosine at position 1292 of the Werner protein. The WRN gene may comprise a C to A substitution at a position corresponding to position number 31,134,481 in the WRN gene locus of human chromosome number 8. The nucleic acid sequence may comprise SEQ ID NO:13. The nucleic acid sequence may encode the amino acid sequence of SEQ ID NO:14. The nucleic acid sequence may comprise SEQ ID NO:11. The nucleic acid sequence may encode the amino acid sequence of SEQ ID NO:12.

In some aspects, an isolated polynucleotide comprises the TERT gene comprising a nucleic acid sequence encoding an arginine at position 198 of the Telomerase Reverse Transcriptase protein. The TERT gene may comprise a G to C substitution at a position corresponding to position number 1,347,409 in the TERT gene locus of human chromosome number 5. The nucleic acid sequence may comprise SEQ ID NO:15. The nucleic acid sequence may encode the amino acid sequence of SEQ ID NO:18.

In some aspects, an isolated polynucleotide comprises the FAAP100 gene comprising a nucleic acid sequence encoding a leucine at position 466 of the Fanconi anemia associated protein of 100 kD. The FAAP100 gene may comprises a C to T substitution at a position corresponding to position number 77,124,711 in the FAAP100 gene locus of human chromosome number 17. The nucleic acid sequence may comprise SEQ ID NO:20. The nucleic acid sequence may encode the amino acid sequence of SEQ ID NO:23.

BRIEF DESCRIPTION OF THE DRAWINGS

FIG. 3 shows multiple reads of the ERCC6 variant from patient 120713, affirming validity of the N180Y change in the CSB protein sequence.

FIG. 4 shows the location of the CSB protein variant N180Y (arrow) in patient 120713 within a highly conserved region predicted to be a surface-exposed region of the protein, and therefore functionally significant. Amino acids predicted to be functionally significant are designated by bold typeface.

FIG. 5 shows multiple reads of the WRN gene sequence variants from patients 120713 and 118294, affirming validity of the T705I (top panel) and S1292Y (bottom panel) changes in the Werner protein sequence.

DETAILED DESCRIPTION OF THE INVENTION

Figure 1A:
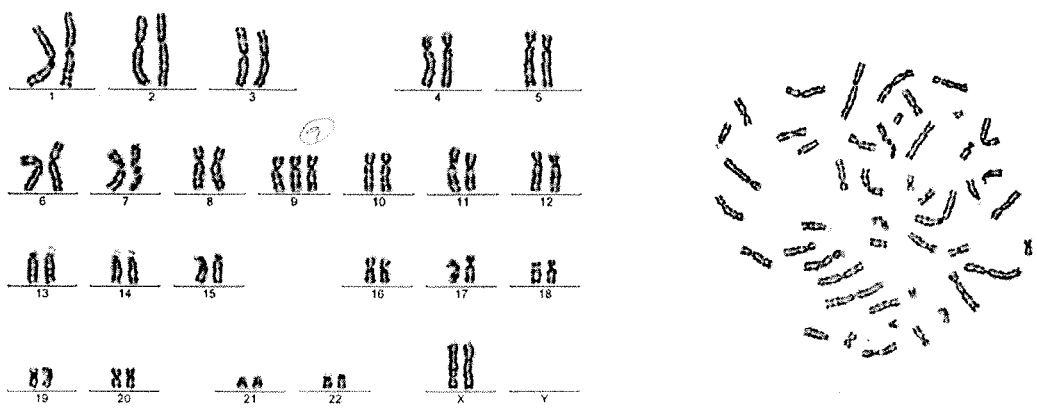
FIG. 1A shows a metaphase spread (right panel) from patient 120713, showing a gain of chromosome 9 as identified on the ordered array (left panel). Phytohemaglutinen (PHA)-stimulated peripheral blood lymphocytes were used as a source of the chromosomes.

Various terms relating to aspects of the present invention are used throughout the specification and claims. Such terms are to be given their ordinary meaning in the art, unless otherwise indicated. Other specifically defined terms are to be construed in a manner consistent with the definition provided in this document.

As used throughout, the singular forms "a," "an," and "the" include plural referents unless expressly stated otherwise.

A molecule such as a polynucleotide has been "isolated" if it has been removed from its natural environment and/or altered by the hand of a human being.

A nucleotide in a nucleic acid sequence such as but not limited to a cDNA, mRNA, or derivative thereof may correspond to a nucleotide in the genomic nucleic acid sequence. In this respect, corresponding to comprises a positional relationship of nucleotides in the genomic DNA gene sequence relative to nucleotides in a polynucleotide sequence (e.g., cDNA, mRNA) obtainable from the genomic DNA sequence.

The terms subject and patient are used interchangeably. A subject may be any animal, and preferably is a mammal. A mammalian subject may be a farm animal (e.g., sheep, horse, cow, pig), a companion animal (e.g., cat, dog), a rodent or laboratory animal (e.g., mouse, rat, rabbit), or a non-human primate (e.g., old world monkey, new world monkey). Human beings are highly preferred.

It has been observed in accordance with the invention that certain variations, which include deletions, substitutions, rearrangements, and combinations thereof, in the germline nucleic acid sequence of one or more of the Excision Repair Cross-Complementing Rodent Repair Deficiency Complementation Group 6 (ERCC6) gene, the Werner Syndrome RecQ Helicase-like (WRN) gene, the Telomerase Reverse Transcriptase (TERT) gene, and the Fanconi anemia associated protein of 100 kD (FAAP100) predispose subjects having such variations to genomic instability, double stranded DNA breaks, and/or extensive phosphorylation of the histone H2AX, forming gamma-H2AX foci proximal to the DNA breaks. It has also been observed that certain DNA damage response proteins such as phosphorylated ataxia telangiectasia mutated (ATM), Rad3-related protein (ATR), and Tumor suppressor p53-binding protein 1 (53BP1) are recruited into such foci. Without intending to be limited to any particular theory or mechanism of action, it is believed that such genomic instability, double stranded DNA breaks, and/or enhanced gamma-H2AX foci are markers of a predisposition to develop colon cancer. Accordingly, the invention features methods for diagnosing a predisposition to develop colon cancer. Any of the methods may be carried out in vivo, in vitro, or in situ.

In general, the methods comprise determining genomic instability and/or double stranded DNA breaks in a nucleic acid sample obtained from a subject, and/or determining gamma-H2AX foci in a cell or cell nucleus sample obtained from a subject. Determining genomic instability, double stranded DNA breaks, and/or gamma-H2AX foci may be carried out according to any suitable method, including the methods described or exemplified herein. The determined genomic instability, double stranded DNA breaks, and/or gamma-H2AX foci may be compared with quantitative or qualitative reference values for genomic instability, double stranded DNA breaks, and/or gamma-H2AX foci associated with a predisposition to develop colon cancer, and optionally with quantitative or qualitative reference values for genomic instability, double stranded DNA breaks, and/or gamma-H2AX foci not associated with a predisposition to develop colon cancer, for example, reference values of a healthy subject or a subject not at risk to develop colon cancer based on these markers. The reference values may, for example, comprise values indicative of a high risk for developing colon cancer, values indicative of a moderate risk for developing colon cancer, and/or values indicative of a low risk for developing colon cancer. The comparing step may be carried out using a processor programmed to compare determined quantitative or qualitative values for genomic instability, double stranded DNA breaks, and/or gamma-H2AX foci with quantitative or qualitative reference values for such markers.

The methods for diagnosing a predisposition to develop colon cancer may further comprise (e.g., in addition to determining genomic instability, double stranded DNA breaks, and/or gamma-H2AX foci), or comprise in the alternative (e.g., without determining genomic instability, double stranded DNA breaks, and/or gamma-H2AX foci), identifying germline nucleic acid sequence alterations in the ERCC6, WRN, TERT, and/or FAAP100 genes that predispose a subject to develop colon cancer. In some aspects, the methods comprise determining whether a nucleic acid comprising the ERCC6, WRN, TERT, and/or FAAP100 gene obtained from a subject comprises an alteration in the nucleic acid sequence that has been associated with predisposing a subject to develop colon cancer. In some detailed aspects, the methods comprise comparing nucleic acid sequences. For example, such methods may comprise the steps of comparing the sequence of a nucleic acid comprising the ERCC6, WRN, TERT, and/or FAAP100 gene obtained from a tissue sample obtained from a subject with one or more reference nucleic acid sequences comprising one or more alterations in the ERCC6, WRN, TERT, and/or FAAP100 germline sequence that predispose a subject to genomic instability, and determining whether the ERCC6, WRN, TERT, and/or FAAP100 gene sequence obtained from the subject has the alteration based on the comparison. The comparing step may be carried out using a processor programmed to compare nucleic acid sequences, for example, to compare the nucleic acid sequences obtained from the subject and the reference nucleic acid sequences. The methods may optionally include the step of determining the sequence of the nucleic acid comprising the ERCC6, WRN, TERT, and/or FAAP100 gene obtained from the subject. The methods may comprise the step of diagnosing whether the subject has a predisposition to genomic instability and/or has a predisposition to develop colon cancer based on the presence or absence of an alteration associated with a predisposition to genomic instability and/or to develop colon cancer in the nucleic acid comprising the ERCC6, WRN, TERT, and/or FAAP100 gene obtained from the subject.

From the subject, the sample may be from any tissue or cell in which genomic DNA or a genomic DNA sequence may be obtained. Non-limiting examples include blood, hair, and buccal tissue or cells. The methods may include the step of obtaining the tissue sample, and may include the step of obtaining the nucleic acid, and may include the step of obtaining a cell nucleus. The nucleic acid may be any nucleic acid that has, or from which may be determined, the presence and/or quantity of genomic instability or double stranded DNA breaks, and the cell or nucleus may be any cell or nucleus that has, or from which may be determined, the presence and/or quantity of gamma-H2AX foci. The nucleic acid may be any nucleic acid that has, or from which may be obtained, the germline nucleic acid sequence of the ERCC6, WRN, TERT, and/or FAAP100 genes, or the complement thereof, or any portion thereof. For example, the nucleic acid may be chromosomal or genomic DNA, may be mRNA, or may be a cDNA obtained from the mRNA. The sequence of the nucleic acid may be determined using any sequencing method suitable in the art.

In some detailed aspects, the methods comprise hybridizing nucleic acids. For example, such methods may comprise the steps of contacting (preferably under stringent conditions), a nucleic acid comprising the ERCC6, WRN, TERT, and/or FAAP100 gene obtained from the subject with one or more polynucleotide probes that have a nucleic acid sequence complementary to an ERCC6, WRN, TERT, and/or FAAP100 nucleic acid sequence having one or more alterations that predispose a subject to develop colon cancer, and determining whether the one or more probes hybridized with the nucleic acid comprising the ERCC6, WRN, TERT, and/or FAAP100 gene obtained from the subject. The methods may comprise the step of diagnosing whether the subject has a predisposition to develop colon cancer based on whether the probes have hybridized with the nucleic acid.

The probes may comprise a detectable label. The nucleic acid obtained from a subject may be labeled with a detectable label. Detectable labels may be any suitable chemical label, metal label, enzyme label, fluorescent label, radiolabel, or combination thereof. The methods may comprise detecting the detectable label on probes hybridized with the nucleic acid comprising the ERCC6, WRN, TERT, and/or FAAP100 gene. The probes may be affixed to a support, such as an array. For example, a labeled nucleic acid obtained from a subject may be contacted with an array of probes affixed to a support. The probes may include any probes described or exemplified herein.

In some detailed aspects, the hybridization may be carried out in situ, for example, in a cell obtained from the subject. For example, the methods may comprise contacting (preferably under stringent conditions) a cell comprising a nucleic acid comprising the ERCC6, WRN, TERT, and/or FAAP100 gene obtained from the subject, or contacting (preferably under stringent conditions) a nucleic acid in the cell, with one or more polynucleotide probes comprising a nucleic acid sequence complementary to a ERCC6, WRN, TERT, and/or FAAP100 germline nucleic acid sequence having one or more alterations that predispose a subject to develop colon cancer and determining whether the one or more probes hybridized with the nucleic acid comprising the ERCC6, WRN, TERT, and/or FAAP100 gene in the cell. The methods may comprise the step of diagnosing whether the subject has a predisposition to develop colon cancer based on whether the probes have hybridized with the nucleic acid. The probes may comprise a detectable label, and the method may comprise detecting the detectable label on probes hybridized with the nucleic acid comprising the ERCC6, WRN, TERT, and/or FAAP100 gene. Detectable labels may be any suitable chemical label, metal label, enzyme label, fluorescent label, radiolabel, or combination thereof.

In any of the hybridization assays, the probes may be DNA or RNA, are preferably single stranded, and may have any length suitable for avoiding cross-hybridization of the probe with a second target having a similar sequence with the desired target. Suitable lengths are recognized in the art as from about 20 to about 60 nucleotides optimal for many hybridization assays (for example, see the Resequencing Array Design Guide available from Affymetrix: http://www.affymetrix.com/support/technical/byproduct.affx?product=cseq), though any suitable length may be used, including shorter than 20 or longer than 60 nucleotides. It is preferred that the probes hybridize under stringent conditions to the ERCC6, WRN, TERT, and/or FAAP100 nucleic acid sequence of interest. It is preferred that the probes have 100% complementary identity with the target sequence.

The methods described herein, including the hybridization assays, whether carried out in vitro, on an array, or in situ, may be used to determine any alteration in the ERCC6, WRN, TERT, and/or FAAP100 germline nucleic acid sequence that has a known or suspected association with predisposing a subject to genomic instability and/or to develop colon cancer, including any of those described or exemplified herein. In any of the methods described herein, the alterations may be, for example, a mutation or variation in the germline nucleic acid sequence relative to a germline nucleic acid sequence that has no known or suspected association with predisposing a subject to develop colon cancer. The alteration may comprise one or more nucleotide substitutions, an addition of one or more nucleotides in one or more locations, a deletion of one or more nucleotides in one or more locations, an inversion or other DNA rearrangement, or any combination thereof. A substitution may, but need not, change the amino acid sequence of the protein encoded by the ERCC6, WRN, TERT, and/or FAAP100 gene. Any number of substitutions, additions, or deletions of nucleotides are possible. The alteration may occur in an intron, an exon, or both.

The one or more alterations in the ERCC6 gene may be located in human chromosome 10, for example, at segment 10q11.2. One non-limiting example of a particular alteration that may predispose a subject to develop colon cancer includes an A to T substitution in exon 3. The substitution may occur at position 50,408,777 of human chromosome 10, and may comprise an A to T substitution at this position. The substitution may comprise a polynucleotide having the nucleic acid sequence of SEQ ID NO:1. The polynucleotide having the substitution may comprise SEQ ID NO:1, or a portion thereof. The substitution may occur in the polynucleotide at the position corresponding to position 537 of SEQ ID NOs:1 or 2, and may comprise an A to T substitution at this position. The substitution may occur in the polynucleotide at the position corresponding to position 692 of the mRNA nucleic acid sequence of Accession No. NM_000124 (SEQ ID NO: 3), and may comprise an A to T substitution at this position.

The ERCC6 gene encodes the Cockayne Syndrome B protein (CSB protein). Thus, in some aspects, one or more alterations in the ERCC6 gene may change the amino acid sequence of the CSB protein. One non-limiting example of a particular amino acid alteration that may predispose a subject to develop colon cancer includes an asparagine to tyrosine substitution at position 180 in the CSB protein. The amino acid alteration may comprise a polypeptide having the amino acid sequence of SEQ ID NO:4. The amino acid alteration may comprise a substitution of tyrosine with asparagine in the position corresponding to position 180 in the CSB protein sequence of SEQ ID NO:5. In some aspects, nucleic acid alterations in the ERCC6 gene encode a tyrosine at position 180 in the CSB protein. Thus, the methods may comprise determining whether a nucleic acid comprising the ERCC6 gene obtained from the subject encodes a tyrosine at position 180 of the CSB protein.

The one or more alterations in the WRN gene may be located in human chromosome 8, for example, at segment 8p12. One non-limiting example of a particular alteration that may predispose a subject to develop colon cancer includes a C to T substitution in exon 19. The substitution may occur at position 31,088,698 of human chromosome 8, and may comprise a C to T substitution at this position. The substitution may comprise a polynucleotide having the nucleic acid sequence of SEQ ID NO:6. The polynucleotide having the substitution may comprise SEQ ID NO:6, or a portion thereof. The substitution may occur in the polynucleotide at the position corresponding to position 2113 of SEQ ID NOs:6 or 7, and may comprise a C to T substitution at this position. The substitution may occur in the polynucleotide at the position corresponding to position 2902 of the mRNA nucleic acid sequence of Accession No. NM_000553 (SEQ ID NO:8), and may comprise a C to T substitution at this position.

Another non-limiting example of a particular WRN gene alteration that may predispose a subject to develop colon cancer includes a C to A substitution in exon 19. The substitution may occur at position 31,134,481 of human chromosome 8, and may comprise a C to A substitution at this position. The substitution may comprise a polynucleotide having the nucleic acid sequence of SEQ ID NO:11. The polynucleotide having the substitution may comprise SEQ ID NO:11, or a portion thereof. The substitution may occur in the polynucleotide at the position corresponding to position 3875 of SEQ ID NOs:11 or 7, and may comprise a C to A substitution at this position. The substitution may occur in the polynucleotide at the position corresponding to position 4663 of the mRNA nucleic acid sequence of Accession No. NM_000553 (SEQ ID NO:8), and may comprise a C to A substitution at this position.

In some aspects, the WRN gene may include both the C to T alteration at position 31,088,698 of human chromosome 8 and the C to A alteration at position 31,134,481 of human chromosome 8. The dual substitution may comprise a polynucleotide having the nucleic acid sequence of SEQ ID NO:13. The polynucleotide having the substitution may comprise SEQ ID NO:13, or a portion thereof. The dual substitution may occur in the polynucleotide at the position corresponding to position 2113 and position 3875 of SEQ ID NO:6, 7, or 11, and may comprise a C to T substitution at position 2113 and a C to A substitution at position 3875. The dual substitution may occur in the polynucleotide at the position corresponding to position 2902 and the position corresponding to position 4663 of the mRNA nucleic acid sequence of Accession No. NM_000553 (SEQ ID NO:8), and may comprise a C to T substitution at position 2902 and a C to A substitution at position 4663.

The WRN gene encodes the Werner protein. Thus, in some aspects, one or more alterations in the WRN gene may change the amino acid sequence of the Werner protein. One non-limiting example of a particular amino acid alteration that may predispose a subject to develop colon cancer includes a threonine to isoleucine substitution at position 705 in the Werner protein. The amino acid alteration may comprise a polypeptide having the amino acid sequence of SEQ ID NO:9. The amino acid alteration may comprise a substitution of threonine with isoleucine in the position corresponding to position 705 in the Werner protein sequence of SEQ ID NO:10. In some aspects, nucleic acid alterations in the WRN gene encode an isoleucine at position 705 in the Werner protein. Thus, the methods may comprise determining whether a nucleic acid comprising the WRN gene obtained from the subject encodes an isoleucine at position 705 of the Werner protein.

Another non-limiting example of a particular amino acid alteration that may predispose a subject to develop colon cancer includes a serine to tyrosine substitution at position 1292 in the Werner protein. The amino acid alteration may comprise a polypeptide having the amino acid sequence of SEQ ID NO:12. The amino acid alteration may comprise a substitution of serine with tyrosine in the position corresponding to position 1292 in the Werner protein sequence of SEQ ID NO:10. In some aspects, nucleic acid alterations in the WRN gene encode a tyrosine at position 1292 in the Werner protein. Thus, the methods may comprise determining whether a nucleic acid comprising the WRN gene obtained from the subject encodes a tyrosine at position 1291 of the Werner protein.

In some aspects, two or more alterations in the Werner protein amino acid sequence may predispose a subject to develop colon cancer. For example, the altered Werner protein amino acid sequence may comprise a threonine to isoleucine substitution at position 705 and a serine to tyrosine substitution at position 1292 of the Werner protein. The amino acid alteration may comprise a polypeptide having the amino acid sequence of SEQ ID NO:14. The amino acid alteration may comprise a substitution of threonine with isoleucine at position 705 and a substitution of serine with tyrosine at position 1292 in the Werner protein sequence of SEQ ID NO:10. In some aspects, nucleic acid alterations in the WRN gene encode both an isoleucine at position 705 and a tyrosine at position 1292 in the Werner protein. Thus, the methods may comprise determining whether a nucleic acid comprising the WRN gene obtained from the subject encodes an isoleucine at position 705 of the Werner protein and determining whether a nucleic acid comprising the WRN gene obtained from the subject encodes a tyrosine at position 1292 of the Werner protein.

The one or more alterations in the TERT gene may be located in human chromosome 5, for example, at segment 5p15.3. One non-limiting example of a particular alteration that may predispose a subject to develop colon cancer includes a G to C substitution in exon 2. The substitution may occur at position 1,347,409 of human chromosome 5, and may comprise a G to C substitution at this position. The substitution may comprise a polynucleotide having the nucleic acid sequence of SEQ ID NO:15. The polynucleotide having the substitution may comprise SEQ ID NO:15, or a portion thereof. The substitution may occur in the polynucleotide at the position corresponding to position 591 of SEQ ID NOs:15 or 16, and may comprise a G to C substitution at this position. The substitution may occur in the polynucleotide at the position corresponding to position 650 of the mRNA nucleic acid sequence of Accession No. NM_198253 (SEQ ID NO:17), and may comprise a G to C substitution at this position.

The TERT gene encodes the Telomerase Reverse Transcriptase protein. Thus, in some aspects, one or more alterations in the TERT gene may change the amino acid sequence of the Telomerase Reverse Transcriptase protein. One non-limiting example of a particular amino acid alteration that may predispose a subject to develop colon cancer includes an glycine to arginine substitution at position 198 in the Telomerase Reverse Transcriptase protein. The amino acid alteration may comprise a polypeptide having the amino acid sequence of SEQ ID NO:18. The amino acid alteration may comprise a substitution of glycine with arginine in the position corresponding to position 198 in the amino acid sequence of SEQ ID NO:19. In some aspects, nucleic acid alterations in the TERT gene encode an isoleucine at position 198 in the Telomerase Reverse Transcriptase protein. Thus, the methods may comprise determining whether a nucleic acid comprising the TERT gene obtained from the subject encodes an arginine at position 198 of the Telomerase Reverse Transcriptase protein.

The reference nucleic acid sequences used in nucleic acid sequence comparison aspects of the methods may comprise one or more of SEQ ID NO:1, SEQ ID NO:6, SEQ ID NO:11, SEQ ID NO:13, and SEQ ID NO:15, or portion thereof having one or more alterations associated with a predisposition/risk of developing colon cancer. The reference nucleic acid sequences may also include nucleic acid sequences that do not have any nucleotide alterations that are associated with a predisposition/risk of developing colon cancer to serve as controls in the comparison, or for determinations that the subject does not have a germline nucleic acid sequence alteration that predisposes to develop colon cancer. Non-limiting examples of nucleic acid sequences without such alterations include SEQ ID NO:2, SEQ ID NO:3, SEQ ID NO:7, SEQ ID NO:8, SEQ ID NO:16, and SEQ ID NO:17. Reference nucleic acid sequences having any portion of the sequence of these sequence identifiers may be used.

The FAAP100 gene (also known as C17Orf70) encodes the Fanconi anemia-associated protein of 100 kD. Thus, in some aspects, one or more alterations in the FAAP100 gene may change the amino acid sequence of the Fanconi anemia-associated protein of 100 kD. One non-limiting example of a particular amino acid alteration that may predispose a subject to develop colon cancer includes a serine to leucine substitution at position 466 in the Fanconi anemia-associated protein of 100 kD. The amino acid alteration may comprise a polypeptide having the amino acid sequence of SEQ ID NO:23. The amino acid alteration may comprise a substitution of serine with leucine in the position corresponding to position 466 in the Fanconi anemia-associated protein of 100 kD sequence of SEQ ID NO:24. In some aspects, nucleic acid alterations in the FAAP100 gene encode a leucine at position 466 in the Fanconi anemia-associated protein of 100 kD. Thus, the methods may comprise determining whether a nucleic acid comprising the FAAP100 gene obtained from the subject encodes a leucine at position 466 of the Fanconi anemia-associated protein of 100 kD.

The one or more alterations in the FAAP100 gene may be located in human chromosome 17, for example, at segment 77124711. One non-limiting example of a particular alteration that may predispose a subject to develop colon cancer includes a C to T substitution in exon 4. The substitution may occur at position 77,124,711 of human chromosome 17, and may comprise a C to T substitution at this position. The substitution may comprise a polynucleotide having the nucleic acid sequence of SEQ ID NO:20. The polynucleotide having the substitution may comprise SEQ ID NO:20, or a portion thereof. The substitution may occur in the polynucleotide at the position corresponding to position 1397 of SEQ ID NO:20, and may comprise a C to T substitution at this position. The substitution may occur in the polynucleotide at the position corresponding to position 1443 of the mRNA nucleic acid sequence of Accession No. BC_117141 (SEQ ID NO:22), and may comprise a C to T substitution at this position.

The polynucleotide probes used in nucleic acid hybridization aspects may comprise a portion of one or more of SEQ ID NO:1, SEQ ID NO:6, SEQ ID NO:11, SEQ ID NO:13, SEQ ID NO:15, and SEQ ID NO:20, the portion containing the genomic instability and/or colon cancer risk-associated alteration. The nucleic acid sequence of the probes may be complementary to the relevant portion of SEQ ID NO:1, SEQ ID NO:6, SEQ ID NO:11, SEQ ID NO:13, SEQ ID NO:15, or SEQ ID NO:20.

Polynucleotide probes having a nucleic acid sequence without any alterations associated with a predisposition to develop genomic instability and/or colon cancer may be used to serve as controls in hybridization assays, or for determinations that the subject does not have a germline nucleic acid sequence alteration that predisposes to genomic instablity or colon cancer. Non-limiting examples of nucleic acid sequences without an alteration, from which such probes may be derived, include SEQ ID NO:2, SEQ ID NO:3, SEQ ID NO:7, SEQ ID NO:8, SEQ ID NO:16, SEQ ID NO:17, and SEQ ID NO:21, and the probes may be obtained from the regions of these sequences where the respective alteration is located. The probe nucleic acid sequence may be complementary to the appropriate portion of SEQ ID NO:2, SEQ ID NO:3, SEQ ID NO:7, SEQ ID NO:8, SEQ ID NO:16, SEQ ID NO:17, and SEQ ID NO:20.

The methods for diagnosing, whether based on sequence comparison or probe hybridization, may further comprise the steps of treating the subject with a regimen capable of inhibiting the onset of colon cancer. These steps may be included, for example, if it is determined that the subject has a predisposition to develop colon cancer. In some aspects, the treatment regimen may comprise administering to the subject an effective amount of the CSB, Werner, Telomerase Reverse Transcriptase protein, or Fanconi anemia associated protein of 100 kD or genes that encode these proteins in vectors that can integrate and express in tissue stem cells. In some aspects, the treatment regimen comprises administering to the subject an effective amount of a compound or pharmaceutical composition capable of delaying or inhibiting the onset of colon cancer. In some aspects, the treatment regimen comprises one or more of diet management, vitamin supplementation, nutritional supplementation, exercise, psychological counseling, social counseling, education, and regimen compliance management. In some aspects, the treatment regimen comprises administering to the subject an effective amount of a compound or pharmaceutical composition that enhances the activity of one or more of the CSB protein, the Werner protein, the Telomerase Reverse Transcriptase protein, and the Fanconi anemia associated protein of 100 kD.

In the diagnostic methods, the tissue sample obtained from the subject may be from any tissue in which replicating cells and/or a genomic DNA sequence may be obtained. Non-limiting examples include blood, hair, and buccal tissue. Blood may comprise peripheral blood lymphocytes (PBLs). The methods may include the step of obtaining the tissue sample, and may include the step of obtaining the nucleic acid. The nucleic acid may be any nucleic acid that has, or from which may be obtained, the germline nucleic acid sequence for the ERCC6, WRN, TERT, and/or FAAP100 genes, or the complement thereof, or any portion thereof. For example, the nucleic acid may be chromosomal or genomic DNA, may be mRNA, or may be a cDNA obtained from the mRNA.

The diagnostic methods are preferably based on determining alterations in the germline nucleic acid sequences of the ERCC6, WRN, TERT, and FAAP100 genes that predispose a subject having such alterations to develop colon cancer, including any of the alterations described or exemplified herein. The reference nucleic acid sequences and the probes are thus based on alterations that predispose to develop colon cancer, and based on control sequences that do not have alterations that predispose to develop colon cancer.

The invention also provides isolated polynucleotides comprising a nucleic acid comprising the ERCC6, WRN, TERT, and/or FAAP100 gene and having one or more alterations that predispose a subject to develop colon cancer. The invention also provides isolated polynucleotides comprising a probe having a nucleic acid sequence complementary to a nucleic acid sequence having one or more alterations in the ERCC6, WRN, TERT, and/or FAAP100 gene that predispose a subject to develop colon cancer. Probes may have any suitable number of nucleotide bases. The one or more alterations may be any of the alterations described or exemplified herein. The probes preferably hybridize to a nucleic acid comprising the ERCC6, WRN, TERT, and/or FAAP100 gene under stringent conditions Polynucleotides include polyribonucleotides and polydeoxyribonucleotide, which may be unmodified RNA or DNA or modified RNA or DNA, and include single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. Polynucleotides may have triple-stranded regions comprising RNA or DNA or both RNA and DNA, modified bases, unusual bases such as inosine, modified backbones, and enzymatic or metabolic modifications.

The alterations may comprise, for example, a nucleic acid sequence encoding a tyrosine at position 180 of the CSB protein. The CSB protein may comprise SEQ ID NO:4. A nucleic acid sequence encoding a tyrosine at position 180 of the CSB protein may comprise an A to T substitution in the codon encoding an asparagine at position 180 of the CSB protein, and the A to T substitution may occur at a position corresponding to position number 50,408,777 in the ERCC6 gene locus on human chromosome number 10.

The alterations may comprise, for example, a nucleic acid sequence encoding an isoleucine at position 705 of the Werner protein. The Werner protein may comprise SEQ ID NO:9. A nucleic acid sequence encoding an isoleucine at position 705 of the Werner protein may comprise a C to T substitution in the codon encoding a threonine at position 705 of the Werner protein, and the C to T substitution may occur at a position corresponding to position number 31,008,698 in the WRN gene locus on human chromosome number 8. In addition to, or in the alternative to a nucleic acid sequence encoding an isoleucine at position 705 of the Werner protein, the alteration may comprise a nucleic acid sequence encoding a tyrosine at position 1292 of the Werner protein. The Werner protein may comprise SEQ ID NO:12 or SEQ ID NO:14. A nucleic acid sequence encoding a tyrosine at position 1292 of the Werner protein may comprise a C to A substitution in the codon encoding a serine at position 1292 of the Werner protein, and the C to A substitution may occur at a position corresponding to position number 31,134,481 in the WRN gene locus on human chromosome number 8.

The alterations may comprise, for example, a nucleic acid sequence encoding an arginine at position 198 of the Telomerase Reverse Transcriptase protein. The Telomerase Reverse Transcriptase protein may comprise SEQ ID NO:18. A nucleic acid sequence encoding an arginine at position 198 of the Telomerase Reverse Transcriptase protein may comprise a G to C substitution in the codon encoding a serine at position 198 of the Telomerase Reverse Transcriptase protein, and the G to C substitution may occur at a position corresponding to position number 1,347,409 in the TERT gene locus on human chromosome number 5.

The alterations may comprise, for example, a nucleic acid sequence encoding a leucine at position 466 of the Fanconi anemia associated protein of 100 kD. The Fanconi anemia associated protein of 100 kD may comprise SEQ ID NO:23. A nucleic acid sequence encoding a leucine at position 466 of the Fanconi anemia associated protein of 100 kD may comprise a C to T substitution in the codon encoding a serine at position 466 of the Fanconi anemia associated protein of 100 kD, and the C to T substitution may occur at a position corresponding to position number 77,124,711 in the FAAP100 gene locus on human chromosome number 17.

The invention also features a support comprising a plurality of polynucleotides comprising a nucleic acid sequence, or portion thereof, comprising the ERCC6, WRN, TERT, and/or FAAP100 genes and having one or more alterations in the nucleic acid sequence that predispose a subject to develop colon cancer, and optionally, a plurality of polynucleotides comprising a nucleic acid sequence, or portion thereof, comprising the ERCC6, WRN, TERT, and/or FAAP100 genes and not having any alterations in the nucleic acid sequence that are known to predispose a subject to develop colon cancer. The support may comprise an array. The polynucleotides may be probes. The probes may comprise a portion of the nucleic acid sequence of SEQ ID NO:1, SEQ ID NO:6, SEQ ID NO:11, SEQ ID NO:15, or SEQ ID NO:20 comprising an alteration associated with predisposing a subject to genomic instability and/or to develop colon cancer, and the alteration may comprise any alteration described or exemplified herein. The probes may comprise the complement of the portion of the nucleic acid sequence of SEQ ID NO:1, SEQ ID NO:6, SEQ ID NO:11, SEQ ID NO:15, or SEQ ID NO:20 comprising an alteration associated with predisposing a subject to genomic instability and/or to develop colon cancer.

The invention also features isolated polypeptides, including isolated proteins comprising a polypeptide having an amino acid sequence encoded by a polynucleotide comprising one or more alterations that predispose a subject to develop colon cancer. Polypeptides include polymers of amino acid residues, one or more artificial chemical mimetic of a corresponding naturally occurring amino acid, as well as to naturally occurring amino acid polymers and non-naturally occurring amino acid polymers.

The polypeptides may comprise the CSB protein comprising a tyrosine at position 180. The polypeptides may comprise the Werner protein comprising an isoleucine at position 705. The polypeptides may comprise the Werner protein comprising a tyrosine at position 1292. The polypeptides may comprise the Werner protein comprising an isoleucine at position 705 and a tyrosine at position 1292. The polypeptides may comprise the Telomerase Reverse Transcriptase protein comprising an arginine at position 198. The polypeptides may comprise the Fanconi anemia associated protein of 100 kD comprising a leucine at position 466. The polypeptides may comprise an amino acid sequence encoded by the nucleic acid sequence of SEQ ID NO:1, SEQ ID NO:6, SEQ ID NO:11, SEQ ID NO:15, or SEQ ID NO:20. The polypeptides may comprise the amino acid sequence of SEQ ID NO:4, SEQ ID NO:9, SEQ ID NO:12, SEQ ID NO:18, or SEQ ID NO:23.

The invention also features systems for diagnosing a predisposition to develop colon cancer. In general, the systems comprise a data structure comprising one or more reference nucleic acid sequences having one or more alterations in ERCC6, WRN, TERT, and/or FAAP100 gene associated with predisposing a subject to develop colon cancer, and a processor operably connected to the data structure. Optionally, the data structure may comprise one or more reference nucleic acid sequences that do not have any alterations in the ERCC6, WRN, TERT, and/or FAAP100 genes associated with a predisposition of a subject to develop colon cancer. The processor is preferably capable of comparing, and preferably programmed to compare determined nucleic acid sequences (for example, those determined from nucleic acids obtained from a subject) with reference nucleic acid sequences.

The reference nucleic acid sequences may comprise the one or more alterations described or exemplified herein. For example, the alterations may comprise a nucleic acid sequence encoding a tyrosine at position 180 of the CSB protein. The alterations may comprise a nucleic acid sequence encoding an isoleucine at position 705 of the Werner protein and/or a nucleic acid sequence encoding a tyrosine at position 1292 of the Werner protein. The alterations may comprise a nucleic acid sequence encoding an arginine at position 198 of the Telomerase Reverse Transcriptase protein. The alterations may comprise a nucleic acid encoding a leucine at position 466 of the Fanconi anemia associated protein of 100 kD. The reference nucleic acid sequences may comprise the nucleic acid sequence of one or more of SEQ ID NO:1, SEQ ID NO:2, SEQ ID NO: 6, SEQ ID NO:7, SEQ ID NO:11, SEQ ID NO:13, SEQ ID NO:15, SEQ ID NO:16, SEQ ID NO:20, or SEQ ID NO:21.

Optionally, the system may comprise an input for accepting determined nucleic acid sequences obtained from tissue samples from a subject. Optionally, the system may comprise an output for providing results of a sequence comparison to a user such as the subject, or a technician, or a medical practitioner. Optionally, the system may comprise a sequencer for determining the sequence of a nucleic acid such as a nucleic acid obtained from a subject. Optionally, the system may comprise a detector for detecting a detectable label on a nucleic acid.

Optionally, the system may comprise computer readable media comprising executable code for causing a programmable processor to determine a diagnosis of the subject, for example whether the subject has a predisposition to develop colon based on whether or not a nucleic acid obtained from the subject includes a sequence alteration associated with a predisposition to develop colon cancer. The diagnosis may be based on the comparison of determined nucleic acid sequences with reference nucleic acid sequences. The diagnosis may be based on a determination of hybridization of a nucleic acid probe with a nucleic acid obtained from the subject. Thus, the system may comprise an output for providing a diagnosis to a user such as the subject, or a technician, or a medical practitioner. Optionally, the system may comprise computer readable media that comprises executable code for causing a programmable processor to recommend a treatment regimen for the subject, for example, a treatment regimen for preventing, inhibiting, or delaying the onset of colon cancer.

In any of the systems, a computer may comprise the processor or processors used for determining information, comparing information and determining results. The computer may comprise computer readable media comprising executable code for causing a programmable processor to determine a diagnosis of the subject. The systems may comprise a computer network connection, including an Internet connection.

The invention also provides computer-readable media. In some aspects, the computer-readable media comprise executable code for causing a programmable processor to compare the nucleic acid sequence of the ERCC6, WRN, TERT, and/or FAAP100 gene determined from a nucleic acid obtained from a tissue sample obtained from a subject with one or more reference nucleic acid sequences having one or more alterations in the ERCC6, WRN, TERT, and/or FAAP100 gene sequence associated with predisposing a subject to develop genomic instability and/or to develop colon cancer. The alterations may be any alteration described or exemplified herein. Optionally, the computer-readable media comprise executable code for causing a programmable processor to compare the nucleic acid sequence of the ERCC6, WRN, TERT, and/or FAAP100 gene determined from a nucleic acid obtained from a tissue sample obtained from a subject with one or more reference nucleic acid sequences that do not have any alterations in the ERCC6, WRN, TERT, and/or FAAP100 gene sequence associated with predisposing a subject to genomic instability and/or to develop colon cancer. The computer readable media may comprise a processor, which may be a computer processor.

The reference nucleic acid sequences may comprise any of the one or more alterations described or exemplified herein. For example, the alterations may comprise a nucleic acid sequence encoding a tyrosine at position 180 of the CSB protein. The alterations may comprise a nucleic acid sequence encoding an isoleucine at position 705 of the Werner protein and/or a nucleic acid sequence encoding a tyrosine at position 1292 of the Werner protein. The alterations may comprise a nucleic acid sequence encoding an arginine at position 198 of the Telomerase Reverse Transcriptase protein. The alterations may comprise a nucleic acid encoding a leucine at position 466 of the Fanconi anemia associated protein of 100 kD. The reference nucleic acid sequences may comprise the nucleic acid sequence of one or more of SEQ ID NO:1, SEQ ID NO:2, SEQ ID NO: 6, SEQ ID NO:7, SEQ ID NO:11, SEQ ID NO:13, SEQ ID NO:15 SEQ ID NO:16, SEQ ID NO:20, or SEQ ID NO:21.

The systems and computer readable media may be used in any of the methods described or exemplified herein, for example, methods for diagnosing a predisposition to develop colon cancer. For example, the systems and computer readable media may be used to facilitate comparisons of gene sequences, or to facilitate a diagnosis.

The methods, systems, and computer readable media comprise various reference values. For example, the reference values comprise certain quantities such as a quantity of gamma-H2Ax or a quantity of double stranded DNA breaks, and comprise certain qualities such as the presence or absence of a type of polymorphism in a gene sequence or the presence or absence of a type of genomic instability such as chromosomal aneuploidy. In general, such reference values may be established according to studies of individuals and/or studies of populations. It is contemplated that, over time, as more and more individuals and larger populations are studied, the reference values, particularly the quantitative reference values, may become more precise or established to have a greater confidence. Reference value quantities may comprise quantities based on available information for any given period of time.

The following examples are provided to describe the invention in greater detail. They are intended to illustrate, not to limit, the invention.

EXAMPLE 1

Identification of Sequence Alterations Relevant to Colon Cancer Predisposition

It is believed that dysfunction of genes that maintain genome stability underlies a substantial fraction of familial colorectal carcinoma (FCRC). Based on this hypothesis, preliminary studies utilized colorectal carcinoma (CRC) patients in an in-house Gastrointestinal Cancer Risk Assessment Program who met the following criteria: (1) they developed CRC before the age of 50 and/or had a first degree relative with colon cancer and, (2) had tested negative for Lynch Syndrome/Hereditary Non-Polyposis Colorectal Cancer (HNPCC) by standard tests of their tumor for microsatellite instability and/or immunohistochemistry for levels of mismatch repair proteins and tested negative for Familial Adenomatous Polyposis *coli* by having fewer than five polyps detected by colonoscopy. Many of these patients had clinical features atypical for MUTYH polyposis.

All patients in the Program had donated peripheral blood from which buffy coat white blood cells (WBCs) were frozen in dimethylsulfoxide (DMSO) and used to prepare genomic DNA and had signed a broad consent for research, and Controls were selected from the same BioSample Repository that had no personal history of cancer or cancer in a first degree relative, and were matched by sex and age. Lymphocytes were cultured from eight independent patients, using stimulation with phytohemagluttinin (PHA) and Interleukin 2 (IL-2). Seven samples yielded enough cells to generate metaphase spreads, and several of these yielded enough cells to evaluate by flow cytometry.

Figure 1B:
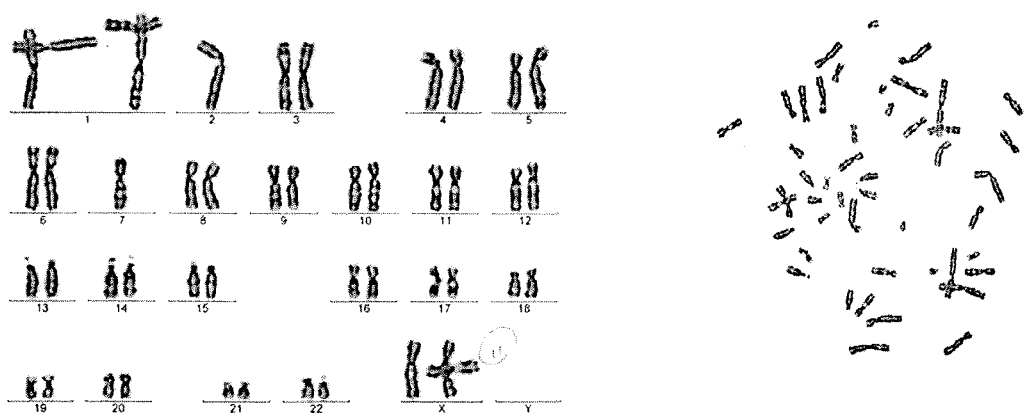
FIG. 1B shows a second metaphase spread (right panel) from patient 120713, showing a gain of chromosome 11 as identified on the ordered array (left panel). Two other gains were identified among 50 well-separated metaphase spreads in patient 120713 (not shown).

Metaphase spreads were generated from proliferating cultures by addition of colcemid, swelling in hypotonic buffer, and dropping from height onto a slide. Chromosomes were stained with Giemsa stain to identify them. At least 50 well-separated spreads with condensed chromosomes from all 7 patients and 3 controls were scored by standard clinical cytogenetics criteria for any notable abnormality, including premature chromatid separation, aneuploidy, and chromosomal rearrangements. One patient, number 120713, showed 4 out of 50 spreads with chromosomal gains (8%; gains are viewed as more reliable than losses), each different (FIG. 1A and FIG. 1B, which show 2 of the 4 spreads). This was an unusually high degree of aneuploidy.

Figure 2:
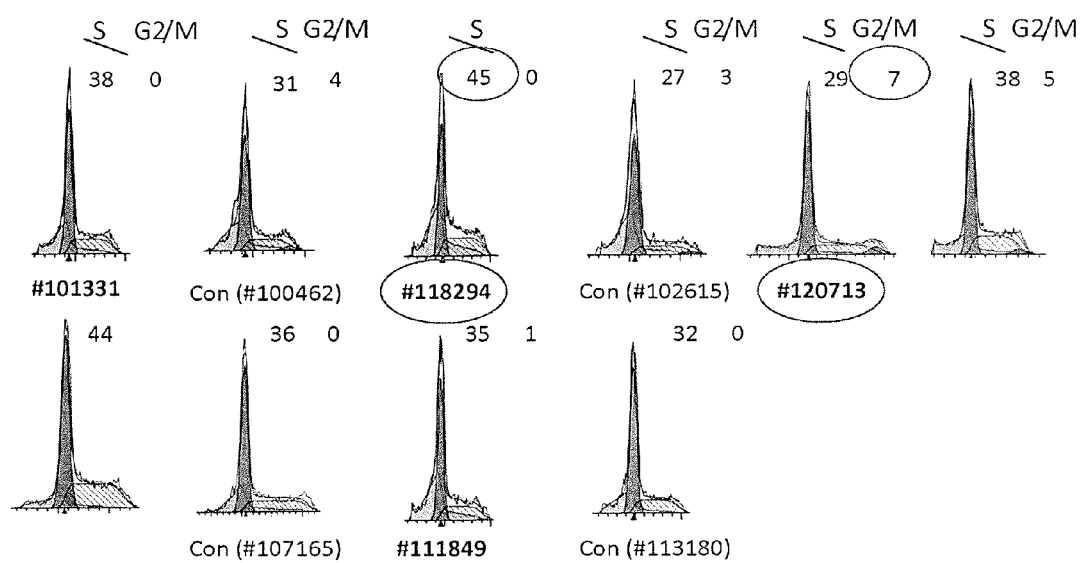
FIG. 2 shows an increased S phase fraction in patient 118294 compared to its matched control (102615) and all other samples, and shows an increase G2/M fraction in patient 120713 compared to its matched control (237313) and all other samples. The plots were obtained from flow cytometry analysis of propidium iodide (PO-stained, PHA-stimulated lymphocytes. S phase fractions are marked by hatching. G2/M phase fractions are shown in dark grey on the right-hand side of the plot.

Only one chromosomal gain was seen in the remaining 6 cases examined (0.2%) and only 3 of 3 controls (1%), consistent with a published mode frequency of gains in normal lymphocytes of 1.3% (Cimino M C et al. (1986) Mutat. Res. 167:107-22). A second patient, number 118294, showed a complex chromosomal rearrangement. Flow cytometry of propidium-iodide-stained cells show the highest level of S phase in this patient, among 3 other cases and 5 controls (FIG. 2). Flow cytometry of cells from patient 120713 showed the highest level of G2/M phase, among the cases and controls. On this basis, patients 120713 and 118294 were selected for further analysis.

Exome sequencing was performed on their peripheral blood DNAs by SeqWright Services (Texas). The library size was good and >85% of target sequences had >20x coverage. All sequence variants were initially screened by eye for potential involvement in cell replication, DNA repair, cell cycle checkpoints or mitosis and the severity of the molecular change. The following uninformative sequence variants were found: (1) non-sense changes in 120713: EFCAB3, C22orf30, SELP, C2orf65, PRAMEEF1, ULK4, and ZNF571; and non-sense changes in 118294: FAM83A, ZNF5858, C17orf58, and ALKBH4; and (2) internal deletions or splice site changes in 120713: FAM113A, C14orf13, MED13L, PDGFD, and HERPUD2; and internal deletions or splice site changes in 118294: TRPM3, FAM113A, FU41603, SPEN, PASK, GAPVD1, SOX1. None of these changes affected proteins with known roles in cell replication and/or genome stability. In addition, patient 120713 displayed 265 missense variants, and patient 118292 displayed 262 missense variants. Among these affected genes, several had roles in replication and/or genome stability: for patient 120713: ERCC6, WRN, CDKN1a, and DUB3, and for patient 118294: TERT, WRN, and EXO1.

Among the missense variants in these latter genes, it is believed that the variants in ERCC6 and TERT had not been previously reported in publicly available single nucleotide polymorphism (SNP) databases (National Heart Lung and Blood Institute Exome Sequencing Project server (http://evs.gs.washington.edu/EVS/). The sequence quality in these regions was verified as excellent by direct inspection, and the reads were unambiguously assigned (FIG. 3).

ERCC6 is a chromatin remodeling protein (CSB protein) that is implicated in transcription-coupled DNA repair. Homozygous inherited inactivating proteins in ERCC6 cause Cockayne syndrome, a growth disorder associated with sensitivity to ultraviolet light. Polymorphisms within the ERCC6 gene have been statistically associated with head and neck tumors, bladder carcinoma, and lung cancer in other studies. The likelihood that these variants degrade protein function was evaluated using Consurf (University of Massachusetts) and PolyPhen2 (PP2; Harvard University) software.

The ERCC6 (CSB) protein variant, N180Y, represents in a tyrosine substitution for asparagine, a non-conservative change in a residue that is completely conserved among vertebrate ERCC6-encoded proteins. Furthermore, this residue is within a stretch of 9 highly conserved residues (FIG. 4) that comprise a coiled-coil motif.

The PP2 program predicted the variant to be probably damaging to function of the protein, with its highest possible confidence score of 1.0. It is believed that the coiled-coil motif currently has no known ascribed function. However, the amino-terminal 400 amino acids have been implicated in three important biochemical function of ERCC6: intramolecular inhibition of ATPase activity, inhibition of non-specific DNA binding, and interaction with the transcription complex. It is believed that the coiled-coil motif is the strongest region of sequence conservation in this region of the protein. These motifs are thought to mediate protein-protein interactions. Therefore, this motif is a logical candidate region to mediate one or more of these biochemical functions.

Examination of the clinical history of patient 120713 revealed four characteristics that may be caused by ERCC6 deficiency: (1) This patient has a history of colon cancer at age 48, without the polyposis of APC or MUTYH diseases or the microsatellite instability or mismatch repair protein expression abnormalities of Lynch. Somatic ERCC6 gene mutations have recently been found in genome-wide sequencing studies in 6% of CRCs (Wood L D et al. (2007) Science 318:1108-13; and Network CGA. (2012) Nature 487:330-7). This frequency was notable, but did not reach statistical significance, and ERCC6 was not classified as a 'driver'. It is believed that ERCC6 may contribute to the development of both sporadic CRC and FCRC. (2) The patient developed basal cell carcinoma (BCC) at the unusually early age of 23. The patient's brother developed BCC at age 50 and both the patient's mother and father had multiple BCCs in their 40 s. Although Cockayne Syndrome patients do not develop BCC, their cells are particularly sensitive to UV light; BCC is believed to be a highly UV-driven tumor. Moreover, mice with inherited ERCC6 mutations are prone to UV-induced skin tumors. (3) The patient developed macular degeneration (MD) at an unusually early age (in her 40's). A sequence polymorphism in ERCC6 has been linked to MD, although this association was not confirmed in two follow-up studies. (4) The patient's father developed bladder carcinoma at age 62. Somatic ERCC6 mutations have recently been reported in some bladder cancers in Southeast Asia. Thus, there are potential links to ERCC6 dysfunction in the patient's history of colon cancer, BCC, MD, and family history of bladder cancer. These observations are suggestive of an inherited constitutional predisposition to cancer and degenerative disease with features of ERCC6 dysfunction.

WRN is a helicase that plays an important role in DNA repair, although the mechanisms of repair remain under active investigation. Mutations in WRN cause Werner's syndrome, a growth disorder associated with features of premature aging. Regions of the protein that help form the helicase domain have been mapped. The variant in the Werner protein from patient 120713 is T705I. This variant is within the helicase domain, and was predicted by the PolyPhen2 program to be probably damaging, with a high confidence score (>0.9). The WRN variant from patient 118294 is 51292Y. This variant was scored by the PP2 program as being possibly damaging.

TERT is required to maintain telomeres at chromosome ends, thereby preventing them from causing chromosomal rearrangements and being recognized as damaged DNA. TERT mutations cause progressive diseases including a plastic anemia and pulmonary fibrosis. Progress has been made in identifying regions of TERT that contribute to its RNA-directed DNA polymerase activity and its interaction with protein partners. The TERT variant from patient 118294 is G198R. It was predicted by PolyPehn2 to be possibly damaging.

The ERCC6 N180Y, WRN T705I, TERT G198R, and FAAP100 S466L (see more below) variants were each confirmed by direct polymerase chain reaction (PCR) amplification of patient DNA and Sanger DNA sequencing (FIG. 5). The other potential variants were excluded on the basis of sequence changes that were either common (e.g., >1/1000) in SNP databases and/or predicted to represent benign changes in the encoded proteins.

This analysis of variants was repeated more rigorously by identifying all genes in Gene Ontology (GO) consortium databases to be associated with the terms DNA replication, DNA repair, checkpoint, mitosis, or mitotic. Thirty four variants in patient 118294 and nineteen variants in patient 120713 were associated with these GO terms. These variants were loaded into the PP2 program by batch methods; analysis was by a somewhat more stringent version of the program. Variants were then excluded that were present at a frequency less than 20% in the exome sequencing reads (and, therefore, unreliably constitutional), present in the NHLBI SNP databases at frequencies >1/1000, or predicted to likely be benign by the PP2 program.

ERCC6 N180Y and WRN T7051 were again the two leading candidate variants that emerged from this analysis, with PP2 scores >0.99. A new top-tier candidate variant emerged from this analysis: FAAP100/C17Orf70 S466L, with a PP@ score >0.98. Te FAAP100 protein was recently identified as an essential component of the Fanconi's Anemia DNA repair pathway (see below). Additional candidates emerged from this analysis which were designated as 'second tier' because they manifested higher SNP frequencies, lower PP2 scores, and/or carried less evidence for direct involvement in genome stability. From patient 120713: TRERF1, a transcription factor that may regulate the mitotic spindly checkpoint (1/13005 in SNP databases, PP2 score of 0.99); DYNC1H1, a protein implicated in mitotic spindle organization (not present in SNP databases, PP2 score 0.93 (probably damaging)); TRPM1, a transcription factor implicated in the DNA damage checkpoint (not present in SNP databases, PP2 score 0.90 (possibly damaging)), and SMC1B, a mediator of chromosomal condensation (not present in SNP databases, PP2 score possibly damaging).

The GO gene analysis from patient 118294 demoted the TERT variant to probably benign by PP2 analysis and yielded three new candidate variants: PTPRT, a protein tyrosine phosphatase that is mutated somatically in a fraction of CRCs (not present in SNP databases, probably damaging by PP2); TBRG4, protein that drives yeast cells into the cell cycle (5/13005 in SNP databases, probably damaging by PP2), and CDC14A, a phosphatase implicated in mitotic anaphase (not present in SNP databases, possibly damaging by PP2). Thus, none of the variants in patient 118294, including TERT, are believed to be top-tier.

Given that each of the second tier variants from patient 120713 and the CDC14 variant from patient 118294 has a direct or indirect role in regulating mitosis, the next stages of investigation will include an interrogation of the efficiency of mitosis in cells from each patient. Isolated cells will be infected with a retrovirus encoding a green fluorescent protein (GFP)-histone H2B fusion protein, and chromosome dynamics during mitosis will be observed in living cells. These experiments are somewhat technically challenging, given the small size of lymphocytes and the fact that they generally do not adhere to tissue culture dish bottoms, but preliminary experiments are underway.

In summary, eight independent FCRC cases were screened for constitutional genomic instability (CGI) by analyzing metaphase spreads and flow cytometry-generated cell cycle profiles of cultured peripheral lymphocytes. Two patients showed evidence of CGI in the form of aneuploidy (patient #120713), a chromosomal rearrangement (patient #118294), and/or increased fractions of cells within replicative phases (both patients). Exome sequencing revealed novel or rare heterozygous sequence variants in relevant genes. 120713 has a novel variant in ERCC6/CSB, a nucleotide excision repair gene. The variant is a strong candidate for being causal: it encodes a non-conservative change in a highly conserved residue in a region of the protein with biochemically-defined functions. The patient harboring this allele has three other clinical conditions consistent with ERCC6 dysfunction. Each patient also has a rare sequence variant in WRN, a DNA repair helicase. 120713 also carries a rare sequence variant in FAAP100, a scaffolding protein of the Fanconi's anemia DNA repair pathway. These observations provide evidence that ERCC6 and possibly WRN contribute to CGI and colon cancer in these FCRC cases.

EXAMPLE 2

Follow Up Studies

The studies described in Example 1 suggest that constitutional genomic instability is more widespread than currently recognized. It is believed that heterozygous mutations will be functionally important, due to haplo-insufficiency and/or dominant negative effects. Currently recognized FCRC syndromes are autosomal dominant at the organismic level, but are thought to be largely recessive at the cellular level. The following describes additional experiments to be undertaken.

Studies will evaluate whether the sequence variants of the ERCC6, WRN, TERT, and FAAP100 genes described in this specification inactivate the function of the proteins they encode. It is believed that dysfunction of genes that maintain genome stability underlies a substantial fraction of FCRC. These studies will proceed along the following basic outline: (1) Test whether the sequence variants inactivate protein function by (a) introducing the sequence variants into expression vectors by site-directed mutagenesis, (b) testing whether the variant proteins fail to rescue cellular deficiencies in the respective proteins, and (c) testing whether the variant proteins exert dominant negative effects; (2) Further define the nature and severity of CGI in the FCRC patients by (a) repeating metaphase spread and flow cytometry assays on primary cells, (b) performing assays for activation of the DNA damage response on primary cells, (c) establishing immortalized lymphocytes from the patients and assess their expression of the variant proteins and CGI, (d) testing whether patient cells are hypersensitive to exogenous DNA damage, and (e) test whether cell phenotypes can be rescued by exogenous expression of candidate genes; and, (3) Screen 30 additional FCRC patients for CGI and relevant sequence variants by (a) examining metaphase spreads, cell cycle profiles, and DNA damage foci in peripheral lymphocytes, and (b) perform exome sequencing in patients with evidence for CGI.

It is believed that these studies will provide new molecular insights into causes of FCRC and CGI and functional elements of DNA repair proteins while offering new methods to screen for predisposition to colon cancer and to diagnose affected members of FCRC families in pre-clinical stages. This capability should allow intensive colon cancer screening by endoscopy to be focused on those patients who should benefit strongly and to be avoided in those who will not. Related clinical conditions, such as predisposition to basal cell carcinoma, macular degeneration, and bladder cancer, may also be better managed.

(1) Testing Whether the Sequence Variants Inactivate Protein Function.
(a) Introduce the Sequence Variants into Expression Vectors by Site-Directed Mutagenesis.

The investigation will begin with introducing the sequence variants into expression vectors encoding the wild type proteins. The vectors have already been prepared, and expression experiments are underway.

(b) Test Whether the Variant Proteins Fail to Rescue Cellular Deficiencies in the Respective Proteins.

ERCC6 deficient cells have been established from patients with Cockayne's syndrome and are being maintained in culture. These cells are sensitive to UV treatment, consistent with the known role of ERCC6 in DNA repair. This phenotype can be rescued by expression of the wild type protein, providing a convenient assay system for protein function. As an initial test of ERCC6 function, the wild type and variant protein from patient 120713 will be expressed in parallel in the cognate deficient cells, and these proteins will be assayed to determine whether the variant fails to restore resistance to UV irradiation. The ability of ERCC6 to complement UV sensitivity likely integrates several biochemical activities of the protein and provides a good screen for functionally important defects. To further define the molecular defect, the wild type and variant proteins will be expressed in mammalian cells, and nuclear extracts will be prepared from these cells. These extracts will then be incubated with chromatin prepared from untreated or UV-irradiated cells. The UV-induced chromatin binding of the proteins will be compared. The protein will also be expressed in bacteria with an epitope tag, and the purified protein will be assayed for ATPase activity on DNA templates. Additional experiments may be suggested by these assays. These biochemical assays might also reveal a defect that failed to be detected during overexpression of the protein in the assays of UV sensitivity.

WRN-deficient cells have been established from patients with Werner's syndrome and are being maintained in culture. However, the most straightforward test of WRN function is to test its helicase activity, the activity central to WRN function in DNA repair. This activity is most readily tested by purifying the protein from bacterial extracts and incubating it with short double-stranded oligonucleotides with single-stranded 5' ends. WRN will unwind these templates, an activity readily detected by a shift in mobility on non-denaturing gel electrophoresis. The activities of wild type and variant WRN protein will be tested in this assay.

Most primary cells are TERT-deficient and can be infected with the retroviral vector. The wild type and variant TERT protein will be expressed in parallel, and telomerase activity will be evaluated in vitro using a standard assay.

FAAP100 acts as a scaffold upon which BRCA1 and other DNA repair proteins concentrate at lesions, to activate Chk1 and degrade Ccdc25A, among other functions. We will compare the ability of wild type and variant FAAP100 proteins to perform these actions.

(c) Test Whether the Variant Proteins Exert Dominant Negative Effects.

Defective proteins that occupy limited sites where the protein must normally act can exert dominant negative effects. It is believed that in some cases, expression of a defective protein disrupts function of the remaining wild type protein. Such sites may be homo- or hetero-multimeric complexes involving the protein. There is some evidence that ERCC6 multimerizes. This is also true for WRN. TERT must function as a complex with a small RNA that templates synthesis of telomeric DNA. In addition, TERT interacts with a small set of proteins that protect telomeres from recognition by the DNA damage pathway. As a scaffolding protein, FAAP100 may sequester other proteins involved in DNA damage responses, including DNA repair and cell cycle arrest.

These experiments will test whether expression of the ERCC6 variant protein confers sensitivity to UV irradiation. The variant will be titrated in co-transfections with limiting amounts of vector that rescues UV sensitivity of Cockayne syndrome cells, and the extent to which expression of the variant restores sensitivity or is inert will be assessed.

As well, whether the WRN variant confers sensitivity to the topoisomerase I poison camptothecin will be investigated. WRN syndrome cells do not show increased sensitivity to UV, but demonstrate distinctly increased apoptosis during S phase following exposure to this drug. The detailed mechanism is unknown, but the drug is known to trap topo I on DNA and to involve inhibition of transcription during S phase. It is thought to potentially reflect an inability of the WRN helicase to resolve and repair collisions between RNA polymerase complexes and/or DNA polymerase complexes and protein-modified DNA, with resulting double strand DNA breaks. Camptothecin does of 20-50 nM cause S phase delay and a 5-6-fold increase in apoptosis of Werner cells.

It is believed that the ERCC6 N180Y variant will disrupt protein function, given the constellation of clinical findings in patient 120713 consistent with ERCC6 dysfunction, the evidence that the variant residue is likely damaging, and the critical roles played by amino-terminal region the protein. The variant is anticipated to help unravel the function of the central motif in this region, the coiled-coil domain motif.

For example, follow-up studies will compare intramolecular and extrinsic protein-protein interactions mediated by this domain and disrupted by the variant (e.g., with the carboxy-terminal protein and transcription complex, by 'pull-down' assays, etc.) and will test whether the variant exhibits the marked conformational change thought to occur with lesion-induced activation of ATPase activity. Most extant ERCC6 mutations in Cockayne's syndrome and engineered mutations compromise the ATPase activity of ERCC6.

Whether the variant may be haploinsufficient or dominant negative is more difficult to predict. It is evident that patient 120713 did not have full-blown Cockayne syndrome, so the variant does not entirely inactivate ERCC6 function. Cockayne syndrome carriers are heterozygous for ERCC6 mutations. There is some evidence for phenotypes in their cells, such as modest UV sensitivity, but little clinical data addressing relevant diseases. If the variant ablates inhibition of ATPase activity of the protein, it may bind more indiscriminately and remodel chromatin structure in deleterious ways. It may, thereby, potentially alter transcription and/or divert repair factors, exerting dominant negative effects not seen with standard Cockayne syndrome mutations that inactivate ATPase activity. This molecular mechanism provides a possible alternative explanation for potential dominant negative effects of the variant without compromise of an ERCC6 homopolymeric complex.

It is believed that the WRN variant in patient 120713 will also inactivate protein function, and is predicted to be probably damaging. This variant may therefore compromise DNA repair is a second way in patient 120713, with additive or synergistic effects. Neoplasia is present in both maternal and paternal lineages of the patient, suggesting that there may be independent gene variants that predispose to neoplasia in the pedigree. However, if cell lines may be established, they will be tested for whether they exhibit major ongoing genetic instability and whether complementation with wild type ERCC6, WRN, or both are needed to restore genome stability.

(2) Further Examining Cells for Evidence of CGI.

The presence of 4 chromosomal gains in 50 metaphase spreads (8%), from patient 120713 is unlikely to represent a chance occurrence in normal cells. This rate of gains greatly exceeds the published rate of gains seen in normal stimulated lymphocytes (mode 0.4%) and the rate observed in the rest of the case and control samples in this study (0.7%). Gains are considered more reliable than losses, as the latter are sometimes artifacts of chromosome spreading. However, gains in well-separated spreads such as these are typically not technical artifacts. The spreads were generated by an in-house Genomics Facility, which has extensive experience with this method and performs it routinely for clinical analysis. Nonetheless, these assays will be repeated on cell lines established from patient 120713 and controls, to further validate the CGI and more accurately determine its level.

Patient 118294 exhibited a complex chromosomal rearrangement. This event cannot be artifactual, as it must be formed within the cell and is a rare event in normal cells. However, it is desired to gauge more accurately the rate of such events in cells from this patient. This patient also demonstrated the highest S phase fraction of any sample tested. The difference (14% above the mean S phase fraction in control samples) is well beyond the normal technical variation in S phase fraction in such samples (ca. 2-3%).

Generation of metaphase spreads and flow cytometry cell cycle profiles is useful for screening patients for CGI. However, the nature and severity of CGI in such cells have not been fully defined. Most GI is associated with double strand DNA breaks. Low levels of such lesions are difficult to detect directly. Nonetheless, their presence can often be detected indirectly by detecting activation of the DNA damage response (DDR). This response involves the concentration of repair proteins around the lesions, forming what is termed DNA damage foci. These foci are commonly visualized by immunofluorescence. Markers of DDR will be tested to identify this response in patients 120713 and 118294, by immunofluorescence (IF; most sensitive), immunohistochemistry (IHC; readily performed in most clinical pathology labs), and immunoblotting (IB; most specific for histone variant γH2AX).

(a) Repeating Metaphase Spread and Flow Cytometry Assays on Excess Primary Cells.

These experiments will verify and better quantitate the rate of generation of chromosomal and cell cycle abnormalities in patients 118294 relative to controls. Cultured cells will be stimulated with PHA. Some will then be treated with the mitotic spindle poison colchicine, permeabilized, dropped onto slides to generate spreads, and stained with Giemsa, to stain chromosomal bands and allow identification of individual chromosomes. At least 50 well-separated chromosome spreads per patient will be scored for aneuploidy and chromosomal rearrangements in triplicate. A portion of each PHA-stimulated culture (at least 100,00 cells) will be fixed in ethanol, stained with propidium iodide, and analyzed by flow cytometry, for DNA content in triplicate. The fraction of cells with S and G2/M phases, respectively, will be compared.

(b) Establishing Immortalized Lymphocytes from the Patients and CGI Assays.

A retroviral TERT vector has been transfected into a packaging cell line, and high titer viral supernatants have been generated. These will be used to infect control cells, to verify the method, and then samples from 120713 and 118294 will be used. T lymphocyte growth will be fostered by addition of IL-2. These polyclonal cultures will be expanded and aliquots frozen in DMSO. Other portions will be used to repeat the metaphase spread and flow cytometry analyses. Finally, a portion of each PHA-stimulate primary cell culture will be infected with retrovirus expressing SV40 large T antigen. These polyclonal cultures will be expanded and frozen in DMSO. In addition, we are preparing Epstein Barr Virus-transformed B lymphocyte cell lines form patient 120713 and controls.

(c) Performing Assays for DNA Damage Markers.

Primary cells, if available, or immortalized cells will be pelleted by low-speed centrifugation, embedded in histogel, fixed in paraformaldehyde (PFA) or formaldehyde, respectively, and sectioned as per a tissue block. The PFA-fixed material will be subjected to IF for DDR markers. The formalin-fixed material will be subjected to immunohistochemistry for DDR markers. Protein extracts will be prepared from other cells and subjected to immunoblotting for γH2AX. DNA will be damaged in samples of normal cells, as positive controls, using UV- and X-irradiation and treatment with camptothecin.

Given that there is a TERT gene variant in patient 118294, and defective telomerase activity has been linked to ds DNA breaks and genomic instability as well as intestinal tumorigenesis, telomere integrity will be evaluated in this patient. Telomere length will be estimated by in situ hybridization using a probe complementary to the TERT repeat and high-resolution fluorescence microscopy. Telomere-associated DNA damage foci will be assayed in cells fixed with paraformaldehyde by co-immunofluorescence for the telomere protein TRAP1 or TRF1 and DNA damage response markers γH2AX and 53BP1.

(d) Testing Whether Patient Cells are Hypersensitive to Exogenous DNA Damage.

Cockayne syndrome patients and their cells are hypersensitive to UV-irradiation. Patient 120713 has a personal and family history of basal cell carcinoma, a UV-associated tumor, and a history of macular degeneration, thought to be in part a UV-driven disease. Exogenous damage may elicit a sensitivity that is less apparent in un-treated cells. Cells will be exposed to 4 J/m2 joules of UV-irradiation from a UV lamp and examined for DDR foci. Cells will also be assayed for their long-term proliferative capacity by the colony-outgrowth assay. Similar assays will be performed following X-irradiation and treatment with cisplatin, respectively, as controls for more general defects in cells from patient 120713 and to detect other potential defects in DNA repair and/or the DDR in patient 118294.

(e) Testing Whether Cell Phenotypes can be Rescued by Exogenous Expression of Candidate Genes.

Whether observed patient cell phenotypes of GI, UV sensitivity, camptothecin sensitivity, and telomeric DNA damage foci can be rescued by overexpression of the respective wild types proteins will be tested. It is believed that the repeat assays of CGI will confirm it in the patients and help determine its severity. The results will also clarify whether the CGI differs qualitatively in the two patients. For example, it will be determined whether or not the CGI in patient 120713 primarily causes aneuploidy, without chromosomal rearrangement and whether or not the reverse is true to patient 118194. Although ERCC6 has primarily been implicated in nucleotide excision repair of bulky lesions, which do not necessarily form double strand DNA breaks, bulky lesions or their partially repaired intermediates are thought to often be converted to ds breaks when encountered by replication forks. In addition, ERCC6 has been implicated to lesser degrees in other forms of DNA repair, including homologous recombination, a favored route for repair of ds breaks. It is believed that cells from patient 120713 will be hypersensitive to UV-irradiation. In this case, whether this phenotype can be rescued by overexpression of ERCC6 wild-type more effectively than the variant allele will be investigated. If the WNR allele from this patient also appears to be defective, whether exogenous WRN expression can reduce sensitivity will be investigated.

(3) Screen 30 Additional FCC Patients for CGI and Sequence Variants in Related Genes.

These proposed studies will triple the previous patient set and allow for the setting of initial bounds on the frequency of CGI in FCC patients. In addition, candidate genes responsible for the observed CGI have been identified. At this point, each represents a sample size of one. Examination of additional patients will provide for a determination of whether the responsible gene set is small or large. If the current experience can be extrapolated to the additional 30 patients, it is anticipated that more patients with CGI will be identified. These data can be used subsequently to design larger clinical studies to more accurately assess the frequency of involved genes and to assess the practicality of determining the underlying lesions by targeted sequencing of candidate genes, rather than exome sequencing.

EXAMPLE 3

FAAP100 S466L

An additional candidate disease-causing variant in patient 120713 was identified. To systematically analyze the list of gene variants derived from the exome sequencing results, Gene Ontology (GO) consortium databases were used to focus on variant genes associated with the terms DNA replication, DNA repair, checkpoint, mitosis, or mitotic. Thirty four variants in patient 118294 and 19 variants in patient 120713 were associated. Variants were identified that represented >40% of the sequencing reads (and were, therefore, likely to be at least heterozygous), absent from NHLBI SNP databases or present at frequencies <1/1000 (thereby reducing type 1 errors), and predicted by the PolyPhen2 program (Sunyaev, Harvard University) to be probably damaging to protein function. A few were excluded that appeared to not be directed related to CGI, on the basis of being expressed primarily outside the nucleus and/or in a severely restricted tissue pattern. From this analysis, patient 118294 did not yield a strong candidate variant. However, 3 good candidate missense variants were found in patient 120713. In addition to the previously recognized variants ERCC6/CSB N180Y and WRN T705I, C17ORf70/FAAP100 S466L was identified as a strong candidate disease-causing variant.

FAAP100 is an understudied but essential component of the Fanconi's anemia (FA) DNA repair complex. FA is a rare recessive syndrome associated with bone marrow failure, genetic instability, and cancer. It involves a failure to prevent DNA double strand (ds) breaks during DNA replication. FA cells fail to mono-ubiquitinate FANCD2, the central outcome of the pathway, and are very sensitive to DNA cross-linking agents such as mitomycin C. It has recently been established that FANCD is the breast and ovarian cancer tumor suppressor BRCA2, and the complex interacts with BRCA1. FAAP100 acts as a scaffolding protein for the ubiquitin ligase FANCL, but has few defined motifs, and its functional elements have not been mapped. This gene is a potential link to the history of two paternal cousins with early onset breast and ovarian cancers, respectively. If the heterozygous variant compromises the FA pathway, this variant could account for or help account for the patient's apparent defective DNA repair (see next advance), genetic instability, and predisposition to colon cancer.

The FAAP100 variant represents a C to T change (G to A on the opposite strand) at nucleotide 1443 of accession number BC117141 (SEQ ID NO:22). This nucleotide is at position 77124711 on human chromosome 17. The change results in substitution of leucine for serine at amino acid 466 of the protein (SEQ ID NO:23). This substitution is predicted by the PolyPhen2 program to be probably damaging to protein function with high confidence (0.98 score out of 1.00).

EXAMPLE 4

Increase in Double Stranded Breaks and Gamma-H2AX Foci

Figure 6:
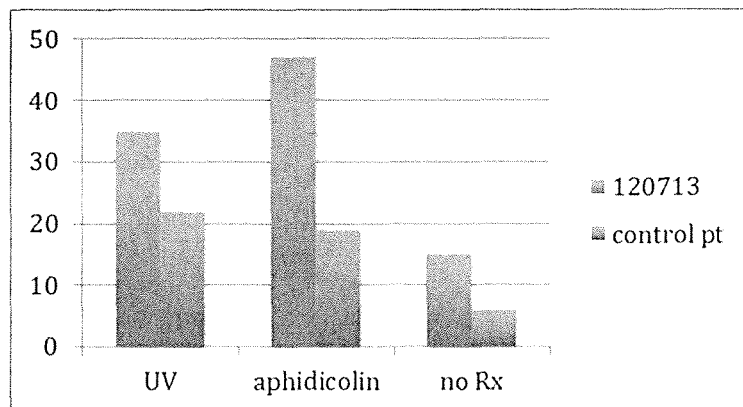
FIG. 6 shows greater DDR foci in patient 120713 than its control. Lymphocytes were treated with 4 J/m² UV or 3 µM aphidicolin for 2 h and fixed 5 h (UV) or 1 h later (aph). γH2AX IF foci were scored in blinded fashion. Results shown are the percent of cells (y-axis) with ≥10 nuclear foci (total of 1,117 cells scored). Insert: 120713 cell foci after UV. Comparison with (no) Rx: P=0.08.

It was determined that patient 120713 exhibited an exaggerated response to DNA damage, likely reflecting increased double stranded (ds) DNA breaks. Ds breaks are thought to be a major cause of instability of chromosome structure. The ds break also serves as a nidus for detection of DNA damage responses (DDRs) to a variety of damage, including bulky DNA adducts, intra- and inter-strand cross-links, and collapse of replication forks. Recent data suggest that many ds breaks are formed by replicative events, such as reverse branch migration of Holiday junctions when movement of the DNA replication fork is impaired. Thus, many repair events can result in a ds break. At such breaks, the alternate histone H2AX undergoes extensive phosphorylation, forming 'γH2AX' foci visible by immunofluorescence (IF). Other DDR proteins such as phosphorylated ATM/ATR and 53BP1 are recruited into such foci. During work for the project, an in-house Cell Culture Facility worked out conditions under which IL-2, anti-T-cell receptor, and anti-CD3 antibodies stimulate robust growth of primary T-lymphocytes from peripheral blood lymphocytes. In preliminary studies, lymphocytes were treated with ultraviolet light (UV) or the DNA polymerase inhibitor aphidicolin. Aphidicolin is commonly used to reveal DNA repair defects. It generates replicative stress, with collapse of stalled replication forks and generation of ds breaks. The cells were then allowed to adhere to poly-lysine-coated slides, fixed with paraformaldehyde, and stained for γH2AX. Flow cytometry confirmed equivalent fractions of replicating cells in patient 120713 and the control. It was observed that cells from patient 120713 showed substantially greater γH2AX foci in response to treatment with UV or aphidicolin when compared to its age- and sex-matched normal control (FIG. 6; each P<0.001, by Fisher's exact test).

Figure 7:
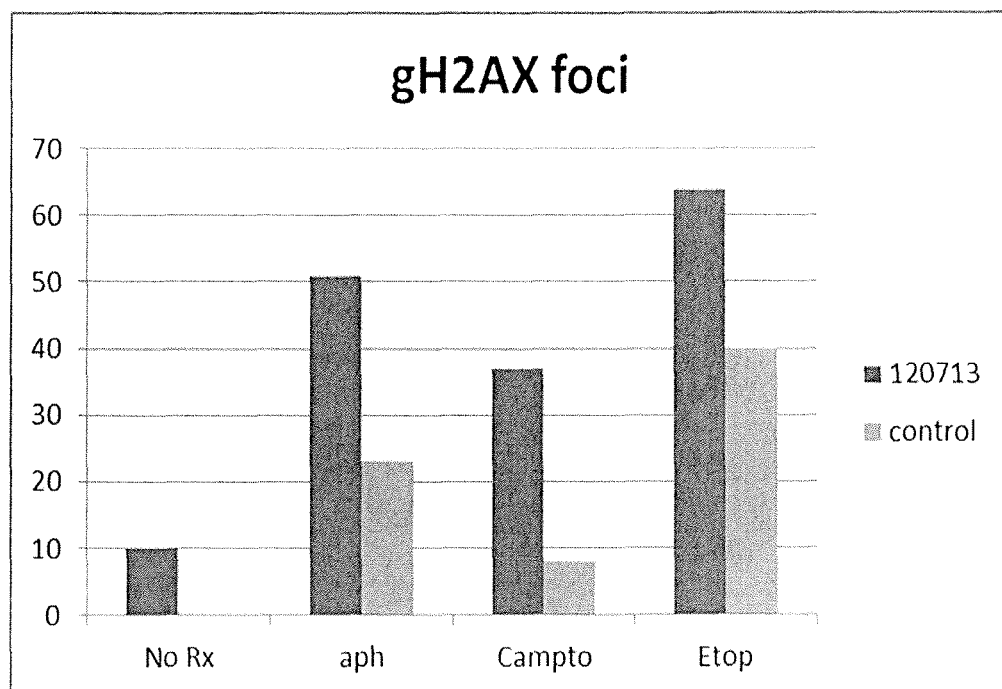
FIG. 7 shows greater gamma-H2AX foci in lymphocytes from patient 120713 than the control in another experiment. The foci are higher at the baseline (no Rx), as well as in response to amphidicolin, camptothecin, and etopside treatments.

Additional data showed further evidence of a greater DNA damage response, marked by gamma-H2AX foci scored in a blinded fashion, from patient 120713 (FIG. 7). The data show ongoing DNA damage response at the baseline in the patient's lymphocytes (No Rx), as well as in response to treatment with aphidicolin (aph), camptothecin (Campto), and etoposide (Etop). The graph shows that the levels of gamma-H2AX foci are higher in patient 120713 (dark grey) relative to a control subject (light grey).

These findings provide further evidence for a DNA repair defect in patient 120713. Moreover, they offer the prospect that assaying the DDR in normal lymphocytes from at-risk individuals may help identify those with a predisposition to colon cancer. This assay might take the form of immunofluorescence staining for γH2AX, as shown here, or immunohistochemistry, immunoblotting, enzyme-linked immunosorbant assays (ELISAs), or flow cytometry.

The invention is not limited to the embodiments described and exemplified above, but is capable of variation and modification within the scope of the appended claims.

We claim:

1. A system for diagnosing a predisposition to develop cancer, comprising
    an immunoblotting support, an immunofluorescence support, an immunohistochemistry support, an ELISA support, or a flow cytometry support comprising peripheral blood lymphocytes obtained from a human subject and permeabilized, a detectably-labeled antibody that specifically binds to gamma-H2AX foci, and a detector capable of detecting the detectably-labeled antibody bound to gamma-H2AX foci in the lymphocytes and of quantifying the level of gamma-H2AX foci in the lymphocytes based on detection of the detectably-labeled antibody;
    a metaphase spread or a karyotype obtained from the lymphocytes, and a detector capable of detecting the absence or presence and type of genomic instability from the metaphase spread or karyotype;
    a computer comprising an input for entering the level of gamma-H2AX foci in the lymphocytes and the type of genomic instability in the lymphocytes, a data structure comprising reference values for a level of gamma-H2AX foci and a type of genomic instability that together indicate a predisposition to develop colon cancer, a processor operably connected to the data structure, wherein the processor is programmed to compare the level of gamma-H2AX foci and type of genomic instability detected in the lymphocytes with the reference values and generate a diagnosis of whether the subject has or does not have a predisposition to develop colon cancer based on the comparison of the level of gamma-H2AX foci in the lymphocytes and the type of genomic instability in the lymphocytes with the reference values, and an output for providing the diagnosis to a user.

2. The system of claim 1, wherein the system further comprises one or more nucleic acids obtained from the lymphocytes, said nucleic acids, respectively, encoding the Cockayne Syndrome B protein, the Werner protein, Telomerase Reverse Transcriptase, or the Fanconi anemia-associated protein, and a nucleic acid sequencer capable of determining the sequence of the one or more nucleic acids;
    wherein the data structure further comprises one or more reference nucleic acid sequences encoding a tyrosine at position 180 of the Cockayne Syndrome B protein, one or more reference nucleic acid sequences encoding an isoleucine at position 705 of the Cockayne Syndrome B protein, one or more reference nucleic acid sequences encoding a tyrosine at position 1292 of the Werner protein, one or more reference nucleic acid sequences encoding an arginine at position 198 of the Telomerase Reverse Transcriptase protein, and one or more reference nucleic acid sequences encoding a leucine at position 466 of the Fanconi anemia-associated protein, and optionally further comprises one or more reference nucleic acid sequences that do not encode a tyrosine at position 180 of the Cockayne Syndrome B protein, one or more reference nucleic acid sequences that do not encode an isoleucine at position 705 of the Werner protein, one or more reference nucleic acid sequences that do not encode a tyrosine at position 1292 of the Werner protein, one or more reference nucleic acid sequences that do not encode an arginine at position 198 of the Telomerase Reverse Transcriptase protein, and one or more reference nucleic acid sequences that do not encode a leucine at position 466 of the Fanconi anemia-associated protein, and the processor is programmed to compare the sequence of a nucleic acid encoding the Cockayne Syndrome B protein, a nucleic acid encoding the Werner protein, a nucleic acid encoding the Telomerase Reverse Transcriptase protein, and a nucleic acid encoding the Fanconi anemia-associated protein determined from a nucleic acid isolated from a subject with the one or more reference nucleic acid sequences encoding an isoleucine at position 705 of the Werner protein, one or more reference nucleic acid sequences encoding a tyrosine at position 1292 of the Werner protein, one or more reference nucleic acid sequences encoding an arginine at position 198 of the Telomerase Reverse Transcriptase protein, one or more reference nucleic acid sequences encoding a leucine at position 466 of the Fanconi anemia-associated protein, one or more reference nucleic acid sequences that do not encode a tyrosine at position 180 of the Cockayne Syndrome B protein, one or more reference nucleic acid sequences that do not encode an isoleucine at position 705 of the Werner protein, one or more reference nucleic acid sequences that do not encode a tyrosine at position 1292 of the Werner protein, one or more reference nucleic acid sequences that do not encode an arginine at position 198 of the Telomerase Reverse Transcriptase protein, and one or more reference nucleic acid sequences that do not encode a leucine at position 466 of the Fanconi anemia-associated protein, and wherein the processor is further programmed to compare the determined sequence of the one or more nucleic acids with the one or more reference nucleic acid sequences and generate a diagnosis of whether the subject has or does not have a predisposition to develop colon cancer based on the comparison of the determined sequence of the one or more nucleic acids with said reference nucleic acids and the comparison of the level of gamma-H2AX foci in the lymphocytes and the type of genomic instability in the lymphocytes with the reference values for a level of gamma-H2AX foci and a type of genomic instability that indicate a predisposition to develop colon cancer.

3. The system of claim 1, wherein the type of genomic instability is chromosomal aneuploidy.

4. The system of claim 1, further comprising a computer network connection.

5. The system of claim 3, wherein the chromosomal aneuploidy is gain of chromosome 9 or a gain of chromosome 11.

6. The system of claim 1, wherein the system further comprises a detectably-labeled antibody that specifically binds to the ataxia telangiectasia mutated (ATM) protein, wherein the detector is further capable of detecting the detectably-labeled antibody bound to the ATM protein in the lymphocytes and quantifying the level of ATM protein in the lymphocytes based on detection of the detectably-labeled antibody bound to the ATM protein, wherein the data structure further comprises reference values for a level of ATM protein that, together with the reference values for a level of gamma-H2AX foci and a type of genomic instability, indicate a predisposition to develop colon cancer, and wherein the processor is further programmed to compare the level of ATM protein detected in the lymphocytes with said reference values for a level of ATM protein, and generate a diagnosis of whether the subject has or does not have a predisposition to develop colon cancer based on the comparison of the level of ATM protein with said reference values for a level of ATM protein and the comparison of the level of gamma-H2AX foci in the lymphocytes and the type of genomic instability in the lymphocytes with the reference values for a level of gamma-H2AX foci and a type of genomic instability that indicate a predisposition to develop colon cancer.

7. The system of claim 1, wherein the system further comprises a detectably-labeled antibody that specifically binds to the ataxia telangiectasia and Rad3-related (ATR) protein, wherein the detector is further capable of detecting the detectably-labeled antibody bound to the ATR protein in the lymphocytes and quantifying the level of ATR protein in the lymphocytes based on detection of the detectably-labeled antibody bound to the ATR protein, wherein the data structure further comprises reference values for a level of ATR protein that, together with the reference values for a level of gamma-H2AX foci and a type of genomic instability, indicate a predisposition to develop colon cancer, and wherein the processor is further programmed to compare the level of ATR protein detected in the lymphocytes with said reference values for a level of ATR protein, and generate a diagnosis of whether the subject has or does not have a predisposition to develop colon cancer based on the comparison of the level of ATR protein with said reference values for a level of ATR protein and the comparison of the level of gamma-H2AX foci in the lymphocytes and the type of genomic instability in the lymphocytes with the reference values for a level of gamma-H2AX foci and a type of genomic instability that indicate a predisposition to develop colon cancer.

8. The system of claim 1, wherein the system further comprises a detectably-labeled antibody that specifically binds to the tumor suppressor p53-binding protein 1 (53BP1), wherein the detector is further capable of detecting the detectably-labeled antibody bound to the 53BP1 in the lymphocytes and quantifying the level of 53BP1 in the lymphocytes based on detection of the detectably-labeled antibody bound to 53BP1, wherein the data structure further comprises reference values for a level of 53BP1 that, together with the reference values for a level of gamma-H2AX foci and a type of genomic instability, indicate a predisposition to develop colon cancer, and wherein the processor is further programmed to compare the level of 53BP1 detected in the lymphocytes with said reference values for a level of 53BP1, and generate a diagnosis of whether the subject has or does not have a predisposition to develop colon cancer based on the comparison of the level of 53BP1 with said reference values for a level of 53BP1 and the comparison of the level of gamma-H2AX foci in the lymphocytes and the type of genomic instability in the lymphocytes with the reference values for a level of gamma-H2AX foci and a type of genomic instability that indicate a predisposition to develop colon cancer.

* * * * *

UNITED STATES PATENT AND TRADEMARK OFFICE
CERTIFICATE OF CORRECTION

PATENT NO. : 9,157,124 B2  
APPLICATION NO. : 13/833946  
DATED : October 13, 2015  
INVENTOR(S) : Enders et al.

Page 1 of 1

It is certified that error appears in the above-identified patent and that said Letters Patent is hereby corrected as shown below:

Title Page, Item (72) Inventor is corrected to read:
-- Greg H. Enders, Villanova (PA);
Mark Andrake, Huntingdon Valley (PA);
Michael J. Hall, Glenside (PA);
Biao Luo, Princeton (NJ);
Timothy J. Yen, Haverford (PA);
Sanjeevani Arora, Philadelphia (PA) --.

Signed and Sealed this  
Twenty-first Day of June, 2016

Michelle K. Lee  
*Director of the United States Patent and Trademark Office*

SEQUENCE LISTING

<160> NUMBER OF SEQ ID NOS: 24

<210> SEQ ID NO 1
<211> LENGTH: 4479
<212> TYPE: DNA
<213> ORGANISM: Homo sapiens

<400> SEQUENCE: 1

```
atgccaaatg agggaatccc ccactcaagt caaactcagg agcaagactg tttacagagt      60
caacctgtca gtaataatga agaaatggca atcaagcaag aaagtggtgg tgatggggag     120
gtggaggagt acctctcctt tcgttctgtg ggtgacgggc tgtccacctc tgctgtgggg     180
tgcgcatcag cagctccgag gagagggcca gccctgctgc acatcgaccg acatcagatc     240
caggcagtag agcctagcgc ccaggccctt gagctgcagg gtttgggtgt ggacgtctat     300
gaccaggacg tgctggaaca gggagtgctt cagcaggtgg acaatgccat ccatgaggcc     360
agccgtgcct cccagctcgt tgacgtggag aaggagtatc ggtcggtcct ggatgacctc     420
acgtcatgta cgacatccct aaggcaaatc aataaaatta ttgaacagct tagccctcaa     480
gctgccacca gcagagacat caacaggaaa ctagattctg taaaacgaca gaagtattat     540
aaggaacaac agctaaaaaa gatcactgca aaacaaaagc atctccaggc catccttgga     600
ggagcagagg tgaaaattga actagatcac gccagtctgg aggaggatgc agagccgggg     660
ccatccagtc ttggcagcat gctcatgcct gtccaggaga ctgcctggga agagctcatc     720
cgcactggcc agatgacacc ttttggtacc cagatccctc agaaacagga gaaaaagccc     780
agaaaaatca tgcttaatga agcatcaggc ttcgaaaagt atttggcaga tcaagcaaaa     840
ctgtcttttg aaaggaagaa gcaaggttgt aataaaagag cagctagaaa agctccagcc     900
ccagtcacgc ctccagcccc agtgcaaaat aaaaacaaac caaacaagaa agccagagtt     960
ctgtccaaaa aagaggagcg tttgaaaaag cacatcaaga aactccagaa gagggctttg    1020
cagttccagg ggaaagtggg attgccaaag gcaaggagac cttgggagtc agacatgagg    1080
ccagaggcag agggagactc tgagggtgaa gagtctgagt atttccccac agaggaggag    1140
gaagaggagg aagatgacga ggtggagggg gcagaggcgg acctgtctgg agatggtact    1200
gactatgagc tgaagcctct gcccaagggc gggaaacggc agaagaaagt gccagtgcag    1260
gagattgatg atgactttttt cccaagttct ggggaagaag ctgaagctgc ttctgtagga    1320
gaaggaggag gaggaggtcg gaaagtggga agataccgag atgatggaga tgaagattat    1380
tataagcagc ggttaaggag atggaataaa ctgagactgc aggacaaaga gaacgtctg     1440 aagctggagg acgattctga ggaaagtgat gctgaattttg acgaaggttt taaagtgcca    1500
```

```
ggttttctgt tcaaaaagct ttttaagtac cagcagacag gtgttaggtg gctgtgggaa    1560
ttgcactgcc agcaggcagg aggaattctg ggagatgaaa tgggattggg caagaccatc    1620
cagataattg ccttcttggc aggtctgagc tacagcaaga tcaggactcg tggttcaaat    1680
tacaggtttg aggggttggg tccaactgta attgtctgtc caacaacagt gatgcatcag    1740
tgggtgaagg aatttcacac gtggtggcct ccgttcagag tggcaattct acatgaaacc    1800
ggttcctata cccacaaaaa ggagaaacta attcgagatg ttgctcattg tcatggaatt    1860
ttgatcacat cttactccta cattcgattg atgcaggatg acattagcag gtatgactgg    1920
cactatgtga tcttggacga aggacacaaa attcgaaatc caaatgctgc tgtcacccett    1980 gcttgcaaac agtttcgcac ccctcatcgg atcattctgt ctggctcacc gatgcaaaat    2040
aacctccgag agctgtggtc gctctttgac ttcatcttcc cgggaaagtt aggcacgttg    2100
cctgtgttta tggagcagtt ctccgtcccc atcaccatgg ggggatattc aaatgcttcc    2160
ccagtacagg tcaaaactgc ttacaagtgt gcatgtgtct tacgagatac cataaatcca    2220
tacctactgc ggagaatgaa gtcagatgtc aagatgagcc tttctttgcc agataaaaat    2280
gaacaggtct tattttgccg tcttacagat gagcagcata agtctacca aaatttcgtt     2340 gattccaaag aagtttacag gattctcaat ggagagatgc agattttctc cggacttata    2400
gccctaagaa aaatttgcaa ccaccctgat ctcttttctg gaggtcccaa gaatctcaaa    2460
ggtcttcctg atgatgaact agaagaagat cagtttgggt actggaaacg ttctgggaaa    2520
atgattgttg ttgagtcttt gttgaaaata tggcacaagc agggtcagcg agtattgctg    2580
ttttctcagt caaggcagat gctggacata cttgaagtat tccttagagc ccaaaagtat    2640
acctatctca agatggatgg taccactaca atagcttcaa gacagccact gattacgaga    2700
tacaatgagg acacatccat atttgtgttt cttctgacca cgcgggtggg cggcttaggt    2760
gtcaacctga cggggggcaaa cagagttgtc atctatgacc cagactggaa cccaagcacg    2820
gacacgcagg cccgggagcg agcatggaga ataggccaga agaagcaagt gactgtgtac    2880
aggctcctga ctgcgggcac cattgaagaa aagatctacc accgacaaat cttcaagcag    2940
tttttgacaa atagagtgct aaaagaccca aaacaaaggc ggttttttcaa atccaatgat    3000 ctctatgagc tatttactct gactagtcct gatgcatccc agagcactga aacaagtgca    3060 attttttgcag gaactggatc agatgttcag acacccaaat gccatctaaa aagaaggatt    3120
caaccagcct ttggagcaga ccatgatgtt ccaaaacgca agaagttccc tgcttctaac    3180
atatctgtaa atgatgccac atcatctgaa gagaaatctg aggctaaagg agctgaagta    3240
aatgcagtaa cttctaatcg aagtgatcct ttgaaagatg acccctcacat gagtagtaat    3300 gtaactagca atgataggct tggagaagag acaaatgcag tatctggacc agaagagttg    3360
tcagtgatta gtggaaatgg ggaatgttca aattcttcag gaacaggcaa aacttctatg    3420
ccatctggtg atgaaagcat tgatgaaaag ttaggtcttt cttacaaaag agaaagaccc    3480
agccaggctc aaacagaagc ttttgggag aataaacaaa tggaaaataa ttttttataag    3540 cacaagtcaa aaacaaaaca tcatagtgtg gcagaagaag agaccctgga gaaacatctg    3600
agaccaaagc aaaagcctaa gaactctaag cattgcagag acgccaagtt tgaaggaact    3660
cgaattccac acctggtgaa gaaaaggcgt taccagaagc aagacagtga aaacaagagt    3720
gaggccaagg aacagagcaa tgacgattat gttttggaaa agcttttcaa aaaatcagtt    3780
ggcgtgcaca gtgtcatgaa gcacgatgcc atcatggatg gagccagccc agattatgta    3840
ctggtggagg cagaagccaa ccgagtggcc caggatgccc tgaaagcact gaggctctct    3900
```

```
cgtcagcggt gtctgggagc agtgtctggt gttcccacct ggactggcca caggggggatt    3960 tctggtgcac cagcaggaaa aaagagtaga tttggtaaga aaaggaattc taacttctct    4020
gtgcagcatc cttcatcaac atctccaaca gagaagtgcc aggatggcat catgaaaaag    4080
gagggaaaag ataatgtccc tgagcatttt agtggaagag cagaagatgc agactcttca    4140
tccgggcccc tcgcttcctc ctcactcttg gctaaaatga gagctagaaa ccacctgatt    4200
ctgccagagc gtttagaaag tgaaagcggg cacctgcagg aagcttctgc cctgctgccc    4260
accacagaac acgatgacct tctggtggag atgagaaact tcatcgcttt ccaggcccac    4320
actgatggcc aggccagcac cagggagata ctgcaggagt ttgaatccaa gttatctgca    4380
tcacagtctt gtgtcttccg agaactattg agaaatctgt gcactttcca tagaacttct    4440
ggtggtgaag gaatttggaa actcaagcca gaatactgc                           4479
```

<210> SEQ ID NO 2
<211> LENGTH: 4479
<212> TYPE: DNA
<213> ORGANISM: Homo sapiens

<400> SEQUENCE: 2

```
atgccaaatg agggaatccc ccactcaagt caaactcagg agcaagactg tttacagagt      60
caacctgtca gtaataatga agaaatggca atcaagcaag aaagtggtgg tgatggggag     120
gtggaggagt acctctcctt tcgttctgtg ggtgacgggc tgtccacctc tgctgtgggg     180
tgcgcatcag cagctccgag gagagggcca gccctgctgc acatcgaccg acatcagatc     240
caggcagtag agcctagcgc ccaggccctt gagctgcagg gtttgggtgt ggacgtctat     300
gaccaggacg tgctggaaca gggagtgctt cagcaggtgg acaatgccat ccatgaggcc     360
agccgtgcct cccagctcgt tgacgtggag aaggagtatc ggtcggtcct ggatgacctc     420
acgtcatgta cgacatccct aaggcaaatc aataaaatta ttgaacagct tagccctcaa     480
gctgccacca gcagagacat caacaggaaa ctagattctg taaaacgaca gaagtataat     540
aaggaacaac agctaaaaaa gatcactgca aaacaaaagc atctccaggc catccttgga     600
ggagcagagg tgaaaattga actagatcac gccagtctgg aggaggatgc agagccgggg     660
ccatccagtc ttggcagcat gctcatgcct gtccaggaga ctgcctggga agagctcatc     720
cgcactggcc agatgacacc tttggtacc cagatccctc agaaacagga gaaaagccc      780 agaaaaatca tgcttaatga agcatcaggc ttcgaaaagt atttggcaga tcaagcaaaa     840
ctgtcttttg aaaggaagaa gcaaggttgt aataaaagag cagctagaaa agctccagcc     900
ccagtcacgc ctccagcccc agtgcaaaat aaaaacaaac caaacaagaa agccagagtt     960
ctgtccaaaa aagaggagcg tttgaaaaag cacatcaaga aactccagaa gagggctttg    1020
cagttccagg ggaaagtggg attgccaaag gcaaggagac cttgggagtc agacatgagg    1080
ccagaggcag agggagactc tgagggtgaa gagtctgagt atttccccac agaggaggag    1140
gaagaggagg aagatgacga ggtggagggg gcagaggcgg acctgtctgg agatggtact    1200
gactatgagc tgaagcctct gcccaagggc gggaaacggc agaagaaagt gccagtgcag    1260
gagattgatg atgactttt cccaagttct ggggaagaag ctgaagctgc ttctgtagga    1320
gaaggaggag gaggaggtcg gaaagtggga agataccgag atgatggaga tgaagattat    1380
tataagcagc ggttaaggag atggaataaa ctgagactgc aggacaaaga gaacgtctg    1440 aagctggagg acgattctga ggaaagtgat gctgaatttg acgaaggttt taagtgcca    1500
```

```
ggttttctgt tcaaaaagct ttttaagtac cagcagacag gtgttaggtg gctgtgggaa      1560
ttgcactgcc agcaggcagg aggaattctg ggagatgaaa tgggattggg caagaccatc      1620
cagataattg ccttcttggc aggtctgagc tacagcaaga tcaggactcg tggttcaaat      1680
tacaggtttg aggggttggg tccaactgta attgtctgtc caacaacagt gatgcatcag      1740
tgggtgaagg aatttcacac gtggtggcct ccgttcagag tggcaattct acatgaaacc      1800
ggttcctata cccacaaaaa ggagaaacta attcgagatg ttgctcattg tcatggaatt      1860
ttgatcacat cttactccta cattcgattg atgcaggatg acattagcag gtatgactgg      1920
cactatgtga tcttggacga aggacacaaa attcgaaatc caaatgctgc tgtcaccctt      1980
gcttgcaaac agtttcgcac ccctcatcgg atcattctgt ctggctcacc gatgcaaaat      2040
aacctccgag agctgtggtc gctctttgac ttcatcttcc cgggaaagtt aggcacgttg      2100
cctgtgttta tggagcagtt ctccgtcccc atcaccatgg ggggatattc aaatgcttcc      2160
ccagtacagg tcaaaactgc ttacaagtgt gcatgtgtct tacgagatac cataaatcca      2220
tacctactgc ggagaatgaa gtcagatgtc aagatgagcc tttctttgcc agataaaaat      2280
gaacaggtct tattttgccg tcttacagat gagcagcata agtctacca aaatttcgtt      2340 gattccaaag aagtttacag gattctcaat ggagagatgc agattttctc cggacttata      2400
gccctaagaa aaatttgcaa ccaccctgat ctcttttctg gaggtcccaa gaatctcaaa      2460
ggtcttcctg atgatgaact agaagaagat cagtttgggt actggaaacg ttctgggaaa      2520
atgattgttg ttgagtcttt gttgaaaata tggcacaagc agggtcagcg agtattgctg      2580
ttttctcagt caaggcagat gctggacata cttgaagtat tccttagagc ccaaaagtat      2640
acctatctca agatggatgg taccactaca atagcttcaa gacagccact gattacgaga      2700
tacaatgagg acacatccat atttgtgttt cttctgacca cgcgggtggg cggcttaggt      2760
gtcaacctga cgggggcaaa cagagttgtc atctatgacc cagactggaa cccaagcacg      2820
gacacgcagc cccgggagcg agcatggaga ataggccaga gaagcaagt gactgtgtac      2880 aggctcctga ctgcgggcac cattgaagaa aagatctacc accgacaaat cttcaagcag      2940
tttttgacaa atagagtgct aaaagaccca aaacaaaggc ggttttttcaa atccaatgat      3000 ctctatgagc tatttactct gactagtcct gatgcatccc agagcactga acaagtgca      3060 attttttgcag gaactggatc agatgttcag acacccaaat gccatctaaa agaaggatt      3120 caaccagcct ttggagcaga ccatgatgtt ccaaaacgca gaagttccc tgcttctaac      3180 atatctgtaa atgatgccac atcatctgaa gagaaatctg aggctaaagg agctgaagta      3240
aatgcagtaa cttctaatcg aagtgatcct ttgaaagatg acccctcacat gagtagtaat      3300 gtaactagca atgataggct tggagaagag acaaatgcag tatctggacc agaagagttg      3360
tcagtgatta gtggaaatgg ggaatgttca aattcttcag gaacaggcaa aacttctatg      3420
ccatctggtg atgaaagcat tgatgaaaag ttaggtcttt cttacaaaag agaaagaccc      3480
agccaggctc aaacagaagc ttttttgggag aataaacaaa tggaaaataa ttttttataag      3540 cacaagtcaa aaacaaaaca tcatagtgtg gcagaagaag agaccctgga gaaacatctg      3600
agaccaaagc aaaagcctaa gaactctaag cattgcagag cgccaagtt tgaaggaact      3660 cgaattccac acctggtgaa gaaaaggcgt taccagaagc aagacagtga aaacaagagt      3720
gaggccaagg aacagagcaa tgacgattat gttttggaaa agcttttcaa aaaatcagtt      3780
ggcgtgcaca gtgtcatgaa gcacgatgcc atcatggatg gagccagccc agattatgta      3840
ctggtggagg cagaagccaa ccgagtggcc caggatgccc tgaaagcact gaggctctct      3900
```

```
cgtcagcggt gtctgggagc agtgtctggt gttcccacct ggactgggca caggggatt    3960
tctggtgcac cagcaggaaa aaagagtaga tttggtaaga aaaggaattc taacttctct    4020
gtgcagcatc cttcatcaac atctccaaca gagaagtgcc aggatggcat catgaaaaag    4080
gagggaaaag ataatgtccc tgagcatttt agtggaagag cagaagatgc agactcttca    4140
tccgggcccc tcgcttcctc ctcactcttg gctaaaatga gagctagaaa ccacctgatt    4200
ctgccagagc gtttagaaag tgaaagcggg cacctgcagg aagcttctgc cctgctgccc    4260
accacagaac acgatgacct tctggtggag atgagaaact tcatcgcttt ccaggcccac    4320
actgatggcc aggccagcac cagggagata ctgcaggagt ttgaatccaa gttatctgca    4380
tcacagtctt gtgtcttccg agaactattg agaaatctgt gcactttcca tagaacttct    4440
ggtggtgaag gaatttggaa actcaagcca gaatactgc                          4479
```

<210> SEQ ID NO 3
<211> LENGTH: 7006
<212> TYPE: DNA
<213> ORGANISM: Homo sapiens

<400> SEQUENCE: 3

```
agcagaagtc ggagtcgctg ttgggggcgg tgtctatggt tgagctgagg gcgcaggcgc      60
cacggcccgt cgagctgggt tccaaggcgg ctggcggcgg tagcgtctct gtttccttgt     120
gggcgctcgc gcggccctgg gtagtctgta gagaatgcca aatgagggaa tcccccactc     180
aagtcaaact caggagcaag actgtttaca gagtcaacct gtcagtaata atgaagaaat     240
ggcaatcaag caagaaagtg gtggtgatgg ggaggtggag gagtacctct cctttcgttc     300
tgtgggtgac gggctgtcca cctctgctgt ggggtgcgca tcagcagctc cgaggagagg     360
gccagccctg ctgcacatcg accgacatca gatccaggca gtagagccta cgcccaggc     420
ccttgagctg cagggtttgg gtgtggacgt ctatgaccag gacgtgctgg aacagggagt     480
gcttcagcag gtggacaatg ccatccatga ggccagccgt gcctcccagc tcgttgacgt     540
ggagaaggag tatcggtcgg tcctggatga cctcacgtca tgtacgacat ccctaaggca     600
aatcaataaa attattgaac agcttagccc tcaagctgcc accagcagag acatcaacag     660
gaaactagat tctgtaaaac gacagaagta taataaggaa caacagctaa aaaagatcac     720
tgcaaaacaa aagcatctcc aggccatcct tggaggagca gaggtgaaaa ttgaactaga     780
tcacgccagt ctggaggagg atgcagagcc ggggccatcc agtcttggca gcatgctcat     840
gcctgtccag gagactgcct gggaagagct catccgcact ggccagatga cacctttggg     900
tacccagatc cctcagaaac aggagaaaaa gcccagaaaa atcatgctta atgaagcatc     960
aggcttcgaa aagtatttgg cagatcaagc aaaactgtct tttgaaagga agaagcaagg    1020
ttgtaataaa agagcagcta aaaagctcc agccccagtc acgcctccag ccccagtgca    1080
aaataaaaac aaaccaaaca gaaagccag agttctgtcc aaaaaagagg agcgtttgaa    1140
aaagcacatc aagaaactcc agaagagggc tttgcagttc caggggaaag tgggattgcc    1200
aaaggcaagg agaccttggg agtcagacat gaggccagag gcagagggag actctgaggg    1260
tgaagagtct gagtatttcc ccacagagga ggaggaagag gaggaaatg acgaggtgga    1320
ggggcagag gcggacctgt ctggagatgg tactgactat gagctgaagc ctctgcccaa    1380
gggcgggaaa cggcagaaga agtgccagt gcaggagatt gatgatgact ttttcccaag    1440
ttctgggaa gaagctgaag ctgcttctgt aggagaagga ggaggaggag gtcggaaagt    1500
```

```
gggaagatac cgagatgatg gagatgaaga ttattataag cagcggttaa ggagatggaa      1560
taaactgaga ctgcaggaca aagagaaacg tctgaagctg gaggacgatt ctgaggaaag      1620
tgatgctgaa tttgacgaag gttttaaagt gccaggtttt ctgttcaaaa agcttttaa      1680 gtaccagcag acaggtgtta ggtggctgtg ggaattgcac tgccagcagg caggaggaat      1740
tctgggagat gaaatgggat tggcaagac catccagata attgccttct ggcaggtct        1800 gagctacagc aagatcagga ctcgtggttc aaattacagg tttgaggggt tgggtccaac      1860
tgtaattgtc tgtccaacaa cagtgatgca tcagtgggtg aaggaatttc acacgtggtg     1920
gcctccgttc agagtggcaa ttctacatga aaccggttcc tatacccaca aaaggagaa      1980 actaattcga gatgttgctc attgtcatgg aattttgatc acatcttact cctacattcg      2040
attgatgcag gatgacatta gcaggtatga ctggcactat gtgatcttgg acgaaggaca     2100
caaaattcga aatccaaatg ctgctgtcac ccttgcttgc aaacagtttc gcaccctca      2160 tcggatcatt ctgtctggct caccgatgca aataacctc cgagagctgt ggtcgctctt      2220
tgacttcatc ttcccgggaa agttaggcac gttgcctgtg tttatggagc agttctccgt     2280
ccccatcacc atgggggat attcaaatgc ttccccagta caggtcaaaa ctgcttacaa      2340
gtgtgcatgt gtcttacgag ataccataaa tccatacct ctgcggagaa tgaagtcaga      2400
tgtcaagatg agccttctt tgccagataa aaatgaacag gtcttatttt gccgtcttac      2460
agatgagcag cataaagtct accaaaattt cgttgattcc aaagaagttt acaggattct      2520
caatggagag atgcagattt tctccggact tatagcccta agaaaaattt gcaaccaccc     2580
tgatctcttt tctggaggtc ccaagaatct caaaggtctt cctgatgatg aactagaaga    2640
agatcagttt gggtactgga acgttctgg gaaaatgatt gttgttgagt ctttgttgaa      2700
aatatggcac aagcagggtc agcgagtatt gctgttttct cagtcaaggc agatgctgga    2760
catacttgaa gtattcctta gagcccaaaa gtatacctat ctcaagatgg atggtaccac    2820
tacaatagct tcaagacagc cactgattac gagatacaat gaggacacat ccatatttgt     2880
gtttcttctg accacgcggg tgggcggctt aggtgtcaac ctgacggggg caaacagagt    2940
tgtcatctat gacccagact ggaacccaag cacggacacg caggcccggg agcgagcatg    3000
gagaataggc cagaagaagc aagtgactgt gtacaggctc ctgactgcgg gcaccattga     3060
agaaaagatc taccaccgac aaatcttcaa gcagttttg acaaatagag tgctaaaaga    3120
cccaaaacaa aggcggtttt tcaaatccaa tgatctctat gagctatta ctctgactag     3180 tcctgatgca tcccagagca ctgaaacaag tgcaatttt gcaggaactg gatcagatgt    3240
tcagacaccc aaatgccatc taaaaagaag gattcaacca gcctttggag cagaccatga    3300
tgttccaaaa cgcaagaagt ccctgcttc taacatatct gtaaatgatg ccacatcatc     3360
tgaagagaaa tctgaggcta aaggagctga agtaaatgca gtaacttcta atcgaagtga    3420
tcctttgaaa gatgaccctc acatgagtag taatgtaact agcaatgata ggcttggaga    3480
agagacaaat gcagtatctg gaccagaaga gttgtcagtg attagtggaa atggggaatg    3540
ttcaaattct tcaggaacag gcaaaacttc tatgccatct ggtgatgaaa gcattgatga    3600
aaagttaggt ctttcttaca aaagagaaag acccagccag gctcaaacag aagcttttg      3660 ggagaataaa caaatggaaa ataattttta taagcacaag tcaaaaacaa aacatcatag    3720
tgtggcagaa gaagagaccc tgagaaaaca tctgagacca agcaaaaagc ctaagaactc    3780
taagcattgc agagacgcca gtttgaagg aactcgaatt ccacacctgg tgaagaaaag    3840
gcgttaccag aagcaagaca gtgaaaacaa gagtgaggcc aaggaacaga gcaatgacga    3900
```

```
ttatgttttg gaaaagcttt tcaaaaaatc agttggcgtg cacagtgtca tgaagcacga   3960
tgccatcatg gatggagcca gcccagatta tgtactggtg gaggcagaag ccaaccgagt   4020
ggcccaggat gccctgaaag cactgaggct ctctcgtcag cggtgtctgg gagcagtgtc   4080
tggtgttccc acctggactg gccacagggg gatttctggt gcaccagcag gaaaaaagag   4140
tagatttggt aagaaaagga attctaactt ctctgtgcag catccttcat caacatctcc   4200
aacagagaag tgccaggatg gcatcatgaa aaggaggga aaagataatg tccctgagca   4260
ttttagtgga agagcagaag atgcagactc ttcatccggg cccctcgctt cctcctcact   4320
cttggctaaa atgagagcta gaaaccacct gattctgcca gagcgtttag aaagtgaaag   4380
cgggcacctg caggaagctt ctgccctgct gcccaccaca gaacacgatg accttctggt   4440
ggagatgaga aacttcatcg ctttccaggc ccacactgat ggccaggcca gcaccaggga   4500
gatactgcag gagtttgaat ccaagttatc tgcatcacag tcttgtgtct tccgagaact   4560
attgagaaat ctgtgcactt tccatagaac ttctggtggt gaaggaattt ggaaactcaa   4620
gccagaatac tgctaaacaa cattgcttcc taaactttca gtcccttttt ctaacgggc   4680
atttctgatt attaatttat tattaataat catgttgtc aatggaagtt ggctgcactt   4740
gatgtttgtt tgcatgatgt ctacctcaga attaaaactt taaggaagaa gaaactcttc   4800
tctgaaagtt aaaagtttta ataatgctag ctaaaggaga aaatacttgg attgattttt   4860
tttttttgg caatctaatt atattgtaaa tcaggtacct aacagttact ccttggagca   4920
catttgttcc tttacccaaa agatgctgtc agggagcaca gttagaagtt tgcagaacag   4980
aaatctcaat attttttttt attggtgcta aaaacaggtc ttacattcag tcagacctgt   5040
tcaataagtt catcaatatc tgataacagc attattttga tgcttaaact ttaaacattt   5100
atatttacca tttgccaccc acaaaggtca ggtttgttat tgttgtttg ataattatat   5160
taattttctt ggaaagatcc tcttttcaag gtactggtaa attggtgagt attttttatta   5220
gtaaagcatg aaatagtatg gtaataaatg ataagacatg tatttgtgga aagctgtagg   5280
gtattcagtt taccctggct ttcctttaag cagagggcat cttttttctct cctacagtca   5340
caaaatgtgt tatcattaaa aaaaatcaaa ttaaagccaa aagtaggtac ataaaaacca   5400
cacacatgca tgcacacaaa catcactgca gcccacagca gacccagccg ttgttaccat   5460
gaagtgacac cactccaggc ctctcttgtc tgcaggctgg caggctgtct tctctccagt   5520
tgccttcgtc ttgcgcctgc ctttgcattc cttgcgacgg gctttcttgt ttctgcggtt   5580
tggattccag ccaaggctgt ttgtatctca ctactgttta tgtgtttgtg gttctgtgat   5640
ggtgttgctt tgatcctcag tttattttct tacccatgtt tttcttgttt ccttctcagg   5700
atgattttat catctcatct ttgaagtgtt gtttccgaa attcatcgta ttcctgaaat   5760
ttcttcttag ctgtcttagt gcagtttgtt tcttggattt gtattctctg gcatgctctt   5820
ttcctctctc tcattttttct gtagtatgcc tgccctccta ccctgctatt tctttacatc   5880
tctctcatgc ttaacatgga tagctgtgtc cagatcttct gtctgctcat ccatgtgact   5940
cagagaggag ggttctgggc aggggggcct tgccggactg catgagagga catgagtttt   6000
gctttctctg ctctaatatt ttgcttaagc caagaatcct tttcttagag atgttctata   6060
tgattcctgt caggattttc tagtttttttt tggattatag cttgttcatt tcttttgttt   6120
ttagtttggt ttatatataa tgagggaaga agatgattac attattttg tcactttgcc   6180
atcattgttt agaagtcata gaaagaattt ttaaataggc caataagtct taaacttgag   6240
```

```
tacttggctt agaagaaagt caaaactcct tccttttgta ctaagtggtt tgtttctggg    6300
gagctcttaa tttctatttt tataatcatt agcctataag gaaattgtgt cttccttgtt    6360
ctcagggtga tctgctgacc ttgttcactc atgaagcatt tgggtatcat acttatagtg    6420
tctgaaacat aaactgtatt gagctagaca aggtatagcc tcctcttcaa gtagcaaata    6480
ctatcaaaag ctataatgca gtaggagcaa ggtggtcctt gttccagttt ttgtctcagt    6540
tctgctgctg atgtaccatg atcttgggaa ggtggtgtct cagtgtggag atctgacaca    6600
ttgttaccgt gcctcctggc tggagggact tggagaacaa tgcagttaag tagaatggtt    6660
ttaacaatac agagaaattt attcatttag ataaaaatct gatttttaga actttaaaag    6720
ctttgtacag tgtaaataga tttaatgtat ttaacatgct ttatcagcac aaataaagga    6780
ttttaaaatt ttgtcaaaaa attaaatgtt aatactatca ccattaaaaa tgttcaagca    6840
atagtctgcc tccccacccc cacaccatct tgcacctgtt ccacagctaa gtacagccct    6900
aggtttggtg tgtattctcc atgcatttag agaatcacat gacacagact gctgctataa    6960
tgtcattttc ccattcttcc tttactaata aatttttga gtttta                   7006
```

<210> SEQ ID NO 4
<211> LENGTH: 1493
<212> TYPE: PRT
<213> ORGANISM: Homo sapiens

<400> SEQUENCE: 4

```
Met Pro Asn Glu Gly Ile Pro His Ser Ser Gln Thr Gln Glu Gln Asp
1               5                   10                  15

Cys Leu Gln Ser Gln Pro Val Ser Asn Asn Glu Glu Met Ala Ile Lys
                20                  25                  30

Gln Glu Ser Gly Gly Asp Gly Glu Val Glu Glu Tyr Leu Ser Phe Arg
            35                  40                  45

Ser Val Gly Asp Gly Leu Ser Thr Ser Ala Val Gly Cys Ala Ser Ala
        50                  55                  60

Ala Pro Arg Arg Gly Pro Ala Leu Leu His Ile Asp Arg His Gln Ile
65                  70                  75                  80

Gln Ala Val Glu Pro Ser Ala Gln Ala Leu Glu Leu Gln Gly Leu Gly
                85                  90                  95

Val Asp Val Tyr Asp Gln Asp Val Leu Glu Gln Gly Val Leu Gln Gln
            100                 105                 110

Val Asp Asn Ala Ile His Glu Ala Ser Arg Ala Ser Gln Leu Val Asp
        115                 120                 125

Val Glu Lys Glu Tyr Arg Ser Val Leu Asp Asp Leu Thr Ser Cys Thr
    130                 135                 140

Thr Ser Leu Arg Gln Ile Asn Lys Ile Ile Glu Gln Leu Ser Pro Gln
145                 150                 155                 160

Ala Ala Thr Ser Arg Asp Ile Asn Arg Lys Leu Asp Ser Val Lys Arg
                165                 170                 175

Gln Lys Tyr Tyr Lys Glu Gln Gln Leu Lys Lys Ile Thr Ala Lys Gln
            180                 185                 190

Lys His Leu Gln Ala Ile Leu Gly Gly Ala Glu Val Lys Ile Glu Leu
        195                 200                 205

Asp His Ala Ser Leu Glu Glu Asp Ala Glu Pro Gly Pro Ser Ser Leu
    210                 215                 220

Gly Ser Met Leu Met Pro Val Gln Glu Thr Ala Trp Glu Glu Leu Ile
225                 230                 235                 240
```

-continued

```
Arg Thr Gly Gln Met Thr Pro Phe Gly Thr Gln Ile Pro Gln Lys Gln
            245                 250                 255
Glu Lys Lys Pro Arg Lys Ile Met Leu Asn Glu Ala Ser Gly Phe Glu
        260                 265                 270
Lys Tyr Leu Ala Asp Gln Ala Lys Leu Ser Phe Glu Arg Lys Lys Gln
    275                 280                 285
Gly Cys Asn Lys Arg Ala Ala Arg Lys Ala Pro Ala Pro Val Thr Pro
290                 295                 300
Pro Ala Pro Val Gln Asn Lys Asn Pro Asn Lys Lys Ala Arg Val
305                 310                 315                 320
Leu Ser Lys Lys Glu Glu Arg Leu Lys Lys His Ile Lys Lys Leu Gln
                325                 330                 335
Lys Arg Ala Leu Gln Phe Gln Gly Lys Val Gly Leu Pro Lys Ala Arg
            340                 345                 350
Arg Pro Trp Glu Ser Asp Met Arg Pro Glu Ala Glu Gly Asp Ser Glu
        355                 360                 365
Gly Glu Glu Ser Glu Tyr Phe Pro Thr Glu Glu Glu Glu Glu Glu Glu
    370                 375                 380
Asp Asp Glu Val Glu Gly Ala Glu Ala Asp Leu Ser Gly Asp Gly Thr
385                 390                 395                 400
Asp Tyr Glu Leu Lys Pro Leu Pro Lys Gly Gly Lys Arg Gln Lys Lys
                405                 410                 415
Val Pro Val Gln Glu Ile Asp Asp Phe Phe Pro Ser Ser Gly Glu
            420                 425                 430
Glu Ala Glu Ala Ala Ser Val Gly Gly Gly Gly Gly Arg Lys
        435                 440                 445
Val Gly Arg Tyr Arg Asp Asp Gly Asp Glu Asp Tyr Tyr Lys Gln Arg
    450                 455                 460
Leu Arg Arg Trp Asn Lys Leu Arg Leu Gln Asp Lys Glu Lys Arg Leu
465                 470                 475                 480
Lys Leu Glu Asp Asp Ser Glu Glu Ser Asp Ala Glu Phe Asp Glu Gly
                485                 490                 495
Phe Lys Val Pro Gly Phe Leu Phe Lys Lys Leu Phe Lys Tyr Gln Gln
            500                 505                 510
Thr Gly Val Arg Trp Leu Trp Glu Leu His Cys Gln Gln Ala Gly Gly
        515                 520                 525
Ile Leu Gly Asp Glu Met Gly Leu Gly Lys Thr Ile Gln Ile Ile Ala
    530                 535                 540
Phe Leu Ala Gly Leu Ser Tyr Ser Lys Ile Arg Thr Arg Gly Ser Asn
545                 550                 555                 560
Tyr Arg Phe Glu Gly Leu Gly Pro Thr Val Ile Val Cys Pro Thr Thr
                565                 570                 575
Val Met His Gln Trp Val Lys Glu Phe His Thr Trp Trp Pro Pro Phe
            580                 585                 590
Arg Val Ala Ile Leu His Glu Thr Gly Ser Tyr Thr His Lys Lys Glu
        595                 600                 605
Lys Leu Ile Arg Asp Val Ala His Cys His Gly Ile Leu Ile Thr Ser
    610                 615                 620
Tyr Ser Tyr Ile Arg Leu Met Gln Asp Ile Ser Arg Tyr Asp Trp
625                 630                 635                 640
His Tyr Val Ile Leu Asp Glu Gly His Lys Ile Arg Asn Pro Asn Ala
                645                 650                 655
Ala Val Thr Leu Ala Cys Lys Gln Phe Arg Thr Pro His Arg Ile Ile
```

```
                    660                 665                 670
Leu Ser Gly Ser Pro Met Gln Asn Asn Leu Arg Glu Leu Trp Ser Leu
                675                 680                 685

Phe Asp Phe Ile Phe Pro Gly Lys Leu Gly Thr Leu Pro Val Phe Met
            690                 695                 700

Glu Gln Phe Ser Val Pro Ile Thr Met Gly Gly Tyr Ser Asn Ala Ser
705                 710                 715                 720

Pro Val Gln Val Lys Thr Ala Tyr Lys Cys Ala Cys Val Leu Arg Asp
                725                 730                 735

Thr Ile Asn Pro Tyr Leu Leu Arg Arg Met Lys Ser Asp Val Lys Met
            740                 745                 750

Ser Leu Ser Leu Pro Asp Lys Asn Glu Gln Val Leu Phe Cys Arg Leu
        755                 760                 765

Thr Asp Glu Gln His Lys Val Tyr Gln Asn Phe Val Asp Ser Lys Glu
        770                 775                 780

Val Tyr Arg Ile Leu Asn Gly Glu Met Gln Ile Phe Ser Gly Leu Ile
785                 790                 795                 800

Ala Leu Arg Lys Ile Cys Asn His Pro Asp Leu Phe Ser Gly Gly Pro
                805                 810                 815

Lys Asn Leu Lys Gly Leu Pro Asp Asp Glu Leu Glu Glu Asp Gln Phe
                820                 825                 830

Gly Tyr Trp Lys Arg Ser Gly Lys Met Ile Val Val Glu Ser Leu Leu
            835                 840                 845

Lys Ile Trp His Lys Gln Gly Gln Arg Val Leu Leu Phe Ser Gln Ser
850                 855                 860

Arg Gln Met Leu Asp Ile Leu Glu Val Phe Leu Arg Ala Gln Lys Tyr
865                 870                 875                 880

Thr Tyr Leu Lys Met Asp Gly Thr Thr Thr Ile Ala Ser Arg Gln Pro
                885                 890                 895

Leu Ile Thr Arg Tyr Asn Glu Asp Thr Ser Ile Phe Val Phe Leu Leu
            900                 905                 910

Thr Thr Arg Val Gly Gly Leu Gly Val Asn Leu Thr Gly Ala Asn Arg
        915                 920                 925

Val Val Ile Tyr Asp Pro Asp Trp Asn Pro Ser Thr Asp Thr Gln Ala
        930                 935                 940

Arg Glu Arg Ala Trp Arg Ile Gly Gln Lys Lys Gln Val Thr Val Tyr
945                 950                 955                 960

Arg Leu Leu Thr Ala Gly Thr Ile Glu Glu Lys Ile Tyr His Arg Gln
                965                 970                 975

Ile Phe Lys Gln Phe Leu Thr Asn Arg Val Leu Lys Asp Pro Lys Gln
            980                 985                 990

Arg Arg Phe Phe Lys Ser Asn Asp Leu Tyr Glu Leu Phe Thr Leu Thr
        995                 1000                1005

Ser Pro Asp Ala Ser Gln Ser Thr Glu Thr Ser Ala Ile Phe Ala
        1010                1015                1020

Gly Thr Gly Ser Asp Val Gln Thr Pro Lys Cys His Leu Lys Arg
        1025                1030                1035

Arg Ile Gln Pro Ala Phe Gly Ala Asp His Asp Val Pro Lys Arg
        1040                1045                1050

Lys Lys Phe Pro Ala Ser Asn Ile Ser Val Asn Asp Ala Thr Ser
        1055                1060                1065

Ser Glu Glu Lys Ser Glu Ala Lys Gly Ala Glu Val Asn Ala Val
        1070                1075                1080
```

```
Thr Ser Asn Arg Ser Asp Pro Leu Lys Asp Pro His Met Ser
1085           1090               1095

Ser Asn Val Thr Ser Asn Asp Arg Leu Gly Glu Glu Thr Asn Ala
1100           1105               1110

Val Ser Gly Pro Glu Glu Leu Ser Val Ile Ser Gly Asn Gly Glu
1115           1120               1125

Cys Ser Asn Ser Ser Gly Thr Gly Lys Thr Ser Met Pro Ser Gly
1130           1135               1140

Asp Glu Ser Ile Asp Glu Lys Leu Gly Leu Ser Tyr Lys Arg Glu
1145           1150               1155

Arg Pro Ser Gln Ala Gln Thr Glu Ala Phe Trp Glu Asn Lys Gln
1160           1165               1170

Met Glu Asn Asn Phe Tyr Lys His Lys Ser Lys Thr Lys His His
1175           1180               1185

Ser Val Ala Glu Glu Glu Thr Leu Glu Lys His Leu Arg Pro Lys
1190           1195               1200

Gln Lys Pro Lys Asn Ser Lys His Cys Arg Asp Ala Lys Phe Glu
1205           1210               1215

Gly Thr Arg Ile Pro His Leu Val Lys Lys Arg Arg Tyr Gln Lys
1220           1225               1230

Gln Asp Ser Glu Asn Lys Ser Glu Ala Lys Glu Gln Ser Asn Asp
1235           1240               1245

Asp Tyr Val Leu Glu Lys Leu Phe Lys Lys Ser Val Gly Val His
1250           1255               1260

Ser Val Met Lys His Asp Ala Ile Met Asp Gly Ala Ser Pro Asp
1265           1270               1275

Tyr Val Leu Val Glu Ala Glu Ala Asn Arg Val Ala Gln Asp Ala
1280           1285               1290

Leu Lys Ala Leu Arg Leu Ser Arg Gln Arg Cys Leu Gly Ala Val
1295           1300               1305

Ser Gly Val Pro Thr Trp Thr Gly His Arg Gly Ile Ser Gly Ala
1310           1315               1320

Pro Ala Gly Lys Lys Ser Arg Phe Gly Lys Lys Arg Asn Ser Asn
1325           1330               1335

Phe Ser Val Gln His Pro Ser Ser Thr Ser Pro Thr Glu Lys Cys
1340           1345               1350

Gln Asp Gly Ile Met Lys Lys Glu Gly Lys Asp Asn Val Pro Glu
1355           1360               1365

His Phe Ser Gly Arg Ala Glu Asp Ala Asp Ser Ser Ser Gly Pro
1370           1375               1380

Leu Ala Ser Ser Ser Leu Leu Ala Lys Met Arg Ala Arg Asn His
1385           1390               1395

Leu Ile Leu Pro Glu Arg Leu Glu Ser Glu Ser Gly His Leu Gln
1400           1405               1410

Glu Ala Ser Ala Leu Leu Pro Thr Thr Glu His Asp Asp Leu Leu
1415           1420               1425

Val Glu Met Arg Asn Phe Ile Ala Phe Gln Ala His Thr Asp Gly
1430           1435               1440

Gln Ala Ser Thr Arg Glu Ile Leu Gln Glu Phe Glu Ser Lys Leu
1445           1450               1455

Ser Ala Ser Gln Ser Cys Val Phe Arg Glu Leu Leu Arg Asn Leu
1460           1465               1470
```

```
Cys Thr Phe His Arg Thr Ser Gly Gly Glu Gly Ile Trp Lys Leu
    1475                1480                1485

Lys Pro Glu Tyr Cys
    1490

<210> SEQ ID NO 5
<211> LENGTH: 1493
<212> TYPE: PRT
<213> ORGANISM: Homo sapiens

<400> SEQUENCE: 5

Met Pro Asn Glu Gly Ile Pro His Ser Ser Gln Thr Gln Gln Asp
1               5                   10                  15

Cys Leu Gln Ser Gln Pro Val Ser Asn Asn Glu Glu Met Ala Ile Lys
                20                  25                  30

Gln Glu Ser Gly Gly Asp Gly Glu Val Glu Glu Tyr Leu Ser Phe Arg
            35                  40                  45

Ser Val Gly Asp Gly Leu Ser Thr Ser Ala Val Gly Cys Ala Ser Ala
50                  55                  60

Ala Pro Arg Arg Gly Pro Ala Leu Leu His Ile Asp Arg His Gln Ile
65                  70                  75                  80

Gln Ala Val Glu Pro Ser Ala Gln Ala Leu Glu Leu Gln Gly Leu Gly
                85                  90                  95

Val Asp Val Tyr Asp Gln Asp Val Leu Glu Gly Val Leu Gln Gln
            100                 105                 110

Val Asp Asn Ala Ile His Glu Ala Ser Arg Ala Ser Gln Leu Val Asp
        115                 120                 125

Val Glu Lys Glu Tyr Arg Ser Val Leu Asp Asp Leu Thr Ser Cys Thr
130                 135                 140

Thr Ser Leu Arg Gln Ile Asn Lys Ile Ile Glu Gln Leu Ser Pro Gln
145                 150                 155                 160

Ala Ala Thr Ser Arg Asp Ile Asn Arg Lys Leu Asp Ser Val Lys Arg
                165                 170                 175

Gln Lys Tyr Asn Lys Glu Gln Gln Leu Lys Lys Ile Thr Ala Lys Gln
            180                 185                 190

Lys His Leu Gln Ala Ile Leu Gly Gly Ala Glu Val Lys Ile Glu Leu
        195                 200                 205

Asp His Ala Ser Leu Glu Glu Asp Ala Glu Pro Gly Pro Ser Ser Leu
210                 215                 220

Gly Ser Met Leu Met Pro Val Gln Glu Thr Ala Trp Glu Glu Leu Ile
225                 230                 235                 240

Arg Thr Gly Gln Met Thr Pro Phe Gly Thr Gln Ile Pro Gln Lys Gln
                245                 250                 255

Glu Lys Lys Pro Arg Lys Ile Met Leu Asn Glu Ala Ser Gly Phe Glu
            260                 265                 270

Lys Tyr Leu Ala Asp Gln Ala Lys Leu Ser Phe Glu Arg Lys Lys Gln
        275                 280                 285

Gly Cys Asn Lys Arg Ala Ala Arg Lys Ala Pro Ala Pro Val Thr Pro
290                 295                 300

Pro Ala Pro Val Gln Asn Lys Asn Lys Pro Asn Lys Lys Ala Arg Val
305                 310                 315                 320

Leu Ser Lys Lys Glu Glu Arg Leu Lys Lys His Ile Lys Lys Leu Gln
                325                 330                 335

Lys Arg Ala Leu Gln Phe Gln Gly Lys Val Gly Leu Pro Lys Ala Arg
            340                 345                 350
```

```
Arg Pro Trp Glu Ser Asp Met Arg Pro Glu Ala Glu Gly Asp Ser Glu
        355                 360                 365

Gly Glu Glu Ser Glu Tyr Phe Pro Thr Glu Glu Glu Glu Glu Glu Glu
        370                 375                 380

Asp Asp Glu Val Glu Gly Ala Glu Ala Asp Leu Ser Gly Asp Gly Thr
385                 390                 395                 400

Asp Tyr Glu Leu Lys Pro Leu Pro Lys Gly Gly Lys Arg Gln Lys Lys
                405                 410                 415

Val Pro Val Gln Glu Ile Asp Asp Phe Phe Pro Ser Ser Gly Glu
                420                 425                 430

Glu Ala Glu Ala Ala Ser Val Gly Glu Gly Gly Gly Gly Arg Lys
        435                 440                 445

Val Gly Arg Tyr Arg Asp Asp Gly Asp Glu Asp Tyr Tyr Lys Gln Arg
        450                 455                 460

Leu Arg Arg Trp Asn Lys Leu Arg Leu Gln Asp Lys Glu Lys Arg Leu
465                 470                 475                 480

Lys Leu Glu Asp Asp Ser Glu Glu Ser Asp Ala Glu Phe Asp Glu Gly
                485                 490                 495

Phe Lys Val Pro Gly Phe Leu Phe Lys Lys Leu Phe Lys Tyr Gln Gln
                500                 505                 510

Thr Gly Val Arg Trp Leu Trp Glu Leu His Cys Gln Gln Ala Gly Gly
        515                 520                 525

Ile Leu Gly Asp Glu Met Gly Leu Gly Lys Thr Ile Gln Ile Ile Ala
        530                 535                 540

Phe Leu Ala Gly Leu Ser Tyr Ser Lys Ile Arg Thr Arg Gly Ser Asn
545                 550                 555                 560

Tyr Arg Phe Glu Gly Leu Gly Pro Thr Val Ile Val Cys Pro Thr Thr
                565                 570                 575

Val Met His Gln Trp Val Lys Glu Phe His Thr Trp Trp Pro Pro Phe
                580                 585                 590

Arg Val Ala Ile Leu His Glu Thr Gly Ser Tyr Thr His Lys Lys Glu
        595                 600                 605

Lys Leu Ile Arg Asp Val Ala His Cys His Gly Ile Leu Ile Thr Ser
        610                 615                 620

Tyr Ser Tyr Ile Arg Leu Met Gln Asp Asp Ile Ser Arg Tyr Asp Trp
625                 630                 635                 640

His Tyr Val Ile Leu Asp Glu Gly His Lys Ile Arg Asn Pro Asn Ala
                645                 650                 655

Ala Val Thr Leu Ala Cys Lys Gln Phe Arg Thr Pro His Arg Ile Ile
                660                 665                 670

Leu Ser Gly Ser Pro Met Gln Asn Asn Leu Arg Glu Leu Trp Ser Leu
        675                 680                 685

Phe Asp Phe Ile Phe Pro Gly Lys Leu Gly Thr Leu Pro Val Phe Met
        690                 695                 700

Glu Gln Phe Ser Val Pro Ile Thr Met Gly Gly Tyr Ser Asn Ala Ser
705                 710                 715                 720

Pro Val Gln Val Lys Thr Ala Tyr Lys Cys Ala Cys Val Leu Arg Asp
                725                 730                 735

Thr Ile Asn Pro Tyr Leu Leu Arg Arg Met Lys Ser Asp Val Lys Met
                740                 745                 750

Ser Leu Ser Leu Pro Asp Lys Asn Glu Gln Val Leu Phe Cys Arg Leu
        755                 760                 765
```

```
Thr Asp Glu Gln His Lys Val Tyr Gln Asn Phe Val Asp Ser Lys Glu
770                 775                 780
Val Tyr Arg Ile Leu Asn Gly Glu Met Gln Ile Phe Ser Gly Leu Ile
785                 790                 795                 800
Ala Leu Arg Lys Ile Cys Asn His Pro Asp Leu Phe Ser Gly Pro
                805                 810                 815
Lys Asn Leu Lys Gly Leu Pro Asp Asp Glu Leu Glu Glu Asp Gln Phe
            820                 825                 830
Gly Tyr Trp Lys Arg Ser Gly Lys Met Ile Val Val Glu Ser Leu Leu
                835                 840                 845
Lys Ile Trp His Lys Gln Gly Gln Arg Val Leu Leu Phe Ser Gln Ser
850                 855                 860
Arg Gln Met Leu Asp Ile Leu Glu Val Phe Leu Arg Ala Gln Lys Tyr
865                 870                 875                 880
Thr Tyr Leu Lys Met Asp Gly Thr Thr Thr Ile Ala Ser Arg Gln Pro
                885                 890                 895
Leu Ile Thr Arg Tyr Asn Glu Asp Thr Ser Ile Phe Val Phe Leu Leu
            900                 905                 910
Thr Thr Arg Val Gly Gly Leu Gly Val Asn Leu Thr Gly Ala Asn Arg
            915                 920                 925
Val Val Ile Tyr Asp Pro Asp Trp Asn Pro Ser Thr Asp Thr Gln Ala
930                 935                 940
Arg Glu Arg Ala Trp Arg Ile Gly Gln Lys Lys Gln Val Thr Val Tyr
945                 950                 955                 960
Arg Leu Leu Thr Ala Gly Thr Ile Glu Glu Lys Ile Tyr His Arg Gln
                965                 970                 975
Ile Phe Lys Gln Phe Leu Thr Asn Arg Val Leu Lys Asp Pro Lys Gln
            980                 985                 990
Arg Arg Phe Phe Lys Ser Asn Asp Leu Tyr Glu Leu Phe Thr Leu Thr
                995                 1000                1005
Ser Pro Asp Ala Ser Gln Ser Thr Glu Thr Ser Ala Ile Phe Ala
            1010                1015                1020
Gly Thr Gly Ser Asp Val Gln Thr Pro Lys Cys His Leu Lys Arg
            1025                1030                1035
Arg Ile Gln Pro Ala Phe Gly Ala Asp His Asp Val Pro Lys Arg
            1040                1045                1050
Lys Lys Phe Pro Ala Ser Asn Ile Ser Val Asn Asp Ala Thr Ser
            1055                1060                1065
Ser Glu Glu Lys Ser Glu Ala Lys Gly Ala Glu Val Asn Ala Val
            1070                1075                1080
Thr Ser Asn Arg Ser Asp Pro Leu Lys Asp Asp Pro His Met Ser
            1085                1090                1095
Ser Asn Val Thr Ser Asn Asp Arg Leu Gly Glu Glu Thr Asn Ala
            1100                1105                1110
Val Ser Gly Pro Glu Glu Leu Ser Val Ile Ser Gly Asn Gly Glu
            1115                1120                1125
Cys Ser Asn Ser Ser Gly Thr Gly Lys Thr Ser Met Pro Ser Gly
            1130                1135                1140
Asp Glu Ser Ile Asp Glu Lys Leu Gly Leu Ser Tyr Lys Arg Glu
            1145                1150                1155
Arg Pro Ser Gln Ala Gln Thr Glu Ala Phe Trp Glu Asn Lys Gln
            1160                1165                1170
Met Glu Asn Asn Phe Tyr Lys His Lys Ser Lys Thr Lys His His
```

| | | | | | | | | | |
|---|---|---|---|---|---|---|---|---|---|
| | | | 1175 | | | 1180 | | | 1185 |

Ser Val Ala Glu Glu Thr Leu Glu Lys His Leu Arg Pro Lys
    1190                      1195                    1200

Gln Lys Pro Lys Asn Ser Lys His Cys Arg Asp Ala Lys Phe Glu
    1205                      1210                    1215

Gly Thr Arg Ile Pro His Leu Val Lys Arg Arg Tyr Gln Lys
    1220                      1225                    1230

Gln Asp Ser Glu Asn Lys Ser Glu Ala Lys Glu Gln Ser Asn Asp
    1235                      1240                    1245

Asp Tyr Val Leu Glu Lys Leu Phe Lys Lys Ser Val Gly Val His
    1250                      1255                    1260

Ser Val Met Lys His Asp Ala Ile Met Asp Gly Ala Ser Pro Asp
    1265                      1270                    1275

Tyr Val Leu Val Glu Ala Glu Ala Asn Arg Val Ala Gln Asp Ala
    1280                      1285                    1290

Leu Lys Ala Leu Arg Leu Ser Arg Gln Arg Cys Leu Gly Ala Val
    1295                      1300                    1305

Ser Gly Val Pro Thr Trp Thr Gly His Arg Gly Ile Ser Gly Ala
    1310                      1315                    1320

Pro Ala Gly Lys Lys Ser Arg Phe Gly Lys Lys Arg Asn Ser Asn
    1325                      1330                    1335

Phe Ser Val Gln His Pro Ser Ser Thr Ser Pro Thr Glu Lys Cys
    1340                      1345                    1350

Gln Asp Gly Ile Met Lys Lys Glu Gly Lys Asp Asn Val Pro Glu
    1355                      1360                    1365

His Phe Ser Gly Arg Ala Glu Asp Ala Asp Ser Ser Ser Gly Pro
    1370                      1375                    1380

Leu Ala Ser Ser Ser Leu Leu Ala Lys Met Arg Ala Arg Asn His
    1385                      1390                    1395

Leu Ile Leu Pro Glu Arg Leu Glu Ser Glu Ser Gly His Leu Gln
    1400                      1405                    1410

Glu Ala Ser Ala Leu Leu Pro Thr Thr Glu His Asp Asp Leu Leu
    1415                      1420                    1425

Val Glu Met Arg Asn Phe Ile Ala Phe Gln Ala His Thr Asp Gly
    1430                      1435                    1440

Gln Ala Ser Thr Arg Glu Ile Leu Gln Glu Phe Glu Ser Lys Leu
    1445                      1450                    1455

Ser Ala Ser Gln Ser Cys Val Phe Arg Glu Leu Leu Arg Asn Leu
    1460                      1465                    1470

Cys Thr Phe His Arg Thr Ser Gly Gly Glu Gly Ile Trp Lys Leu
    1475                      1480                    1485

Lys Pro Glu Tyr Cys
    1490

<210> SEQ ID NO 6
<211> LENGTH: 4296
<212> TYPE: DNA
<213> ORGANISM: Homo sapiens

<400> SEQUENCE: 6
atgagtgaaa aaaaattgga acaactgca cagcagcgga atgtcctga atggatgaat    60 gtgcagaata aagatgtgc tgtagaagaa agaaaggcat gtgttcggaa gagtgttttt   120
gaagatgacc tccccttctt agaattcact ggatccattg tgtatagtta cgatgctagt   180

```
gattgctctt tcctgtcaga agatattagc atgagtctat cagatgggga tgtggtggga      240
tttgacatgg agtggccacc attatacaat agagggaaac ttggcaaagt tgcactaatt      300
cagttgtgtg tttctgagag caaatgttac ttgttccacg tttcttccat gtcagttttt      360
ccccagggat taaaaatgtt gcttgaaaat aaagcagtta aaaaggcagg tgtaggaatt      420
gaaggagatc agtggaaact tctacgtgac tttgatatca aattgaagaa ttttgtggag      480
ttgacagatg ttgccaataa aaagctgaaa tgcacagaga cctggagcct taacagtctg      540
gttaaacacc tcttaggtaa acagctcctg aaagacaagt ctatccgctg tagcaattgg      600
agtaaatttc ctctcactga ggaccagaaa ctgtatgcag ccactgatgc ttatgctggt      660
tttattattt accgaaattt agagattttg gatgatactg tgcaaaggtt tgctataaat      720
aaagaggaag aaatcctact tagcgacatg aacaaacagt tgacttcaat ctctgaggaa      780
gtgatggatc tggctaagca tcttcctcat gctttcagta aattggaaaa cccacggagg      840
gtttctatct tactaaagga tatttcgaaa aatctatatt cactgaggag gatgataatt      900
gggtctacta acattgagac tgaactgagg cccagcaata atttaaactt attatccttt      960
gaagattcaa ctactggggg agtacaacag aaacaaatta gagaacatga gttttaatt     1020 cacgttgaag atgaaacatg ggacccaaca cttgatcatt tagctaaaca tgatggagaa     1080
gatgtacttg gaaataaagt ggaacgaaaa gaagatggat ttgaagatgg agtagaagac     1140
aacaaattga agagaatat ggaaagagct tgtttgatgt cgttagatat tacagaacat     1200
gaactccaaa ttttggaaca gcagtctcag gaagaatatc ttagtgatat tgcttataaa     1260
tctactgagc atttatctcc caatgataat gaaaacgata cgtcctatgt aattgagagt     1320
gatgaagatt tagaaatgga gatgcttaag catttatctc ccaatgataa tgaaaacgat     1380
acgtcctatg taattgagag tgatgaagat ttagaaatgg agatgcttaa gtctttagaa     1440
aacctcaata gtggcacggt agaaccaact cattctaaat gcttaaaaat ggaaagaaat     1500
ctgggtcttc ctactaaaga agaagaagaa gatgatgaaa atgaagctaa tgaaggggaa     1560
gaagatgatg ataaggactt tttgtggcca gcacccaatg aagagcaagt tacttgcctc     1620
aagatgtact ttggccattc cagttttaaa ccagttcagt ggaaagtgat tcattcagta     1680
ttagaagaaa gaagagataa tgttgctgtc atggcaactg gatatggaaa gagtttgtgc     1740
ttccagtatc cacctgttta tgtaggcaag attggccttg ttatctctcc ccttatttct     1800
ctgatggaag accaagtgct acagcttaaa atgtccaaca tcccagcttg cttccttgga     1860
tcagcacagt cagaaaatgt tctaacagat attaaattag gtaaataccg gattgtatac     1920
gtaactccag aatactgttc aggtaacatg ggcctgctcc agcaacttga ggctgatatt     1980
ggtatcacgc tcattgctgt ggatgaggct cactgtattt ctgagtgggg gcatgatttt     2040
agggattcat tcaggaagtt gggctcccta agacagcac tgccaatggt tccaatcgtt     2100
gcacttactg ctattgcaag ttcttcaatc cgggaagaca ttgtacgttg cttaaatctg     2160
agaaatcctc agatcacctg tactggtttt gatcgaccaa acctgtattt agaagttagg     2220
cgaaaaacag ggaatatcct tcaggatctg cagccatttc ttgtcaaaac aagttcccac     2280
tgggaatttg aaggtccaac aatcatctac tgtccttcta gaaaaatgac acaacaagtt     2340
acaggtgaac ttaggaaact gaatctatcc tgtgaacat accatgcggg catgagtttt     2400
agcacaagga agacattca tcataggttt gtaagagatg aaattcagtg tgtcatagct     2460
accatagctt ttggaatggg cattaataaa gctgacattc gccaagtcat tcattacggt     2520
gctcctaagg acatggaatc atattatcag gagattggta gagctggtcg tgatggactt     2580
```

```
caaagttctt gtcacgtcct ctgggctcct gcagacatta acttaaatag gcaccttctt   2640
actgagatac gtaatgagaa gtttcgatta tacaaattaa agatgatggc aaagatggaa   2700
aaatatcttc attctagcag atgtaggaga caaatcatct tgtctcattt tgaggacaaa   2760
caagtacaaa aagcctcctt gggaattatg ggaactgaaa aatgctgtga taattgcagg   2820
tccagattgg atcattgcta ttccatggat gactcagagg atacatcctg gactttggt    2880 ccacaagcat ttaagctttt gtctgctgtg acatcttag gcgaaaaatt tggaattggg    2940
cttccaattt tatttctccg aggatctaat tctcagcgtc ttgccgatca atatcgcagg   3000
cacagtttat ttggcactgg caaggatcaa acagagagtt ggtggaaggc ttttccccgt    3060
cagctgatca ctgagggatt cttggtagaa gttctcggt ataacaaatt tatgaagatt    3120 tgcgcccttta cgaaaaaggg tagaaaattgg cttcataaag ctaatacaga atctcagagc   3180
ctcatccttc aagctaatga agaattgtgt ccaaagaagt tgcttctgcc tagttcgaaa   3240
actgtatctt cgggcaccaa agagcattgt tataatcaag taccagttga attaagtaca   3300
gagaagaagt ctaacttgga gaagttatat tcttataaac catgtgataa gatttcttct   3360
gggagtaaca tttctaaaaa aagtatcatg gtacagtcac cagaaaaagc ttacagttcc   3420
tcacagcctg ttatttcggc acaagagcag gagactcaga ttgtgttata tggcaaattg   3480
gtagaagcta ggcagaaaca tgccaataaa atggatgttc ccccagctat tctggcaaca   3540
aacaagatac tggtggatat ggccaaaatg agaccaacta cggttgaaaa cgtaaaaagg   3600
attgatggtg tttctgaagg caaagctgcc atgttggccc ctctgttgga agtcatcaaa   3660
catttctgcc aaacaaatag tgttcagaca gacctctttt caagtacaaa acctcaagaa   3720
gaacagaaga cgagtctggt agcaaaaaat aaaatatgca cactttcaca gtctatggcc   3780
atcacatact ctttattcca agaaaagaag atgcctttga gagcatagc tgagagcagg    3840 attctgcctc tcatgacaat tggcatgcac ttatcccaag cggtgaaagc tggctgcccc   3900
cttgatttgg agcgagcagg cctgactcca gaggttcaga agattattgc tgatgttatc   3960
cgaaaccctc ccgtcaactc agatatgagt aaaattagcc taatcagaat gttagttcct   4020
gaaaacattg acacgtacct tatccacatg gcaattgaga tccttaaaca tggtcctgac   4080
agcggacttc aaccttcatg tgatgtcaac aaaaggagat gttttcccgg ttctgaagag   4140
atctgttcaa gttctaagag aagcaaggaa gaagtaggca tcaatactga gacttcatct   4200
gcagagagaa agagacgatt acctgtgtgg tttgccaaag gaagtgatac cagcaagaaa   4260
ttaatggaca aaacgaaaag gggaggtctt tttagt                              4296

<210> SEQ ID NO 7
<211> LENGTH: 4296
<212> TYPE: DNA
<213> ORGANISM: Homo sapiens

<400> SEQUENCE: 7
atgagtgaaa aaaaattgga acaactgca cagcagcgga aatgtcctga atggatgaat   60
gtgcagaata aagatgtgc tgtagaagaa agaaaggcat gtgttcggaa gagtgttttt   120
gaagatgacc tccccttctt agaattcact ggatccattg tgtatagtta cgatgctagt   180
gattgctctt tcctgtcaga agatattagc atgagtctat cagatgggga tgtggtggga   240
tttgacatgg agtggccacc attatacaat agagggaaac ttggcaaagt tgcactaatt   300
cagttgtgtg tttctgagag caaatgttac ttgttccacg tttcttccat gtcagttttc   360
```

```
ccccagggat taaaaatgtt gcttgaaaat aaagcagtta aaaaggcagg tgtaggaatt      420
gaaggagatc agtggaaact tctacgtgac tttgatatca aattgaagaa ttttgtggag      480
ttgacagatg ttgccaataa aaagctgaaa tgcacagaga cctggagcct aacagtctg      540 gttaaacacc tcttaggtaa acagctcctg aaagacaagt ctatccgctg tagcaattgg      600
agtaaatttc ctctcactga ggaccagaaa ctgtatgcag ccactgatgc ttatgctggt      660
tttattattt accgaaattt agagattttg gatgatactg tgcaaaggtt tgctataaat      720
aaagaggaag aaatcctact tagcgacatg aacaaacagt tgacttcaat ctctgaggaa      780
gtgatggatc tggctaagca tcttcctcat gctttcagta aattggaaaa cccacggagg      840
gtttctatct tactaaagga tatttcagaa aatctatatt cactgaggag gatgataatt      900
gggtctacta acattgagac tgaactgagg cccagcaata atttaaactt attatccttt      960
gaagattcaa ctactggggg agtacaacag aaacaaatta gagaacatga agttttaatt     1020
cacgttgaag atgaaacatg ggacccaaca cttgatcatt tagctaaaca tgatggagaa     1080
gatgtacttg gaaataaagt ggaacgaaaa gaagatggat tgaagatgg agtagaagac      1140 aacaaattga agagaatat ggaaagagct gtttgatgt cgttagatat tacagaacat       1200
gaactccaaa ttttggaaca gcagtctcag gaagaatatc ttagtgatat tgcttataaa     1260
tctactgagc atttatctcc caatgataat gaaaacgata cgtcctatgt aattgagagt     1320
gatgaagatt tagaaatgga gatgcttaag catttatctc ccaatgataa tgaaaacgat     1380
acgtcctatg taattgagag tgatgaagat ttagaaatgg agatgcttaa gtctttagaa     1440
aacctcaata gtggcacggt agaaccaact cattctaaat gcttaaaaat ggaaagaaat     1500
ctgggtcttc ctactaaaga agaagaagaa gatgatgaaa atgaagctaa tgaaggggaa     1560
gaagatgatg ataaggactt tttgtggcca gcacccaatg aagagcaagt tacttgcctc     1620
aagatgtact ttggccattc cagttttaaa ccagttcagt ggaaagtgat tcattcagta     1680
ttagaagaaa gaagagataa tgttgctgtc atggcaactg gatatggaaa gagtttgtgc     1740
ttccagtatc cacctgttta tgtaggcaag attggccttg ttatctctcc ccttatttct     1800 ctgatgaag accaagtgct acagcttaaa atgtccaaca tcccagcttg cttccttgga     1860
tcagcacagt cagaaaatgt tctaacagat attaaattag gtaaataccg gattgtatac     1920
gtaactccag aatactgttc aggtaacatg ggcctgctcc agcaacttga ggctgatatt     1980
ggtatcacgc tcattgctgt ggatgaggct cactgtattt ctgagtgggg gcatgatttt     2040
agggattcat tcaggaagtt gggctcccta aagacagcac tgccaatggt tccaatcgtt     2100
gcacttactg ctactgcaag ttcttcaatc cgggaagaca ttgtacgttg cttaaatctg     2160
agaaatcctc agatcacctg tactggtttt gatcgaccaa acctgtattt agaagttagg     2220
cgaaaaacag ggaatatcct tcaggatctg cagccatttc ttgtcaaaac aagttcccac     2280
tgggaatttg aaggtccaac aatcatctac tgtccttcta gaaaaatgac acaacaagtt     2340
acaggtgaac ttaggaaact gaatctatcc tgtggaacat accatgcggg catgagtttt     2400
agcacaagga agacattca tcataggttt gtaagagatg aaattcagtg tgtcatagct      2460
accatagctt ttggaatggg cattaataaa gctgacattc gccaagtcat tcattacggt     2520
gctcctaagg acatggaatc atattatcag gagattggta gagctggtcg tgatggactt     2580
caaagttctt gtcacgtcct ctgggctcct gcagacatta acttaaatag gcaccttctt     2640
actgagatac gtaatgagaa gtttcgatta tacaaattaa agatgatggc aaagatggaa     2700
aaatatcttc attctagcag atgtaggaga caaatcatct tgtctcattt tgaggacaaa     2760
```

| | |
|---|---|
| caagtacaaa aagcctcctt gggaattatg ggaactgaaa aatgctgtga taattgcagg | 2820 |
| tccagattgg atcattgcta ttccatggat gactcagagg atacatcctg ggactttggt | 2880 |
| ccacaagcat ttaagctttt gtctgctgtg gacatcttag gcgaaaaatt tggaattggg | 2940 |
| cttccaattt tatttctccg aggatctaat tctcagcgtc ttgccgatca atatcgcagg | 3000 |
| cacagtttat ttggcactgg caaggatcaa acagagagtt ggtggaaggc ttttttcccgt | 3060 |
| cagctgatca ctgagggatt cttggtagaa gtttctcggt ataacaaatt tatgaagatt | 3120 |
| tgcgcccta cgaaaaaggg tagaaattgg cttcataaag ctaatacaga atctcagagc | 3180 |
| ctcatccttc aagctaatga agaattgtgt ccaaagaagt tgcttctgcc tagttcgaaa | 3240 |
| actgtatctt cgggcaccaa agagcattgt taatcaag taccagttga attaagtaca | 3300 |
| gagaagaagt ctaacttgga gaagttatat tcttataaac catgtgataa gatttcttct | 3360 |
| gggagtaaca tttctaaaaa aagtatcatg gtacagtcac cagaaaaagc ttacagttcc | 3420 |
| tcacagcctg ttatttcggc acaagagcag gagactcaga ttgtgttata tggcaaattg | 3480 |
| gtagaagcta ggcagaaaca tgccaataaa atggatgttc ccccagctat tctggcaaca | 3540 |
| aacaagatac tggtggatat ggccaaaatg agaccaacta cggttgaaaa cgtaaaaagg | 3600 |
| attgatggtg tttctgaagg caaagctgcc atgttggccc ctctgttgga agtcatcaaa | 3660 |
| catttctgcc aaacaaatag tgttcagaca gacctcttt caagtacaaa acctcaagaa | 3720 |
| gaacagaaga cgagtctggt agcaaaaaat aaaatatgca cactttcaca gtctatggcc | 3780 |
| atcacatact cttattcca agaaaagaag atgcctttga agagcatagc tgagagcagg | 3840 |
| attctgcctc tcatgacaat tggcatgcac ttatcccaag cggtgaaagc tggctgcccc | 3900 |
| cttgatttgg agcgagcagg cctgactcca gaggttcaga agattattgc tgatgttatc | 3960 |
| cgaaaccctc ccgtcaactc agatatgagt aaaaattagcc taatcagaat gttagttcct | 4020 |
| gaaaacattg acacgtacct tatccacatg gcaattgaga tccttaaaca tggtcctgac | 4080 |
| agcggacttc aaccttcatg tgatgtcaac aaaaggagat gttttcccgg ttctgaagag | 4140 |
| atctgttcaa gttctaagag aagcaaggaa gaagtaggca tcaatactga gacttcatct | 4200 |
| gcagagagaa agagacgatt acctgtgtgg tttgccaaag gaagtgatac cagcaagaaa | 4260 |
| ttaatggaca aaacgaaaag gggaggtctt tttagt | 4296 |

<210> SEQ ID NO 8
<211> LENGTH: 5765
<212> TYPE: DNA
<213> ORGANISM: Homo sapiens

<400> SEQUENCE: 8

| | |
|---|---|
| cagccgcccc tcctgcggcc gctgcggggg ccgccgcctg acttcggaca ccggccccgc | 60 |
| acccgccagg aggggaggga aggggaggcg gggagagcga cggcgggggg cgggcggtgg | 120 |
| accccgcctc ccccggcaca gcctgctgag gggaagaggg ggtctccgct cttcctcagt | 180 |
| gcactctctg actgaagccc ggcgcgtggg gtgcagcggg agtgcgaggg gactggacag | 240 |
| gtgggaagat gggaatgagg accggcggc gggaatgttc tcacttctcc ggattccacc | 300 |
| gggatgcagg actctagctg cccagccgca cctgcgaaga gactacactt cccgaggtgc | 360 |
| tcagcggcag cgagggcctc cacgcatgcg caccgcggcg cgctgggcgg ggctggatgg | 420 |
| gctgtggtgg gagggttgca gcgccgcgag aaaggcgagc cggccggggg gcggggaaag | 480 |
| gggtgggggca ggaacggggg cggggacggc gctggagggg cgggtcgggt aggtctcccg | 540 |

-continued

```
gagctgatgt gtactgtgtg cgccggggag gcgccggctt gtactcggca gcgcgggaat    600
aaagtttgct gatttggtgt ctagcctgga tgcctgggtt gcaggccctg cttgtggtgg    660
cgctccacag tcatccggct gaagaagacc tgttggactg gatcttctcg ggttttcttt    720
cagatattgt tttgtattta cccatgaaga cattgttttt tggactctgc aaataggaca    780
tttcaaagat gagtgaaaaa aaattggaaa caactgcaca gcagcggaaa tgtcctgaat    840
ggatgaatgc gcagaataaa agatgtgctg tagaagaaag aaaggcatgt gttcggaaga    900 gtgttttga agatgaccctc cccttcttag aattcactgg atccattgtg tatagttacg    960
atgctagtga ttgctctttc ctgtcagaag atattagcat gagtctatca gatggggatg    1020
tggtgggatt tgacatggag tggccaccat tatacaatag agggaaactt ggcaaagttg    1080
cactaattca gttgtgtgtt tctgagagca atgttactt gttccacgtt tcttccatgt    1140 cagttttcc ccagggatta aaaatgttgc ttgaaaataa agcagttaaa aaggcaggtg    1200
taggaattga aggagatcag tggaaacttc tacgtgactt tgatatcaaa ttgaagaatt    1260
ttgtggagtt gacagatgtt gccaataaaa agctgaaatg cacagagacc tggagcctta    1320
acagtctggt taaacacctc ttaggtaaac agctcctgaa agacaagtct atccgctgta    1380
gcaattggag taaatttcct ctcactgagg accagaaact gtatgcagcc actgatgctt    1440
atgctggttt tattatttac cgaaatttag agattttgga tgatactgtg caaaggtttg    1500
ctataaataa agaggaagaa atcctactta gcgacatgaa caaacagttg acttcaatct    1560
ctgaggaagt gatggatctg gctaagcatc ttcctcatgc tttcagtaaa ttggaaaacc    1620 cacgagggt ttctatctta ctaaaggata tttcagaaaa tctatattca ctgaggagga    1680
tgataattgg gtctactaac attgagactg aactgaggcc cagcaataat ttaaacttat    1740
tatcctttga agattcaact actggggagt acaacagaa acaaattaga gaacatgaag    1800
ttttaattca cgttgaagat gaaacatggg acccaacact tgatcattta gctaaacatg    1860
atggagaaga tgtacttgga aataaagtgg aacgaaaaga gatggatttt gaagatggag    1920
tagaagacaa caaattgaaa gagaatatgg aaagagcttg tttgatgtcg ttagatatta    1980
cagaacatga actccaaatt ttggaacagc agtctcagga agaatatctt agtgatattg    2040
cttataaatc tactgagcat ttatctccca atgataatga aaacgatacg tcctatgtaa    2100
ttgagagtga tgaagattta gaatggagac tgcttaagca tttatctccc aatgataatg    2160
aaaacgatac gtcctatgta attgagagtg atgaagattt agaaatggag atgcttaagt    2220
ctttagaaaa cctcaatagt ggcacggtag aaccaactca ttctaaatgc ttaaaaatgg    2280
aaagaaatct gggtcttcct actaaagaag aagaagaaga tgatgaaaat gaagctaatg    2340 aagggggaaga agatgatgat aaggactttt gtggccagc acccaatgaa gagcaagtta    2400
cttgcctcaa gatgtacttt ggccattcca gtttaaacc agttcagtgg aaagtgattc    2460
attcagtatt agaagaaaga agagataatg ttgctgtcat ggcaactgga tatgaaaga    2520 gtttgtgctt ccagtatcca cctgtttatg taggcaagat tggccttgtt atctctcccc    2580
ttatttctct gatggaagac caagtgctac agcttaaaat gtccaacatc ccagcttgct    2640
tccttggatc agcacagtca gaaaatgttc taacagatat taaattaggt aaataccgga    2700
ttgtatacgt aactccagaa tactgttcag gtaacatggg cctgctccag caacttgagg    2760
ctgatattgg tatcacgctc attgctgtgg atgaggctca ctgtatttct gagtgggggc    2820 atgatttag ggattcattc aggaagttgg gctccctaaa gacagcactg ccaatggttc    2880
caatcgttgc acttactgct actgcaagtt cttcaatccg ggaagacatt gtacgttgct    2940
```

```
taaatctgag aaatcctcag atcacctgta ctggttttga tcgaccaaac ctgtatttag  3000
aagttaggcg aaaaacaggg aatatccttc aggatctgca gccatttctt gtcaaaacaa  3060
gttcccactg ggaatttgaa ggtccaacaa tcatctactg tccttctaga aaaatgacac  3120
aacaagttac aggtgaactt aggaaactga atctatcctg tggaacatac catgcgggca  3180
tgagttttag cacaaggaaa gacattcatc ataggtttgt aagagatgaa attcagtgtg  3240
tcatagctac catagctttt ggaatgggca ttaataaagc tgacattcgc caagtcattc  3300
attacggtgc tcctaaggac atggaatcat attatcagga gattggtaga gctggtcgtg  3360
atggacttca aagttcttgt cacgtcctct gggctcctgc agacattaac ttaaataggc  3420
accttcttac tgagatacgt aatgagaagt ttcgattata caaattaaag atgatggcaa  3480
agatggaaaa atatcttcat tctagcagat gtaggagaca aatcatcctg tctcattttg  3540
aggacaaaca agtacaaaaa gcctccttgg gaattatggg aactgaaaaa tgctgtgata  3600
attgcaggtc cagattggat cattgctatt ccatggatga ctcagaggat acatcctggg  3660
actttggtcc acaagcattt aagcttttgt ctgctgtgga catcttaggc gaaaaatttg  3720
gaattgggct tccaattta tttctccgag gatctaattc tcagcgtctt gccgatcaat  3780
atcgcaggca cagtttattt ggcactggca aggatcaaac agagagttgg tggaaggctt  3840
tttcccgtca gctgatcact gagggattct tggtagaagt ttctcggtat aacaaattta  3900
tgaagatttg cgcccttacg aaaaagggta gaaattggct tcataaagct aatacagaat  3960
ctcagagcct catccttcaa gctaatgaag aattgtgtcc aaagaagttg cttctgccta  4020
gttcgaaaac tgtatcttcg ggcaccaaag agcattgtta taatcaagta ccagttgaat  4080
taagtacaga gaagaagtct aacttggaga agttatattc ttataaacca tgtgataaga  4140
tttcttctgg gagtaacatt tctaaaaaaa gtatcatggt acagtcacca gaaaaagctt  4200
acagttcctc acagcctgtt atttcggcac aagagcagga gactcagatt gtgttatatg  4260
gcaaattggt agaagctagg cagaaacatg ccaataaaat ggatgttccc ccagctattc  4320
tggcaacaaa caagatactg gtggatatgg ccaaaatgag accaactacg gttgaaaacg  4380
taaaaaggat tgatggtgtt tctgaaggca agctgccat gttggcccct ctgttggaag  4440
tcatcaaaca tttctgccaa acaaatagtg ttcagacaga cctcttttca agtacaaaac  4500
ctcaagaaga acagaagacg agtctggtag caaaaaataa aatatgcaca ctttcacagt  4560
ctatggccat cacatactct ttattccaag aaaagaagat gcctttgaag agcatagctg  4620
agagcaggat tctgcctctc atgacaattg gcatgcactt atcccaagcg gtgaaagctg  4680
gctgccccct tgatttggag cgagcaggcc tgactccaga ggttcagaag attattgctg  4740
atgttatccg aaaccctccc gtcaactcag atatgagtaa aattagccta atcagaatgt  4800
tagttcctga aaacattgac acgtaccttta tccacatggc aattgagatc cttaaacatg  4860
gtcctgacag cggacttcaa ccttcatgtg atgtcaacaa aaggagatgt tttcccggtt  4920
ctgaagagat ctgttcaagt tctaagagaa gcaaggaaga agtaggcatc aatactgaga  4980
cttcatctgc agagagaaag agacgattac ctgtgtggtt tgccaaagga agtgatacca  5040
gcaagaaatt aatggacaaa acgaaaaggg gaggtctttt tagttaagct ggcaattacc  5100
agaacaatta tgtttcttgc tgtattataa gaggatagct atatttatt tctgaagagt  5160 aaggagtagt attttggctt aaaaatcatt ctaattacaa agttcactgt ttattgaaga  5220
actggcatct taaatcagcc ttccgcaatt catgtagttt ctgggtcttc tgggagccta  5280
```

-continued

```
cgtgagtaca tcacctaaca gaatattaaa ttagacttcc tgtaagattg ctttaagaaa   5340
ctgttactgt cctgttttct aatctcttta ttaaaacagt gtatttggaa aatgttatgt   5400
gctctgattt gatatagata acagattagt agttacatgg taattatgtg atataaaata   5460
ttcatatatt atcaaaattc tgttttgtaa atgtaagaaa gcatagttat tttacaaatt   5520
gttttactg  tcttttgaag aagttcttaa atacgttgtt aaatggtatt agttgaccag   5580
ggcagtgaaa atgaaaccgc attttgggtg ccattaaata gggaaaaaac atgtaaaaaa   5640
tgtaaaatgg agaccaattg cactaggcaa gtgtatattt tgtattttat atacaatttc   5700
tattattttt caagtaataa aacaatgttt ttcatactga atattaaaaa aaaaaaaaa   5760
aaaaa                                                                5765
```

<210> SEQ ID NO 9
<211> LENGTH: 1432
<212> TYPE: PRT
<213> ORGANISM: Homo sapiens

<400> SEQUENCE: 9

```
Met Ser Glu Lys Lys Leu Glu Thr Thr Ala Gln Gln Arg Lys Cys Pro
1               5                   10                  15

Glu Trp Met Asn Val Gln Asn Lys Arg Cys Ala Val Glu Glu Arg Lys
            20                  25                  30

Ala Cys Val Arg Lys Ser Val Phe Glu Asp Asp Leu Pro Phe Leu Glu
        35                  40                  45

Phe Thr Gly Ser Ile Val Tyr Ser Tyr Asp Ala Ser Asp Cys Ser Phe
    50                  55                  60

Leu Ser Glu Asp Ile Ser Met Ser Leu Ser Asp Gly Asp Val Val Gly
65                  70                  75                  80

Phe Asp Met Glu Trp Pro Pro Leu Tyr Asn Arg Gly Lys Leu Gly Lys
                85                  90                  95

Val Ala Leu Ile Gln Leu Cys Val Ser Glu Ser Lys Cys Tyr Leu Phe
            100                 105                 110

His Val Ser Ser Met Ser Val Phe Pro Gln Gly Leu Lys Met Leu Leu
        115                 120                 125

Glu Asn Lys Ala Val Lys Lys Ala Gly Val Gly Ile Glu Gly Asp Gln
    130                 135                 140

Trp Lys Leu Leu Arg Asp Phe Asp Ile Lys Leu Lys Asn Phe Val Glu
145                 150                 155                 160

Leu Thr Asp Val Ala Asn Lys Lys Leu Lys Cys Thr Glu Thr Trp Ser
                165                 170                 175

Leu Asn Ser Leu Val Lys His Leu Leu Gly Lys Gln Leu Leu Lys Asp
            180                 185                 190

Lys Ser Ile Arg Cys Ser Asn Trp Ser Lys Phe Pro Leu Thr Glu Asp
        195                 200                 205

Gln Lys Leu Tyr Ala Ala Thr Asp Ala Tyr Ala Gly Phe Ile Ile Tyr
    210                 215                 220

Arg Asn Leu Glu Ile Leu Asp Asp Thr Val Gln Arg Phe Ala Ile Asn
225                 230                 235                 240

Lys Glu Glu Glu Ile Leu Leu Ser Asp Met Asn Lys Gln Leu Thr Ser
                245                 250                 255

Ile Ser Glu Glu Val Met Asp Leu Ala Lys His Leu Pro His Ala Phe
            260                 265                 270

Ser Lys Leu Glu Asn Pro Arg Arg Val Ser Ile Leu Leu Lys Asp Ile
        275                 280                 285
```

```
Ser Glu Asn Leu Tyr Ser Leu Arg Arg Met Ile Ile Gly Ser Thr Asn
    290                 295                 300

Ile Glu Thr Glu Leu Arg Pro Ser Asn Asn Leu Asn Leu Leu Ser Phe
305                 310                 315                 320

Glu Asp Ser Thr Thr Gly Gly Val Gln Gln Lys Gln Ile Arg Glu His
                325                 330                 335

Glu Val Leu Ile His Val Glu Asp Glu Thr Trp Asp Pro Thr Leu Asp
            340                 345                 350

His Leu Ala Lys His Asp Gly Glu Asp Val Leu Gly Asn Lys Val Glu
        355                 360                 365

Arg Lys Glu Asp Gly Phe Glu Asp Gly Val Glu Asp Asn Lys Leu Lys
    370                 375                 380

Glu Asn Met Glu Arg Ala Cys Leu Met Ser Leu Asp Ile Thr Glu His
385                 390                 395                 400

Glu Leu Gln Ile Leu Glu Gln Gln Ser Gln Glu Glu Tyr Leu Ser Asp
                405                 410                 415

Ile Ala Tyr Lys Ser Thr Glu His Leu Ser Pro Asn Asp Asn Glu Asn
            420                 425                 430

Asp Thr Ser Tyr Val Ile Glu Ser Asp Glu Asp Leu Glu Met Glu Met
        435                 440                 445

Leu Lys His Leu Ser Pro Asn Asp Asn Glu Asn Asp Thr Ser Tyr Val
    450                 455                 460

Ile Glu Ser Asp Glu Asp Leu Glu Met Glu Met Leu Lys Ser Leu Glu
465                 470                 475                 480

Asn Leu Asn Ser Gly Thr Val Glu Pro Thr His Ser Lys Cys Leu Lys
                485                 490                 495

Met Glu Arg Asn Leu Gly Leu Pro Thr Lys Glu Glu Glu Asp Asp
            500                 505                 510

Glu Asn Glu Ala Asn Glu Gly Glu Asp Asp Lys Asp Phe Leu
        515                 520                 525

Trp Pro Ala Pro Asn Glu Glu Gln Val Thr Cys Leu Lys Met Tyr Phe
    530                 535                 540

Gly His Ser Ser Phe Lys Pro Val Gln Trp Lys Val Ile His Ser Val
545                 550                 555                 560

Leu Glu Glu Arg Arg Asp Asn Val Ala Val Met Ala Thr Gly Tyr Gly
                565                 570                 575

Lys Ser Leu Cys Phe Gln Tyr Pro Pro Val Tyr Val Gly Lys Ile Gly
            580                 585                 590

Leu Val Ile Ser Pro Leu Ile Ser Leu Met Glu Asp Gln Val Leu Gln
        595                 600                 605

Leu Lys Met Ser Asn Ile Pro Ala Cys Phe Leu Gly Ser Ala Gln Ser
    610                 615                 620

Glu Asn Val Leu Thr Asp Ile Lys Leu Gly Lys Tyr Arg Ile Val Tyr
625                 630                 635                 640

Val Thr Pro Glu Tyr Cys Ser Gly Asn Met Gly Leu Leu Gln Gln Leu
                645                 650                 655

Glu Ala Asp Ile Gly Ile Thr Leu Ile Ala Val Asp Glu Ala His Cys
            660                 665                 670

Ile Ser Glu Trp Gly His Asp Phe Arg Asp Ser Phe Arg Lys Leu Gly
        675                 680                 685

Ser Leu Lys Thr Ala Leu Pro Met Val Pro Ile Val Ala Leu Thr Ala
    690                 695                 700
```

```
Ile Ala Ser Ser Ser Ile Arg Glu Asp Ile Val Arg Cys Leu Asn Leu
705                 710                 715                 720

Arg Asn Pro Gln Ile Thr Cys Thr Gly Phe Asp Arg Pro Asn Leu Tyr
            725                 730                 735

Leu Glu Val Arg Arg Lys Thr Gly Asn Ile Leu Gln Asp Leu Gln Pro
                740                 745                 750

Phe Leu Val Lys Thr Ser Ser His Trp Glu Phe Glu Gly Pro Thr Ile
            755                 760                 765

Ile Tyr Cys Pro Ser Arg Lys Met Thr Gln Gln Val Thr Gly Glu Leu
770                 775                 780

Arg Lys Leu Asn Leu Ser Cys Gly Thr Tyr His Ala Gly Met Ser Phe
785                 790                 795                 800

Ser Thr Arg Lys Asp Ile His His Arg Phe Val Arg Asp Glu Ile Gln
                805                 810                 815

Cys Val Ile Ala Thr Ile Ala Phe Gly Met Gly Ile Asn Lys Ala Asp
                820                 825                 830

Ile Arg Gln Val Ile His Tyr Gly Ala Pro Lys Asp Met Glu Ser Tyr
                835                 840                 845

Tyr Gln Glu Ile Gly Arg Ala Gly Arg Asp Gly Leu Gln Ser Ser Cys
850                 855                 860

His Val Leu Trp Ala Pro Ala Asp Ile Asn Leu Asn Arg His Leu Leu
865                 870                 875                 880

Thr Glu Ile Arg Asn Glu Lys Phe Arg Leu Tyr Lys Leu Lys Met Met
                885                 890                 895

Ala Lys Met Glu Lys Tyr Leu His Ser Ser Arg Cys Arg Arg Gln Ile
                900                 905                 910

Ile Leu Ser His Phe Glu Asp Lys Gln Val Gln Lys Ala Ser Leu Gly
                915                 920                 925

Ile Met Gly Thr Glu Lys Cys Cys Asp Asn Cys Arg Ser Arg Leu Asp
930                 935                 940

His Cys Tyr Ser Met Asp Asp Ser Glu Asp Thr Ser Trp Asp Phe Gly
945                 950                 955                 960

Pro Gln Ala Phe Lys Leu Leu Ser Ala Val Asp Ile Leu Gly Glu Lys
                965                 970                 975

Phe Gly Ile Gly Leu Pro Ile Leu Phe Leu Arg Gly Ser Asn Ser Gln
                980                 985                 990

Arg Leu Ala Asp Gln Tyr Arg Arg His Ser Leu Phe Gly Thr Gly Lys
                995                 1000                1005

Asp Gln Thr Glu Ser Trp Trp Lys Ala Phe Ser Arg Gln Leu Ile
1010                1015                1020

Thr Glu Gly Phe Leu Val Glu Val Ser Arg Tyr Asn Lys Phe Met
1025                1030                1035

Lys Ile Cys Ala Leu Thr Lys Lys Gly Arg Asn Trp Leu His Lys
1040                1045                1050

Ala Asn Thr Glu Ser Gln Ser Leu Ile Leu Gln Ala Asn Glu Glu
1055                1060                1065

Leu Cys Pro Lys Lys Leu Leu Pro Ser Ser Lys Thr Val Ser
1070                1075                1080

Ser Gly Thr Lys Glu His Cys Tyr Asn Gln Val Pro Val Glu Leu
1085                1090                1095

Ser Thr Glu Lys Lys Ser Asn Leu Glu Lys Leu Tyr Ser Tyr Lys
1100                1105                1110

Pro Cys Asp Lys Ile Ser Ser Gly Ser Asn Ile Ser Lys Lys Ser
```

```
            1115                1120                1125

Ile Met Val Gln Ser Pro Glu Lys Ala Tyr Ser Ser Ser Gln Pro
    1130                1135                1140

Val Ile Ser Ala Gln Glu Gln Thr Gln Ile Val Leu Tyr Gly
    1145                1150                1155

Lys Leu Val Glu Ala Arg Gln Lys His Ala Asn Lys Met Asp Val
    1160                1165                1170

Pro Pro Ala Ile Leu Ala Thr Asn Lys Ile Leu Val Asp Met Ala
    1175                1180                1185

Lys Met Arg Pro Thr Thr Val Glu Asn Val Lys Arg Ile Asp Gly
    1190                1195                1200

Val Ser Glu Gly Lys Ala Ala Met Leu Ala Pro Leu Leu Glu Val
    1205                1210                1215

Ile Lys His Phe Cys Gln Thr Asn Ser Val Gln Thr Asp Leu Phe
    1220                1225                1230

Ser Ser Thr Lys Pro Gln Glu Glu Gln Lys Thr Ser Leu Val Ala
    1235                1240                1245

Lys Asn Lys Ile Cys Thr Leu Ser Gln Ser Met Ala Ile Thr Tyr
    1250                1255                1260

Ser Leu Phe Gln Glu Lys Lys Met Pro Leu Lys Ser Ile Ala Glu
    1265                1270                1275

Ser Arg Ile Leu Pro Leu Met Thr Ile Gly Met His Leu Ser Gln
    1280                1285                1290

Ala Val Lys Ala Gly Cys Pro Leu Asp Leu Glu Arg Ala Gly Leu
    1295                1300                1305

Thr Pro Glu Val Gln Lys Ile Ile Ala Asp Val Ile Arg Asn Pro
    1310                1315                1320

Pro Val Asn Ser Asp Met Ser Lys Ile Ser Leu Ile Arg Met Leu
    1325                1330                1335

Val Pro Glu Asn Ile Asp Thr Tyr Leu Ile His Met Ala Ile Glu
    1340                1345                1350

Ile Leu Lys His Gly Pro Asp Ser Gly Leu Gln Pro Ser Cys Asp
    1355                1360                1365

Val Asn Lys Arg Arg Cys Phe Pro Gly Ser Glu Glu Ile Cys Ser
    1370                1375                1380

Ser Ser Lys Arg Ser Lys Glu Glu Val Gly Ile Asn Thr Glu Thr
    1385                1390                1395

Ser Ser Ala Glu Arg Lys Arg Arg Leu Pro Val Trp Phe Ala Lys
    1400                1405                1410

Gly Ser Asp Thr Ser Lys Lys Leu Met Asp Lys Thr Lys Arg Gly
    1415                1420                1425

Gly Leu Phe Ser
    1430

<210> SEQ ID NO 10
<211> LENGTH: 1432
<212> TYPE: PRT
<213> ORGANISM: Homo sapiens

<400> SEQUENCE: 10

Met Ser Glu Lys Lys Leu Glu Thr Thr Ala Gln Gln Arg Lys Cys Pro
1               5                   10                  15

Glu Trp Met Asn Val Gln Asn Lys Arg Cys Ala Val Glu Glu Arg Lys
                20                  25                  30
```

```
Ala Cys Val Arg Lys Ser Val Phe Glu Asp Asp Leu Pro Phe Leu Glu
         35                  40                  45
Phe Thr Gly Ser Ile Val Tyr Ser Tyr Asp Ala Ser Asp Cys Ser Phe
 50                  55                  60
Leu Ser Glu Asp Ile Ser Met Ser Leu Ser Asp Gly Asp Val Val Gly
65                  70                  75                  80
Phe Asp Met Glu Trp Pro Pro Leu Tyr Asn Arg Gly Lys Leu Gly Lys
                 85                  90                  95
Val Ala Leu Ile Gln Leu Cys Val Ser Glu Ser Lys Cys Tyr Leu Phe
                100                 105                 110
His Val Ser Ser Met Ser Val Phe Pro Gln Gly Leu Lys Met Leu Leu
                115                 120                 125
Glu Asn Lys Ala Val Lys Lys Ala Gly Val Gly Ile Glu Gly Asp Gln
        130                 135                 140
Trp Lys Leu Leu Arg Asp Phe Asp Ile Lys Leu Lys Asn Phe Val Glu
145                 150                 155                 160
Leu Thr Asp Val Ala Asn Lys Lys Leu Lys Cys Thr Glu Thr Trp Ser
                165                 170                 175
Leu Asn Ser Leu Val Lys His Leu Leu Gly Lys Gln Leu Leu Lys Asp
                180                 185                 190
Lys Ser Ile Arg Cys Ser Asn Trp Ser Lys Phe Pro Leu Thr Glu Asp
        195                 200                 205
Gln Lys Leu Tyr Ala Ala Thr Asp Ala Tyr Ala Gly Phe Ile Ile Tyr
        210                 215                 220
Arg Asn Leu Glu Ile Leu Asp Asp Thr Val Gln Arg Phe Ala Ile Asn
225                 230                 235                 240
Lys Glu Glu Glu Ile Leu Leu Ser Asp Met Asn Lys Gln Leu Thr Ser
                245                 250                 255
Ile Ser Glu Glu Val Met Asp Leu Ala Lys His Leu Pro His Ala Phe
                260                 265                 270
Ser Lys Leu Glu Asn Pro Arg Arg Val Ser Ile Leu Leu Lys Asp Ile
        275                 280                 285
Ser Glu Asn Leu Tyr Ser Leu Arg Arg Met Ile Ile Gly Ser Thr Asn
        290                 295                 300
Ile Glu Thr Glu Leu Arg Pro Ser Asn Asn Leu Asn Leu Leu Ser Phe
305                 310                 315                 320
Glu Asp Ser Thr Thr Gly Gly Val Gln Gln Lys Gln Ile Arg Glu His
                325                 330                 335
Glu Val Leu Ile His Val Glu Asp Glu Thr Trp Asp Pro Thr Leu Asp
                340                 345                 350
His Leu Ala Lys His Asp Gly Glu Asp Val Leu Gly Asn Lys Val Glu
        355                 360                 365
Arg Lys Glu Asp Gly Phe Glu Asp Gly Val Glu Asp Asn Lys Leu Lys
        370                 375                 380
Glu Asn Met Glu Arg Ala Cys Leu Met Ser Leu Asp Ile Thr Glu His
385                 390                 395                 400
Glu Leu Gln Ile Leu Glu Gln Gln Ser Gln Glu Glu Tyr Leu Ser Asp
                405                 410                 415
Ile Ala Tyr Lys Ser Thr Glu His Leu Ser Pro Asn Asp Asn Glu Asn
        420                 425                 430
Asp Thr Ser Tyr Val Ile Glu Ser Asp Glu Asp Leu Glu Met Glu Met
        435                 440                 445
Leu Lys His Leu Ser Pro Asn Asp Asn Glu Asn Asp Thr Ser Tyr Val
```

```
              450                 455                 460
Ile Glu Ser Asp Glu Asp Leu Glu Met Glu Met Leu Lys Ser Leu Glu
465                 470                 475                 480

Asn Leu Asn Ser Gly Thr Val Glu Pro Thr His Ser Lys Cys Leu Lys
                485                 490                 495

Met Glu Arg Asn Leu Gly Leu Pro Thr Lys Glu Glu Glu Asp Asp
                500                 505                 510

Glu Asn Glu Ala Asn Glu Gly Glu Asp Asp Lys Asp Phe Leu
            515                 520                 525

Trp Pro Ala Pro Asn Glu Glu Gln Val Thr Cys Leu Lys Met Tyr Phe
530                 535                 540

Gly His Ser Ser Phe Lys Pro Val Gln Trp Lys Val Ile His Ser Val
545                 550                 555                 560

Leu Glu Glu Arg Arg Asp Asn Val Ala Val Met Ala Thr Gly Tyr Gly
                565                 570                 575

Lys Ser Leu Cys Phe Gln Tyr Pro Pro Val Tyr Val Gly Lys Ile Gly
                580                 585                 590

Leu Val Ile Ser Pro Leu Ile Ser Leu Met Glu Asp Gln Val Leu Gln
            595                 600                 605

Leu Lys Met Ser Asn Ile Pro Ala Cys Phe Leu Gly Ser Ala Gln Ser
        610                 615                 620

Glu Asn Val Leu Thr Asp Ile Lys Leu Gly Lys Tyr Arg Ile Val Tyr
625                 630                 635                 640

Val Thr Pro Glu Tyr Cys Ser Gly Asn Met Gly Leu Leu Gln Gln Leu
                645                 650                 655

Glu Ala Asp Ile Gly Ile Thr Leu Ile Ala Val Asp Glu Ala His Cys
            660                 665                 670

Ile Ser Glu Trp Gly His Asp Phe Arg Asp Ser Phe Arg Lys Leu Gly
        675                 680                 685

Ser Leu Lys Thr Ala Leu Pro Met Val Pro Ile Val Ala Leu Thr Ala
    690                 695                 700

Thr Ala Ser Ser Ser Ile Arg Glu Asp Ile Val Arg Cys Leu Asn Leu
705                 710                 715                 720

Arg Asn Pro Gln Ile Thr Cys Thr Gly Phe Asp Arg Pro Asn Leu Tyr
                725                 730                 735

Leu Glu Val Arg Arg Lys Thr Gly Asn Ile Leu Gln Asp Leu Gln Pro
                740                 745                 750

Phe Leu Val Lys Thr Ser Ser His Trp Glu Phe Glu Gly Pro Thr Ile
            755                 760                 765

Ile Tyr Cys Pro Ser Arg Lys Met Thr Gln Gln Val Thr Gly Glu Leu
770                 775                 780

Arg Lys Leu Asn Leu Ser Cys Gly Thr Tyr His Ala Gly Met Ser Phe
785                 790                 795                 800

Ser Thr Arg Lys Asp Ile His His Arg Phe Val Arg Asp Glu Ile Gln
                805                 810                 815

Cys Val Ile Ala Thr Ile Ala Phe Gly Met Gly Ile Asn Lys Ala Asp
                820                 825                 830

Ile Arg Gln Val Ile His Tyr Gly Ala Pro Lys Asp Met Glu Ser Tyr
            835                 840                 845

Tyr Gln Glu Ile Gly Arg Ala Gly Arg Asp Gly Leu Gln Ser Ser Cys
        850                 855                 860

His Val Leu Trp Ala Pro Ala Asp Ile Asn Leu Asn Arg His Leu Leu
865                 870                 875                 880
```

-continued

```
Thr Glu Ile Arg Asn Glu Lys Phe Arg Leu Tyr Lys Leu Lys Met Met
            885                 890                 895
Ala Lys Met Glu Lys Tyr Leu His Ser Ser Arg Cys Arg Arg Gln Ile
        900                 905                 910
Ile Leu Ser His Phe Glu Asp Lys Gln Val Gln Lys Ala Ser Leu Gly
            915                 920                 925
Ile Met Gly Thr Glu Lys Cys Cys Asp Asn Cys Arg Ser Arg Leu Asp
    930                 935                 940
His Cys Tyr Ser Met Asp Asp Ser Glu Asp Thr Ser Trp Asp Phe Gly
945                 950                 955                 960
Pro Gln Ala Phe Lys Leu Leu Ser Ala Val Asp Ile Leu Gly Glu Lys
                965                 970                 975
Phe Gly Ile Gly Leu Pro Ile Leu Phe Leu Arg Gly Ser Asn Ser Gln
            980                 985                 990
Arg Leu Ala Asp Gln Tyr Arg Arg His Ser Leu Phe Gly Thr Gly Lys
        995                 1000                1005
Asp Gln Thr Glu Ser Trp Trp Lys Ala Phe Ser Arg Gln Leu Ile
    1010                1015                1020
Thr Glu Gly Phe Leu Val Glu Val Ser Arg Tyr Asn Lys Phe Met
    1025                1030                1035
Lys Ile Cys Ala Leu Thr Lys Lys Gly Arg Asn Trp Leu His Lys
    1040                1045                1050
Ala Asn Thr Glu Ser Gln Ser Leu Ile Leu Gln Ala Asn Glu Glu
    1055                1060                1065
Leu Cys Pro Lys Lys Leu Leu Pro Ser Ser Lys Thr Val Ser
    1070                1075                1080
Ser Gly Thr Lys Glu His Cys Tyr Asn Gln Val Pro Val Glu Leu
    1085                1090                1095
Ser Thr Glu Lys Lys Ser Asn Leu Glu Lys Leu Tyr Ser Tyr Lys
    1100                1105                1110
Pro Cys Asp Lys Ile Ser Ser Gly Ser Asn Ile Ser Lys Lys Ser
    1115                1120                1125
Ile Met Val Gln Ser Pro Glu Lys Ala Tyr Ser Ser Gln Pro
    1130                1135                1140
Val Ile Ser Ala Gln Glu Gln Glu Thr Gln Ile Val Leu Tyr Gly
    1145                1150                1155
Lys Leu Val Glu Ala Arg Gln Lys His Ala Asn Lys Met Asp Val
    1160                1165                1170
Pro Pro Ala Ile Leu Ala Thr Asn Lys Ile Leu Val Asp Met Ala
    1175                1180                1185
Lys Met Arg Pro Thr Thr Val Glu Asn Val Lys Arg Ile Asp Gly
    1190                1195                1200
Val Ser Glu Gly Lys Ala Ala Met Leu Ala Pro Leu Leu Glu Val
    1205                1210                1215
Ile Lys His Phe Cys Gln Thr Asn Ser Val Gln Thr Asp Leu Phe
    1220                1225                1230
Ser Ser Thr Lys Pro Gln Glu Gln Lys Thr Ser Leu Val Ala
    1235                1240                1245
Lys Asn Lys Ile Cys Thr Leu Ser Gln Ser Met Ala Ile Thr Tyr
    1250                1255                1260
Ser Leu Phe Gln Glu Lys Lys Met Pro Leu Lys Ser Ile Ala Glu
    1265                1270                1275
```

-continued

| | | | | | | | | | | |
|---|---|---|---|---|---|---|---|---|---|---|
| Ser | Arg | Ile | Leu | Pro | Leu | Met | Thr | Ile | Gly | Met | His | Leu | Ser | Gln |
| | 1280 | | | | | 1285 | | | | 1290 | | | | |

Ala Val Lys Ala Gly Cys Pro Leu Asp Leu Glu Arg Ala Gly Leu
    1295                       1300                       1305

Thr Pro Glu Val Gln Lys Ile Ile Ala Asp Val Ile Arg Asn Pro
 1310                     1315                     1320

Pro Val Asn Ser Asp Met Ser Lys Ile Ser Leu Ile Arg Met Leu
 1325                     1330                     1335

Val Pro Glu Asn Ile Asp Thr Tyr Leu Ile His Met Ala Ile Glu
 1340                     1345                     1350

Ile Leu Lys His Gly Pro Asp Ser Gly Leu Gln Pro Ser Cys Asp
 1355                     1360                     1365

Val Asn Lys Arg Arg Cys Phe Pro Gly Ser Glu Glu Ile Cys Ser
 1370                     1375                     1380

Ser Ser Lys Arg Ser Lys Glu Glu Val Gly Ile Asn Thr Glu Thr
 1385                     1390                     1395

Ser Ser Ala Glu Arg Lys Arg Arg Leu Pro Val Trp Phe Ala Lys
 1400                     1405                     1410

Gly Ser Asp Thr Ser Lys Lys Leu Met Asp Lys Thr Lys Arg Gly
 1415                     1420                     1425

Gly Leu Phe Ser
 1430

<210> SEQ ID NO 11
<211> LENGTH: 4296
<212> TYPE: DNA
<213> ORGANISM: Homo sapiens

<400> SEQUENCE: 11

```
atgagtgaaa aaaaattgga acaactgca cagcagcgga atgtcctga atggatgaat       60 gtgcagaata aaagatgtgc tgtagaagaa agaaaggcat gtgttcggaa gagtgttttt      120
gaagatgacc tccccttctt agaattcact ggatccattg tgtatagtta cgatgctagt      180
gattgctctt tcctgtcaga agatattagc atgagtctat cagatgggga tgtggtggga      240
tttgacatgg agtggccacc attatacaat agagggaaac ttggcaaagt tgcactaatt      300
cagttgtgtg tttctgagag caaatgttac ttgttccacg tttcttccat gtcagttttt      360
ccccagggat taaaaatgtt gcttgaaaat aaagcagtta aaaaggcagg tgtaggaatt      420
gaaggagatc agtggaaact tctacgtgac tttgatatca aattgaagaa tttgtggag      480 ttgacagatg ttgccaataa aaagctgaaa tgcacagaga cctggagcct taacagtctg      540
gttaaacacc tcttaggtaa acagctcctg aaagacaagt ctatccgctg tagcaattgg      600
agtaaatttc ctctcactga ggaccagaaa ctgtatgcag ccactgatgc ttatgctggt      660
tttattattt accgaaattt agagattttg gatgatactg tgcaaaggtt gctataaat      720 aaagaggaag aaatcctact tagcgacatg aacaaacagt tgacttcaat ctctgaggaa      780
gtgatggatc tggctaagca tcttcctcat gctttcagta aattggaaaa cccacggagg      840
gtttctatct tactaaagga tatttcagaa aatctatatt cactgaggag gatgataatt      900
gggtctacta acattgagac tgaactgagg cccagcaata atttaaactt attatccttt      960
gaagattcaa ctactggggg agtacaacag aaacaaatta gagaacatga gtttttaatt     1020
cacgttgaag atgaaacatg ggacccaaca cttgatcatt tagctaaaca tgatggagaa     1080
gatgtacttg gaaataaagt ggaacgaaaa gaagatggat ttgaagatgg agtagaagac     1140
```

```
aacaaattga aagagaatat ggaaagagct tgtttgatgt cgttagatat tacagaacat   1200
gaactccaaa ttttggaaca gcagtctcag gaagaatatc ttagtgatat tgcttataaa   1260
tctactgagc atttatctcc caatgataat gaaaacgata cgtcctatgt aattgagagt   1320
gatgaagatt tagaaatgga gatgcttaag catttatctc ccaatgataa tgaaaacgat   1380
acgtcctatg taattgagag tgatgaagat ttagaaatgg agatgcttaa gtctttagaa   1440
aacctcaata gtggcacggt agaaccaact cattctaaat gcttaaaaat ggaaagaaat   1500
ctgggtcttc ctactaaaga agaagaagaa gatgatgaaa atgaagctaa tgaaggggaa   1560
gaagatgatg ataaggactt tttgtggcca gcacccaatg aagagcaagt tacttgcctc   1620
aagatgtact ttggccattc cagttttaaa ccagttcagt ggaaagtgat tcattcagta   1680
ttagaagaaa gaagagataa tgttgctgtc atggcaactg atatggaaaa gagtttgtgc   1740
ttccagtatc cacctgttta tgtaggcaag attggccttg ttatctctcc ccttatttct   1800
ctgatggaag accaagtgct acagcttaaa atgtccaaca tcccagcttg cttccttgga   1860
tcagcacagt cagaaaatgt tctaacagat attaaattag gtaaataccg gattgtatac   1920
gtaactccag aatactgttc aggtaacatg ggcctgctcc agcaacttga ggctgatatt   1980
ggtatcacgc tcattgctgt ggatgaggct cactgtattt ctgagtgggg gcatgatttt   2040
agggattcat tcaggaagtt gggctcccta agacagcac tgccaatggt tccaatcgtt   2100
gcacttactg ctactgcaag ttcttcaatc cgggaagaca ttgtacgttg cttaaatctg   2160
agaaatcctc agatcacctg tactggtttt gatcgaccaa acctgtattt agaagttagg   2220
cgaaaaacag ggaatatcct tcaggatctg cagccatttc ttgtcaaaac aagttcccac   2280
tgggaatttg aaggtccaac aatcatctac tgtccttcta gaaaaatgac acaacaagtt   2340
acaggtgaac ttaggaaact gaatctatcc tgtggaacat accatgcggg catgagtttt   2400
agcacaagga aagacattca tcataggttt gtgagagatg aaattcagtg tgtcatagct   2460
accatagctt ttggaatggg cattaataaa gctgacattc gccaagtcat tcattacggt   2520
gctcctaagg acatggaatc atattatcag gagattggta gagctggtcg tgatggactt   2580
caaagttctt gtcacgtcct ctgggctcct gcagacatta acttaaatag gcaccttctt   2640
actgagatac gtaatgagaa gtttcgatta tacaaattaa agatgatggc aaagatggaa   2700
aaatatcttc attctagcag atgtaggaga caaatcatct tgtctcattt tgaggacaaa   2760
caagtacaaa aagcctcctt gggaattatg ggaactgaaa aatgctgtga taattgcagg   2820
tccagattgg atcattgcta ttccatggat gactcagagg atacatcctg ggactttggt   2880
ccacaagcat ttaagctttt gtctgctgtg gacatcttag gcgaaaaatt tggaattggg   2940
cttccaattt tatttctccg aggatctaat tctcagcgtc ttgccgatca atatcgcagg   3000
cacagtttat ttggcactgg caaggatcaa acagagagtt ggtggaaggc tttttcccgt   3060
cagctgatca ctgagggatt cttggtagaa gtttctcggt ataacaaatt tatgaagatt   3120
tgcgccctta cgaaaaaggg tagaaattgg cttcataaag ctaatacaga atctcagagc   3180
ctcatccttc aagctaatga agaattgtgt ccaagaagt tgcttctgcc tagttcgaaa   3240
actgtatctt cgggcaccaa agagcattgt tataatcaag taccagttga attaagtaca   3300
gagaagaagt ctaacttgga gaagttatat tcttataaac catgtgataa gatttcttct   3360
gggagtaaca tttctaaaaa aagtatcatg gtacagtcac cagaaaaagc ttacagttcc   3420
tcacagcctg ttatttcggc acaagagcag gagactcaga ttgtgttata tggcaaattg   3480
gtagaagcta ggcagaaaca tgccaataaa atggatgttc ccccagctat tctggcaaca   3540
```

-continued

```
aacaagatac tggtggatat ggccaaaatg agaccaacta cggttgaaaa cgtaaaaagg   3600
attgatggtg tttctgaagg caaagctgcc atgttggccc ctctgttgga agtcatcaaa   3660
catttctgcc aaacaaatag tgttcagaca gacctctttt caagtacaaa acctcaagaa   3720
gaacagaaga cgagtctggt agcaaaaaat aaaatatgca cactttcaca gtctatggcc   3780
atcacatact ctttattcca agaaaagaag atgcctttga agagcatagc tgagagcagg   3840
attctgcctc tcatgacaat tggcatgcac ttataccaag cggtgaaagc tggctgcccc   3900
cttgatttgg agcgagcagg cctgactcca gaggttcaga agattattgc tgatgttatc   3960
cgaaaccctc ccgtcaactc agatatgagt aaaattagcc taatcagaat gttagttcct   4020
gaaaacattg acacgtacct tatccacatg gcaattgaga tccttaaaca tggtcctgac   4080
agcggacttc aaccttcatg tgatgtcaac aaaaggagat gttttcccgg ttctgaagag   4140
atctgttcaa gttctaagag aagcaaggaa gaagtaggca tcaatactga gacttcatct   4200
gcagagagaa agagacgatt acctgtgtgg tttgccaaag gaagtgatac cagcaagaaa   4260
ttaatggaca aaacgaaaag gggaggtctt tttagt                             4296
```

<210> SEQ ID NO 12
<211> LENGTH: 1432
<212> TYPE: PRT
<213> ORGANISM: Homo sapiens

<400> SEQUENCE: 12

```
Met Ser Glu Lys Lys Leu Glu Thr Thr Ala Gln Gln Arg Lys Cys Pro
1               5                   10                  15

Glu Trp Met Asn Val Gln Asn Lys Arg Cys Ala Val Glu Glu Arg Lys
            20                  25                  30

Ala Cys Val Arg Lys Ser Val Phe Glu Asp Asp Leu Pro Phe Leu Glu
        35                  40                  45

Phe Thr Gly Ser Ile Val Tyr Ser Tyr Asp Ala Ser Asp Cys Ser Phe
    50                  55                  60

Leu Ser Glu Asp Ile Ser Met Ser Leu Ser Asp Gly Asp Val Val Gly
65                  70                  75                  80

Phe Asp Met Glu Trp Pro Pro Leu Tyr Asn Arg Gly Lys Leu Gly Lys
                85                  90                  95

Val Ala Leu Ile Gln Leu Cys Val Ser Glu Ser Lys Cys Tyr Leu Phe
            100                 105                 110

His Val Ser Ser Met Ser Val Phe Pro Gln Gly Leu Lys Met Leu Leu
        115                 120                 125

Glu Asn Lys Ala Val Lys Lys Ala Gly Val Gly Ile Glu Gly Asp Gln
    130                 135                 140

Trp Lys Leu Leu Arg Asp Phe Asp Ile Lys Leu Lys Asn Phe Val Glu
145                 150                 155                 160

Leu Thr Asp Val Ala Asn Lys Lys Leu Lys Cys Thr Glu Thr Trp Ser
                165                 170                 175

Leu Asn Ser Leu Val Lys His Leu Leu Gly Lys Gln Leu Leu Lys Asp
            180                 185                 190

Lys Ser Ile Arg Cys Ser Asn Trp Ser Lys Phe Pro Leu Thr Glu Asp
        195                 200                 205

Gln Lys Leu Tyr Ala Ala Thr Asp Ala Tyr Ala Gly Phe Ile Ile Tyr
    210                 215                 220

Arg Asn Leu Glu Ile Leu Asp Asp Thr Val Gln Arg Phe Ala Ile Asn
225                 230                 235                 240
```

-continued

```
Lys Glu Glu Glu Ile Leu Leu Ser Asp Met Asn Lys Gln Leu Thr Ser
                245                 250                 255

Ile Ser Glu Glu Val Met Asp Leu Ala Lys His Leu Pro His Ala Phe
                260                 265                 270

Ser Lys Leu Glu Asn Pro Arg Arg Val Ser Ile Leu Leu Lys Asp Ile
                275                 280                 285

Ser Glu Asn Leu Tyr Ser Leu Arg Arg Met Ile Ile Gly Ser Thr Asn
                290                 295                 300

Ile Glu Thr Glu Leu Arg Pro Ser Asn Asn Leu Asn Leu Leu Ser Phe
305                 310                 315                 320

Glu Asp Ser Thr Thr Gly Gly Val Gln Gln Lys Gln Ile Arg Glu His
                325                 330                 335

Glu Val Leu Ile His Val Glu Asp Glu Thr Trp Asp Pro Thr Leu Asp
                340                 345                 350

His Leu Ala Lys His Asp Gly Glu Asp Val Leu Gly Asn Lys Val Glu
                355                 360                 365

Arg Lys Glu Asp Gly Phe Glu Asp Gly Val Glu Asp Asn Lys Leu Lys
                370                 375                 380

Glu Asn Met Glu Arg Ala Cys Leu Met Ser Leu Asp Ile Thr Glu His
385                 390                 395                 400

Glu Leu Gln Ile Leu Glu Gln Gln Ser Gln Glu Glu Tyr Leu Ser Asp
                405                 410                 415

Ile Ala Tyr Lys Ser Thr Glu His Leu Ser Pro Asn Asp Asn Glu Asn
                420                 425                 430

Asp Thr Ser Tyr Val Ile Glu Ser Glu Asp Leu Glu Met Glu Met
                435                 440                 445

Leu Lys His Leu Ser Pro Asn Asp Asn Glu Asn Asp Thr Ser Tyr Val
                450                 455                 460

Ile Glu Ser Asp Glu Asp Leu Glu Met Glu Met Leu Lys Ser Leu Glu
465                 470                 475                 480

Asn Leu Asn Ser Gly Thr Val Glu Pro Thr His Ser Lys Cys Leu Lys
                485                 490                 495

Met Glu Arg Asn Leu Gly Leu Pro Thr Lys Glu Glu Glu Asp Asp
                500                 505                 510

Glu Asn Glu Ala Asn Glu Gly Glu Asp Asp Asp Lys Asp Phe Leu
                515                 520                 525

Trp Pro Ala Pro Asn Glu Glu Gln Val Thr Cys Leu Lys Met Tyr Phe
                530                 535                 540

Gly His Ser Ser Phe Lys Pro Val Gln Trp Lys Val Ile His Ser Val
545                 550                 555                 560

Leu Glu Glu Arg Arg Asp Asn Val Ala Val Met Ala Thr Gly Tyr Gly
                565                 570                 575

Lys Ser Leu Cys Phe Gln Tyr Pro Pro Val Tyr Val Gly Lys Ile Gly
                580                 585                 590

Leu Val Ile Ser Pro Leu Ile Ser Leu Met Glu Asp Gln Val Leu Gln
                595                 600                 605

Leu Lys Met Ser Asn Ile Pro Ala Cys Phe Leu Gly Ser Ala Gln Ser
                610                 615                 620

Glu Asn Val Leu Thr Asp Ile Lys Leu Gly Lys Tyr Arg Ile Val Tyr
625                 630                 635                 640

Val Thr Pro Glu Tyr Cys Ser Gly Asn Met Gly Leu Leu Gln Gln Leu
                645                 650                 655
```

-continued

Glu Ala Asp Ile Gly Ile Thr Leu Ile Ala Val Asp Glu Ala His Cys
            660                 665                 670

Ile Ser Glu Trp Gly His Asp Phe Arg Asp Ser Phe Arg Lys Leu Gly
        675                 680                 685

Ser Leu Lys Thr Ala Leu Pro Met Val Pro Ile Val Ala Leu Thr Ala
    690                 695                 700

Thr Ala Ser Ser Ser Ile Arg Glu Asp Ile Val Arg Cys Leu Asn Leu
705                 710                 715                 720

Arg Asn Pro Gln Ile Thr Cys Thr Gly Phe Asp Arg Pro Asn Leu Tyr
                725                 730                 735

Leu Glu Val Arg Arg Lys Thr Gly Asn Ile Leu Gln Asp Leu Gln Pro
            740                 745                 750

Phe Leu Val Lys Thr Ser Ser His Trp Glu Phe Glu Gly Pro Thr Ile
        755                 760                 765

Ile Tyr Cys Pro Ser Arg Lys Met Thr Gln Gln Val Thr Gly Glu Leu
    770                 775                 780

Arg Lys Leu Asn Leu Ser Cys Gly Thr Tyr His Ala Gly Met Ser Phe
785                 790                 795                 800

Ser Thr Arg Lys Asp Ile His His Arg Phe Val Arg Asp Glu Ile Gln
                805                 810                 815

Cys Val Ile Ala Thr Ile Ala Phe Gly Met Gly Ile Asn Lys Ala Asp
            820                 825                 830

Ile Arg Gln Val Ile His Tyr Gly Ala Pro Lys Asp Met Glu Ser Tyr
        835                 840                 845

Tyr Gln Glu Ile Gly Arg Ala Gly Arg Asp Gly Leu Gln Ser Ser Cys
    850                 855                 860

His Val Leu Trp Ala Pro Ala Asp Ile Asn Leu Asn Arg His Leu Leu
865                 870                 875                 880

Thr Glu Ile Arg Asn Glu Lys Phe Arg Leu Tyr Lys Leu Lys Met Met
                885                 890                 895

Ala Lys Met Glu Lys Tyr Leu His Ser Ser Arg Cys Arg Arg Gln Ile
            900                 905                 910

Ile Leu Ser His Phe Glu Asp Lys Gln Val Gln Lys Ala Ser Leu Gly
        915                 920                 925

Ile Met Gly Thr Glu Lys Cys Cys Asp Asn Cys Arg Ser Arg Leu Asp
    930                 935                 940

His Cys Tyr Ser Met Asp Asp Ser Glu Asp Thr Ser Trp Asp Phe Gly
945                 950                 955                 960

Pro Gln Ala Phe Lys Leu Leu Ser Ala Val Asp Ile Leu Gly Glu Lys
                965                 970                 975

Phe Gly Ile Gly Leu Pro Ile Leu Phe Leu Arg Gly Ser Asn Ser Gln
            980                 985                 990

Arg Leu Ala Asp Gln Tyr Arg Arg His Ser Leu Phe Gly Thr Gly Lys
        995                 1000                1005

Asp Gln Thr Glu Ser Trp Trp Lys Ala Phe Ser Arg Gln Leu Ile
    1010                1015                1020

Thr Glu Gly Phe Leu Val Glu Val Ser Arg Tyr Asn Lys Phe Met
    1025                1030                1035

Lys Ile Cys Ala Leu Thr Lys Lys Gly Arg Asn Trp Leu His Lys
    1040                1045                1050

Ala Asn Thr Glu Ser Gln Ser Leu Ile Leu Gln Ala Asn Glu Glu
    1055                1060                1065

Leu Cys Pro Lys Lys Leu Leu Leu Pro Ser Ser Lys Thr Val Ser

```
                1070                1075                1080
Ser Gly Thr Lys Glu His Cys Tyr Asn Gln Val Pro Val Glu Leu
    1085                1090                1095

Ser Thr Glu Lys Lys Ser Asn Leu Glu Lys Leu Tyr Ser Tyr Lys
    1100                1105                1110

Pro Cys Asp Lys Ile Ser Ser Gly Ser Asn Ile Ser Lys Lys Ser
    1115                1120                1125

Ile Met Val Gln Ser Pro Glu Lys Ala Tyr Ser Ser Ser Gln Pro
    1130                1135                1140

Val Ile Ser Ala Gln Glu Gln Thr Gln Ile Val Leu Tyr Gly
    1145                1150                1155

Lys Leu Val Glu Ala Arg Gln Lys His Ala Asn Lys Met Asp Val
    1160                1165                1170

Pro Pro Ala Ile Leu Ala Thr Asn Lys Ile Leu Val Asp Met Ala
    1175                1180                1185

Lys Met Arg Pro Thr Thr Val Glu Asn Val Lys Arg Ile Asp Gly
    1190                1195                1200

Val Ser Glu Gly Lys Ala Ala Met Leu Ala Pro Leu Leu Glu Val
    1205                1210                1215

Ile Lys His Phe Cys Gln Thr Asn Ser Val Gln Thr Asp Leu Phe
    1220                1225                1230

Ser Ser Thr Lys Pro Gln Glu Glu Gln Lys Thr Ser Leu Val Ala
    1235                1240                1245

Lys Asn Lys Ile Cys Thr Leu Ser Gln Ser Met Ala Ile Thr Tyr
    1250                1255                1260

Ser Leu Phe Gln Glu Lys Lys Met Pro Leu Lys Ser Ile Ala Glu
    1265                1270                1275

Ser Arg Ile Leu Pro Leu Met Thr Ile Gly Met His Leu Tyr Gln
    1280                1285                1290

Ala Val Lys Ala Gly Cys Pro Leu Asp Leu Glu Arg Ala Gly Leu
    1295                1300                1305

Thr Pro Glu Val Gln Lys Ile Ile Ala Asp Val Ile Arg Asn Pro
    1310                1315                1320

Pro Val Asn Ser Asp Met Ser Lys Ile Ser Leu Ile Arg Met Leu
    1325                1330                1335

Val Pro Glu Asn Ile Asp Thr Tyr Leu Ile His Met Ala Ile Glu
    1340                1345                1350

Ile Leu Lys His Gly Pro Ser Gly Leu Gln Pro Ser Cys Asp
    1355                1360                1365

Val Asn Lys Arg Arg Cys Phe Pro Gly Ser Glu Ile Cys Ser
    1370                1375                1380

Ser Ser Lys Arg Ser Lys Glu Glu Val Gly Ile Asn Thr Glu Thr
    1385                1390                1395

Ser Ser Ala Glu Arg Lys Arg Arg Leu Pro Val Trp Phe Ala Lys
    1400                1405                1410

Gly Ser Asp Thr Ser Lys Lys Leu Met Asp Lys Thr Lys Arg Gly
    1415                1420                1425

Gly Leu Phe Ser
    1430

<210> SEQ ID NO 13
<211> LENGTH: 4296
<212> TYPE: DNA
<213> ORGANISM: Homo sapiens
```

<400> SEQUENCE: 13

```
atgagtgaaa aaaaattgga aacaactgca cagcagcgga aatgtcctga atggatgaat    60
gtgcagaata aaagatgtgc tgtagaagaa agaaaggcat gtgttcggaa gagtgttttt   120
gaagatgacc tccccttctt agaattcact ggatccattg tgtatagtta cgatgctagt   180
gattgctctt tcctgtcaga agatattagc atgagtctat cagatgggga tgtggtggga   240
tttgacatgg agtggccacc attatacaat agagggaaac ttggcaaagt tgcactaatt   300
cagttgtgtg tttctgagag caaatgttac ttgttccacg tttcttccat gtcagttttt   360
ccccagggat taaaaatgtt gcttgaaaat aaagcagtta aaaaggcagg tgtaggaatt   420
gaaggagatc agtggaaact tctacgtgac tttgatatca aattgaagaa ttttgtggag   480
ttgacagatg ttgccaataa aaagctgaaa tgcacagaga cctggagcct taacagtctg   540
gttaaacacc tcttaggtaa acagctcctg aaagacaagt ctatccgctg tagcaattgg   600
agtaaatttc ctctcactga ggaccagaaa ctgtatgcag ccactgatgc ttatgctggt   660
tttattattt accgaaattt agagattttg gatgatactg tgcaaaggtt tgctataaat   720
aaagaggaag aaatcctact tagcgacatg aacaaacagt tgacttcaat ctctgaggaa   780
gtgatggatc tggctaagca tcttcctcat gctttcagta aattggaaaa cccacggagg   840
gtttctatct tactaaagga tatttcagaa aatctatatt cactgaggag gatgataatt   900
gggtctacta acattgagac tgaactgagg cccagcaata atttaaactt attatccttt   960
gaagattcaa ctactggggg agtacaacag aaacaaatta gagaacatga agtttttaatt  1020
cacgttgaag atgaaacatg ggacccaaca cttgatcatt tagctaaaca tgatggagaa  1080
gatgtacttg gaaataaagt ggaacgaaaa gaagatggat ttgaagatgg agtagaagac  1140
aacaaattga agagaatat ggaaagagct tgtttgatgt cgttagatat tacagaacat  1200
gaactccaaa ttttggaaca gcagtctcag gaagaatatc ttagtgatat tgcttataaa  1260
tctactgagc atttatctcc caatgataat gaaaacgata cgtcctatgt aattgagagt  1320
gatgaagatt tagaaatgga gatgcttaag catttatctc ccaatgataa tgaaaacgat  1380
acgtcctatg taattgagag tgatgaagat ttagaaatgg agatgcttaa gtctttagaa  1440
aacctcaata gtggcacggt agaaccaact cattctaaat gcttaaaaat ggaaagaaat  1500
ctgggtcttc ctactaaaga agaagaagaa gatgatgaaa atgaagctaa tgaaggggaa  1560
gaagatgatg ataaggactt tttgtggcca gcacccaatg aagagcaagt tacttgcctc  1620
aagatgtact ttggccattc cagttttaaa ccagttcagt ggaaagtgat tcattcagta  1680
ttagaagaaa gaagagataa tgttgctgtc atggcaactg atatggaaaa gagtttgtgc  1740
ttccagtatc cacctgttta tgtaggcaag attggccttg ttatctctcc ccttatttct  1800
ctgatggaag accaagtgct acagcttaaa atgtccaaca tcccagcttg cttccttgga  1860
tcagcacagt cagaaaatgt tctaacagat attaaattag gtaaataccg gattgtatac  1920
gtaactccag aatactgttc aggtaacatg ggcctgctcc agcaacttga ggctgatatt  1980
ggtatcacgc tcattgctgt ggatgaggct cactgtattt ctgagtgggg gcatgatttt  2040
agggattcat tcaggaagtt gggctcccta agacagcac tgccaatggt tccaatcgtt  2100
gcacttactg ctattgcaag ttcttcaatc cgggaagaca ttgtacgttg cttaaatctg  2160
agaaatcctc agatcacctg tactggtttt gatcgaccaa acctgtattt agaagttagg  2220
cgaaaaacag ggaatatcct tcaggatctg cagccatttc ttgtcaaaac aagttcccac  2280
```

| | | |
|---|---|---|
| tgggaatttg aaggtccaac aatcatctac tgtccttcta gaaaaatgac acaacaagtt | 2340 | |
| acaggtgaac ttaggaaact gaatctatcc tgtggaacat accatgcggg catgagtttt | 2400 | |
| agcacaagga aagacattca tcataggttt gtaagagatg aaattcagtg tgtcatagct | 2460 | |
| accatagctt ttggaatggg cattaataaa gctgacattc gccaagtcat tcattacggt | 2520 | |
| gctcctaagg acatggaatc atattatcag gagattggta gagctggtcg tgatggactt | 2580 | |
| caaagttctt gtcacgtcct ctgggctcct gcagacatta acttaaatag gcaccttctt | 2640 | |
| actgagatac gtaatgagaa gtttcgatta tacaaattaa agatgatggc aaagatggaa | 2700 | |
| aaatatcttc attctagcag atgtaggaga caaatcatct tgtctcattt tgaggacaaa | 2760 | |
| caagtacaaa aagcctcctt gggaattatg ggaactgaaa aatgctgtga taattgcagg | 2820 | |
| tccagattgg atcattgcta ttccatggat gactcagagg atacatcctg ggactttggt | 2880 | |
| ccacaagcat ttaagctttt gtctgctgtg gacatcttag gcgaaaaatt tggaattggg | 2940 | |
| cttccaattt tatttctccg aggatctaat tctcagcgtc ttgccgatca atatcgcagg | 3000 | |
| cacagtttat ttggcactgg caaggatcaa acagagagtt ggtggaaggc ttttcccgt | 3060 | |
| cagctgatca ctgagggatt cttggtagaa gtttctcggt ataacaaatt tatgaagatt | 3120 | |
| tgcgccctta cgaaaaaggg tagaaattgg cttcataaag ctaatacaga atctcagagc | 3180 | |
| ctcatccttc aagctaatga agaattgtgt ccaaagaagt tgcttctgcc tagttcgaaa | 3240 | |
| actgtatctt cgggcaccaa agagcattgt tataatcaag taccagttga attaagtaca | 3300 | |
| gagaagaagt ctaacttgga gaagttatat tcttataaac catgtgataa gatttcttct | 3360 | |
| gggagtaaca tttctaaaaa aagtatcatg gtacagtcac cagaaaaagc ttacagttcc | 3420 | |
| tcacagcctg ttatttcggc acaagagcag gagactcaga ttgtgttata tggcaaattg | 3480 | |
| gtagaagcta ggcagaaaca tgccaataaa atggatgttc ccccagctat tctggcaaca | 3540 | |
| aacaagatac tggtggatat ggccaaaatg agaccaacta cggttgaaaa cgtaaaaagg | 3600 | |
| attgatggtg tttctgaagg caaagctgcc atgttggccc ctctgttgga agtcatcaaa | 3660 | |
| catttctgcc aaacaaatag tgttcagaca gacctctttt caagtacaaa acctcaagaa | 3720 | |
| gaacagaaga cgagtctggt agcaaaaaat aaaatatgca cactttcaca gtctatggcc | 3780 | |
| atcacatact ctttattcca agaaaagaag atgcctttga agagcatagc tgagagcagg | 3840 | |
| attctgcctc tcatgacaat tggcatgcac ttataccaag cggtgaaagc tggctgcccc | 3900 | |
| cttgatttgg agcgagcagg cctgactcca gaggttcaga agattattgc tgatgttatc | 3960 | |
| cgaaaccctc ccgtcaactc agatatgagt aaaattagcc taatcagaat gttagttcct | 4020 | |
| gaaaacattg acacgtacct tatccacatg gcaattgaga tccttaaaca tggtcctgac | 4080 | |
| agcggacttc aaccttcatg tgatgtcaac aaaaaggagt gttttcccgg ttctgaagag | 4140 | |
| atctgttcaa gttctaagag aagcaaggaa gaagtaggca tcaatactga gacttcatct | 4200 | |
| gcagagagaa agagacgatt acctgtgtgg tttgccaaag aagtgataca cagcaagaaa | 4260 | |
| ttaatggaca aaacgaaaag gggaggtctt tttagt | 4296 | |

<210> SEQ ID NO 14
<211> LENGTH: 1432
<212> TYPE: PRT
<213> ORGANISM: Homo sapiens

<400> SEQUENCE: 14

Met Ser Glu Lys Lys Leu Glu Thr Thr Ala Gln Gln Arg Lys Cys Pro
1               5                   10                  15

Glu Trp Met Asn Val Gln Asn Lys Arg Cys Ala Val Glu Arg Lys
            20                  25                  30

Ala Cys Val Arg Lys Ser Val Phe Glu Asp Asp Leu Pro Phe Leu Glu
        35                  40                  45

Phe Thr Gly Ser Ile Val Tyr Ser Tyr Asp Ala Ser Asp Cys Ser Phe
    50                  55                  60

Leu Ser Glu Asp Ile Ser Met Ser Leu Ser Asp Gly Asp Val Val Gly
65                  70                  75                  80

Phe Asp Met Glu Trp Pro Pro Leu Tyr Asn Arg Gly Lys Leu Gly Lys
                85                  90                  95

Val Ala Leu Ile Gln Leu Cys Val Ser Glu Ser Lys Cys Tyr Leu Phe
            100                 105                 110

His Val Ser Ser Met Ser Val Phe Pro Gln Gly Leu Lys Met Leu Leu
        115                 120                 125

Glu Asn Lys Ala Val Lys Lys Ala Gly Val Gly Ile Glu Gly Asp Gln
    130                 135                 140

Trp Lys Leu Leu Arg Asp Phe Asp Ile Lys Leu Lys Asn Phe Val Glu
145                 150                 155                 160

Leu Thr Asp Val Ala Asn Lys Lys Leu Lys Cys Thr Glu Thr Trp Ser
                165                 170                 175

Leu Asn Ser Leu Val Lys His Leu Leu Gly Lys Gln Leu Leu Lys Asp
            180                 185                 190

Lys Ser Ile Arg Cys Ser Asn Trp Ser Lys Phe Pro Leu Thr Glu Asp
        195                 200                 205

Gln Lys Leu Tyr Ala Ala Thr Asp Ala Tyr Ala Gly Phe Ile Ile Tyr
    210                 215                 220

Arg Asn Leu Glu Ile Leu Asp Asp Thr Val Gln Arg Phe Ala Ile Asn
225                 230                 235                 240

Lys Glu Glu Glu Ile Leu Leu Ser Asp Met Asn Lys Gln Leu Thr Ser
                245                 250                 255

Ile Ser Glu Glu Val Met Asp Leu Ala Lys His Leu Pro His Ala Phe
            260                 265                 270

Ser Lys Leu Glu Asn Pro Arg Arg Val Ser Ile Leu Leu Lys Asp Ile
        275                 280                 285

Ser Glu Asn Leu Tyr Ser Leu Arg Arg Met Ile Ile Gly Ser Thr Asn
    290                 295                 300

Ile Glu Thr Glu Leu Arg Pro Ser Asn Asn Leu Asn Leu Leu Ser Phe
305                 310                 315                 320

Glu Asp Ser Thr Thr Gly Gly Val Gln Gln Lys Gln Ile Arg Glu His
                325                 330                 335

Glu Val Leu Ile His Val Glu Asp Glu Thr Trp Asp Pro Thr Leu Asp
            340                 345                 350

His Leu Ala Lys His Asp Gly Glu Asp Val Leu Gly Asn Lys Val Glu
        355                 360                 365

Arg Lys Glu Asp Gly Phe Glu Asp Gly Val Glu Asp Asn Lys Leu Lys
    370                 375                 380

Glu Asn Met Glu Arg Ala Cys Leu Met Ser Leu Asp Ile Thr Glu His
385                 390                 395                 400

Glu Leu Gln Ile Leu Glu Gln Gln Ser Gln Glu Tyr Leu Ser Asp
                405                 410                 415

Ile Ala Tyr Lys Ser Thr Glu His Leu Ser Pro Asn Asp Asn Glu Asn
            420                 425                 430

Asp Thr Ser Tyr Val Ile Glu Ser Asp Glu Asp Leu Glu Met Glu Met

-continued

```
            435                 440                 445
Leu Lys His Leu Ser Pro Asn Asp Asn Glu Asn Asp Thr Ser Tyr Val
450                 455                 460
Ile Glu Ser Asp Glu Asp Leu Glu Met Glu Met Leu Lys Ser Leu Glu
465                 470                 475                 480
Asn Leu Asn Ser Gly Thr Val Glu Pro Thr His Ser Lys Cys Leu Lys
                485                 490                 495
Met Glu Arg Asn Leu Gly Leu Pro Thr Lys Glu Glu Glu Asp Asp
                500                 505                 510
Glu Asn Glu Ala Asn Glu Gly Glu Asp Asp Lys Asp Phe Leu
                515                 520                 525
Trp Pro Ala Pro Asn Glu Glu Gln Val Thr Cys Leu Lys Met Tyr Phe
530                 535                 540
Gly His Ser Ser Phe Lys Pro Val Gln Trp Lys Val Ile His Ser Val
545                 550                 555                 560
Leu Glu Glu Arg Arg Asp Asn Val Ala Val Met Ala Thr Gly Tyr Gly
                565                 570                 575
Lys Ser Leu Cys Phe Gln Tyr Pro Pro Val Tyr Val Gly Lys Ile Gly
                580                 585                 590
Leu Val Ile Ser Pro Leu Ile Ser Leu Met Glu Asp Gln Val Leu Gln
                595                 600                 605
Leu Lys Met Ser Asn Ile Pro Ala Cys Phe Leu Gly Ser Ala Gln Ser
                610                 615                 620
Glu Asn Val Leu Thr Asp Ile Lys Leu Gly Lys Tyr Arg Ile Val Tyr
625                 630                 635                 640
Val Thr Pro Glu Tyr Cys Ser Gly Asn Met Gly Leu Leu Gln Gln Leu
                645                 650                 655
Glu Ala Asp Ile Gly Ile Thr Leu Ile Ala Val Asp Glu Ala His Cys
                660                 665                 670
Ile Ser Glu Trp Gly His Asp Phe Arg Asp Ser Phe Arg Lys Leu Gly
                675                 680                 685
Ser Leu Lys Thr Ala Leu Pro Met Val Pro Ile Val Ala Leu Thr Ala
                690                 695                 700
Ile Ala Ser Ser Ser Ile Arg Glu Asp Ile Val Arg Cys Leu Asn Leu
705                 710                 715                 720
Arg Asn Pro Gln Ile Thr Cys Thr Gly Phe Asp Arg Pro Asn Leu Tyr
                725                 730                 735
Leu Glu Val Arg Arg Lys Thr Gly Asn Ile Leu Gln Asp Leu Gln Pro
                740                 745                 750
Phe Leu Val Lys Thr Ser Ser His Trp Glu Phe Glu Gly Pro Thr Ile
                755                 760                 765
Ile Tyr Cys Pro Ser Arg Lys Met Thr Gln Gln Val Thr Gly Glu Leu
                770                 775                 780
Arg Lys Leu Asn Leu Ser Cys Gly Thr Tyr His Ala Gly Met Ser Phe
785                 790                 795                 800
Ser Thr Arg Lys Asp Ile His His Arg Phe Val Arg Asp Glu Ile Gln
                805                 810                 815
Cys Val Ile Ala Thr Ile Ala Phe Gly Met Gly Ile Asn Lys Ala Asp
                820                 825                 830
Ile Arg Gln Val Ile His Tyr Gly Ala Pro Lys Asp Met Glu Ser Tyr
                835                 840                 845
Tyr Gln Glu Ile Gly Arg Ala Gly Arg Asp Gly Leu Gln Ser Ser Cys
850                 855                 860
```

-continued

```
His Val Leu Trp Ala Pro Ala Asp Ile Asn Leu Asn Arg His Leu Leu
865                 870                 875                 880

Thr Glu Ile Arg Asn Glu Lys Phe Arg Leu Tyr Lys Leu Lys Met Met
                885                 890                 895

Ala Lys Met Glu Lys Tyr Leu His Ser Ser Arg Cys Arg Arg Gln Ile
            900                 905                 910

Ile Leu Ser His Phe Glu Asp Lys Gln Val Gln Lys Ala Ser Leu Gly
        915                 920                 925

Ile Met Gly Thr Glu Lys Cys Cys Asp Asn Cys Arg Ser Arg Leu Asp
    930                 935                 940

His Cys Tyr Ser Met Asp Asp Ser Glu Asp Thr Ser Trp Asp Phe Gly
945                 950                 955                 960

Pro Gln Ala Phe Lys Leu Leu Ser Ala Val Asp Ile Leu Gly Glu Lys
                965                 970                 975

Phe Gly Ile Gly Leu Pro Ile Leu Phe Leu Arg Gly Ser Asn Ser Gln
            980                 985                 990

Arg Leu Ala Asp Gln Tyr Arg Arg His Ser Leu Phe Gly Thr Gly Lys
        995                 1000                1005

Asp Gln Thr Glu Ser Trp Trp Lys Ala Phe Ser Arg Gln Leu Ile
    1010                1015                1020

Thr Glu Gly Phe Leu Val Glu Val Ser Arg Tyr Asn Lys Phe Met
    1025                1030                1035

Lys Ile Cys Ala Leu Thr Lys Lys Gly Arg Asn Trp Leu His Lys
    1040                1045                1050

Ala Asn Thr Glu Ser Gln Ser Leu Ile Leu Gln Ala Asn Glu Glu
    1055                1060                1065

Leu Cys Pro Lys Lys Leu Leu Pro Ser Ser Lys Thr Val Ser
    1070                1075                1080

Ser Gly Thr Lys Glu His Cys Tyr Asn Gln Val Pro Val Glu Leu
    1085                1090                1095

Ser Thr Glu Lys Lys Ser Asn Leu Glu Lys Leu Tyr Ser Tyr Lys
    1100                1105                1110

Pro Cys Asp Lys Ile Ser Ser Gly Ser Asn Ile Ser Lys Lys Ser
    1115                1120                1125

Ile Met Val Gln Ser Pro Glu Lys Ala Tyr Ser Ser Ser Gln Pro
    1130                1135                1140

Val Ile Ser Ala Gln Glu Gln Glu Thr Gln Ile Val Leu Tyr Gly
    1145                1150                1155

Lys Leu Val Glu Ala Arg Gln Lys His Ala Asn Lys Met Asp Val
    1160                1165                1170

Pro Pro Ala Ile Leu Ala Thr Asn Lys Ile Leu Val Asp Met Ala
    1175                1180                1185

Lys Met Arg Pro Thr Thr Val Glu Asn Val Lys Arg Ile Asp Gly
    1190                1195                1200

Val Ser Glu Gly Lys Ala Ala Met Leu Ala Pro Leu Leu Glu Val
    1205                1210                1215

Ile Lys His Phe Cys Gln Thr Asn Ser Val Gln Thr Asp Leu Phe
    1220                1225                1230

Ser Ser Thr Lys Pro Gln Glu Glu Gln Lys Thr Ser Leu Val Ala
    1235                1240                1245

Lys Asn Lys Ile Cys Thr Leu Ser Gln Ser Met Ala Ile Thr Tyr
    1250                1255                1260
```

| | | | | | | | | | | |
|---|---|---|---|---|---|---|---|---|---|---|
| Ser | Leu | Phe | Gln | Glu | Lys | Lys | Met | Pro | Leu | Lys | Ser | Ile | Ala | Glu |
| | 1265 | | | | | 1270 | | | | | 1275 | | | |

Ser Arg Ile Leu Pro Leu Met Thr Ile Gly Met His Leu Tyr Gln
    1280                            1285                          1290

Ala Val Lys Ala Gly Cys Pro Leu Asp Leu Glu Arg Ala Gly Leu
    1295                            1300                            1305

Thr Pro Glu Val Gln Lys Ile Ile Ala Asp Val Ile Arg Asn Pro
    1310                            1315                          1320

Pro Val Asn Ser Asp Met Ser Lys Ile Ser Leu Ile Arg Met Leu
    1325                            1330                          1335

Val Pro Glu Asn Ile Asp Thr Tyr Leu Ile His Met Ala Ile Glu
    1340                            1345                          1350

Ile Leu Lys His Gly Pro Asp Ser Gly Leu Gln Pro Ser Cys Asp
    1355                            1360                          1365

Val Asn Lys Arg Arg Cys Phe Pro Gly Ser Glu Glu Ile Cys Ser
    1370                            1375                          1380

Ser Ser Lys Arg Ser Lys Glu Glu Val Gly Ile Asn Thr Glu Thr
    1385                            1390                          1395

Ser Ser Ala Glu Arg Lys Arg Arg Leu Pro Val Trp Phe Ala Lys
    1400                            1405                          1410

Gly Ser Asp Thr Ser Lys Lys Leu Met Asp Lys Thr Lys Arg Gly
    1415                            1420                          1425

Gly Leu Phe Ser
    1430

<210> SEQ ID NO 15
<211> LENGTH: 3396
<212> TYPE: DNA
<213> ORGANISM: Homo sapiens

<400> SEQUENCE: 15

| | | |
|---|---|---|
| atgccgcgcg ctccccgctg ccgagccgtg cgctccctgc tgcgcagcca ctaccgcgag | 60 |
| gtgctgccgc tggccacgtt cgtgcggcgc ctggggcccc agggctggcg gctggtgcag | 120 |
| cgcggggacc cggcggcttt ccgcgcgctg gtggcccagt gcctggtgtg cgtgccctgg | 180 |
| gacgcacggc cgccccccgc cgccccctcc ttccgccagg tgtcctgcct gaaggagctg | 240 |
| gtggcccgag tgctgcagag gctgtgcgag cgcggcgcga agaacgtgct ggccttcggc | 300 |
| ttcgcgctgc tggacggggc ccgcgggggc ccccccgagg ccttcaccac cagcgtgcgc | 360 |
| agctacctgc ccaacacggt gaccgacgca ctgggggga gcggggcgtg ggggctgctg | 420 |
| ctgcgccgcg tgggcgacga cgtgctggtt cacctgctgg cacgctgcgc gctctttgtg | 480 |
| ctggtggctc ccagctgcgc ctaccaggtg tgcgggccgc cgctgtacca gctcggcgct | 540 |
| gccactcagg cccggccccc gccacacgct agtggacccc gaaggcgtct gcgatgcgaa | 600 |
| cgggcctgga accatagcgt cagggaggcc ggggtccccc tgggcctgcc agccccgggt | 660 |
| gcgaggaggc gcggggcag tgccagccga agtctgccgt tgcccaagag gcccaggcgt | 720 |
| ggcgctgccc ctgagccgga gcggacgccc gttgggcagg ggtcctgggc ccacccgggc | 780 |
| aggacgcgtg gaccgagtga ccgtggttc tgtgtggtgt cacctgccag acccgccgaa | 840 |
| gaagccacct ctttggaggg tgcgctctct ggcacgcgcc actccacccc atccgtgggc | 900 |
| cgccagcacc acgcgggccc cccatccaca tcgcggccac cacgtccctg ggacacgcct | 960 |
| tgtccccgg tgtacgccga gaccaagcac ttcctctact cctcaggcga caaggagcag | 1020 |
| ctgcggccct ccttcctact cagctctctg aggcccagcc tgactggcgc tcggaggctc | 1080 |

```
gtggagacca tctttctggg ttccaggccc tggatgccag ggactcccg caggttgccc    1140 cgcctgcccc agcgctactg gcaaatgcgg cccctgtttc tggagctgct tgggaaccac    1200
gcgcagtgcc cctacggggt gctcctcaag acgcactgcc cgctgcgagc tgcggtcacc    1260
ccagcagccg tgtctgtgc ccgggagaag ccccagggct ctgtggcggc ccccgaggag    1320
gaggacacag accccgtcg cctggtgcag ctgctccgcc agcacagcag cccctggcag    1380
gtgtacggct tcgtgcgggc ctgcctgcgc ggctggtgc ccccaggcct ctggggctcc    1440
aggcacaacg aacgccgctt cctcaggaac accaagaagt tcatctccct ggggaagcat    1500
gccaagctct cgctgcagga gctgacgtgg aagatgagcg tgcgggactg cgcttggctg    1560
cgcaggagcc caggggttgg ctgtgttccg gccgcagagc accgtctgcg tgaggagatc    1620
ctggccaagt tcctgcactg gctgatgagt gtgtacgtcg tcgagctgct caggtctttc    1680 tttatgtca cggagaccac gtttcaaaag acaggctct ttttctaccg gaagagtgtc    1740
tggagcaagt tgcaaagcat tggaatcaga cagcacttga agagggtgca gctgcgggag    1800
ctgtcggaag cagaggtcag gcagcatcgg gaagccaggc ccgccctgct gacgtccaga    1860
ctccgcttca tccccaagcc tgacgggctg cggccgattg tgaacatgga ctacgtcgtg    1920
ggagccagaa cgttccgcag agaaaagagg gccgagcgtc tcacctcgag ggtgaaggca    1980
ctgttcagcg tgctcaacta cgagcgggcg cggcgcccg gcctcctggg cgcctctgtg    2040
ctgggcctgg acgatatcca cagggcctgg cgcaccttcg tgctgcgtgt gcgggcccag    2100
gacccgccgc ctgagctgta ctttgtcaag gtggatgtga cgggcgcgta cgacaccatc    2160
ccccaggaca ggctcacgga ggtcatcgcc agcatcatca accccagaa cacgtactgc    2220 gtgcgtcggt atgccgtggt ccagaaggcc gcccatgggc acgtccgcaa ggccttcaag    2280
agccacgtct ctaccttgac agacctccag ccgtacatgc gacagttcgt ggctcacctg    2340
caggagacca gcccgctgag ggatgccgtc gtcatcgagc agagctcctc cctgaatgag    2400
gccagcagtg gcctcttcga cgtcttccta cgcttcatgt gccaccacgc cgtgcgcatc    2460
aggggcaagt cctacgtcca gtgccagggg atcccgcagg gctccatcct ctccacgctg    2520
ctctgcagcc tgtgctacgg cgacatggag aacaagctgt tgcggggat tcggcgggac    2580 gggctgctcc tgcgtttggt ggatgatttc ttgttggtga cacctcacct cacccacgcg    2640
aaaaccttcc tcaggaccct ggtccgaggt gtccctgagt atggctgcgt ggtgaacttg    2700
cggaagacag tggtgaactt ccctgtagaa gacgaggccc tgggtggcac ggcttttgtt    2760
cagatgccgg cccacggcct attccctggt gcggcctgc tgctggatac ccggaccctg    2820
gaggtgcaga gcgactactc cagctatgcc cggacctcca tcagagccag tctcaccttc    2880
aaccgcggct tcaaggctgg gaggaacatg cgtcgcaaac tctttggggt cttgcggctg    2940
aagtgtcaca gcctgttct ggatttgcag gtgaacagcc tccagacggt gtgcaccaac    3000
atctacaaga tcctcctgct gcaggcgtac aggtttcacg catgtgtgct gcagctccca    3060
tttcatcagc aagtttggaa gaaccccaca ttttcctgc gcgtcatctc tgacacggcc    3120
tccctctgct actccatcct gaaagccaag aacgcaggga tgtcgctggg gccaagggc    3180 gccgccggcc ctctgccctc cgaggccgtg cagtggctgt gccaccaagc attcctgctc    3240
aagctgactc gacaccgtgt cacctacgtg ccactcctgg ggtcactcag acagcccag    3300 acgcagctga gtcggaagct cccggggacg acgctgactg ccctggaggc cgcagccaac    3360
ccggcactgc cctcagactt caagaccatc ctggac                              3396
```

<210> SEQ ID NO 16
<211> LENGTH: 3396
<212> TYPE: DNA
<213> ORGANISM: Homo sapiens

<400> SEQUENCE: 16

| | | | | | | |
|---|---|---|---|---|---|---|
| atgccgcgcg | ctccccgctg | ccgagccgtg | cgctccctgc | tgcgcagcca | ctaccgcgag | 60 |
| gtgctgccgc | tggccacgtt | cgtgcggcgc | ctggggcccc | agggctggcg | gctggtgcag | 120 |
| cgcggggacc | cggcggcttt | ccgcgcgctg | gtggcccagt | gcctggtgtg | cgtgccctgg | 180 |
| gacgcacggc | cgcccccgc | cgcccctcc | ttccgccagg | tgtcctgcct | gaaggagctg | 240 |
| gtggcccgag | tgctgcagag | gctgtgcgag | cgcggcgcga | agaacgtgct | ggccttcggc | 300 |
| ttcgcgctgc | tggacgggc | ccgcgggggc | ccccccgagg | ccttcaccac | cagcgtgcgc | 360 |
| agctacctgc | ccaacacggt | gaccgacgca | ctgcggggga | gcgggcgtg | ggggctgctg | 420 |
| ctgcgccgcg | tgggcgacga | cgtgctggtt | cacctgctgg | cacgctgcgc | gctctttgtg | 480 |
| ctggtggctc | ccagctgcgc | ctaccaggtg | tgcgggccgc | cgctgtacca | gctcggcgct | 540 |
| gccactcagg | cccggccccc | gccacacgct | agtggacccc | gaaggcgtct | gggatgcgaa | 600 |
| cgggcctgga | accatagcgt | cagggaggcc | ggggtccccc | tgggcctgcc | agccccgggt | 660 |
| gcgaggaggc | gcggggcag | tgccagccga | agtctgccgt | tgcccaagag | gcccaggcgt | 720 |
| ggcgctgccc | ctgagccgga | gcggacgccc | gttgggcagg | ggtcctgggc | ccaccccggc | 780 |
| aggacgcgtg | gaccgagtga | ccgtggtttc | tgtgtggtgt | cacctgccag | acccgccgaa | 840 |
| gaagccacct | cttggaggg | tgcgctctct | ggcacgcgcc | actcccaccc | atccgtgggc | 900 |
| cgccagcacc | acgcgggccc | cccatccaca | tcgcggccac | cacgtccctg | ggacacgcct | 960 |
| tgtccccgg | tgtacgccga | gaccaagcac | ttcctctact | cctcaggcga | caaggagcag | 1020 |
| ctgcggccct | ccttcctact | cagctctctg | aggcccagcc | tgactggcgc | tcggaggctc | 1080 |
| gtggagacca | tctttctggg | ttccaggccc | tggatgccag | ggactcccg | caggttgccc | 1140 |
| cgcctgcccc | agcgctactg | gcaaatgcgg | ccctgtttc | tggagctgct | tgggaaccac | 1200 |
| gcgcagtgcc | cctacgggt | gctcctcaag | acgcactgcc | cgctgcgagc | tgcggtcacc | 1260 |
| ccagcagccg | gtgtctgtgc | ccgggagaag | ccccagggct | ctgtggcggc | ccccgaggag | 1320 |
| gaggacacag | accccgtcg | cctggtgcag | ctgctccgcc | agcacagcag | cccctggcag | 1380 |
| gtgtacggct | tcgtgcgggc | ctgcctgcgc | cggctggtgc | cccaggcct | tggggctcc | 1440 |
| aggcacaacg | aacgccgctt | cctcaggaac | accaagaagt | tcatctcct | ggggaagcat | 1500 |
| gccaagctct | cgctgcagga | gctgacgtgg | aagatgagcg | tgcgggactg | cgcttggctg | 1560 |
| cgcaggagcc | cagggttgg | ctgtgttccg | gccgcagagc | accgtctgcg | tgaggagatc | 1620 |
| ctggccaagt | tcctgcactg | gctgatgagt | gtgtacgtcg | tcgagctgct | caggtctttc | 1680 |
| ttttatgtca | cggagaccac | gtttcaaaag | aacaggctct | ttttctaccg | gaagagtgtc | 1740 |
| tggagcaagt | tgcaaagcat | tggaatcaga | cagcacttga | gagggtgca | gctgcgggag | 1800 |
| ctgtcggaag | cagaggtcag | gcagcatcgg | gaagccaggc | ccgccctgct | gacgtccaga | 1860 |
| ctccgcttca | tccccaagcc | tgacgggctg | cggccgattg | tgaacatgga | ctacgtcgtg | 1920 |
| ggagccagaa | cgttccgcag | agaaaagagg | gccgagcgtc | tcacctcgag | ggtgaaggca | 1980 |
| ctgttcagcg | tgctcaacta | cgagcgggcg | cggcgcccg | gcctcctggg | cgcctctgtg | 2040 |
| ctgggcctga | acgatatcca | cagggcctgg | cgcaccttcg | tgctgcgtgt | gcgggcccag | 2100 |
| gacccgccgc | ctgagctgta | ctttgtcaag | gtggatgtga | cgggcgcgta | cgacaccatc | 2160 |

```
cccaggaca ggctcacgga ggtcatcgcc agcatcatca aaccccagaa cacgtactgc    2220
gtgcgtcggt atgccgtggt ccagaaggcc gcccatgggc acgtccgcaa ggccttcaag    2280
agccacgtct ctaccttgac agacctccag ccgtacatgc gacagttcgt ggctcacctg    2340
caggagacca gcccgctgag ggatgccgtc gtcatcgagc agagctcctc cctgaatgag    2400
gccagcagtg gcctcttcga cgtcttccta cgcttcatgt gccaccacgc cgtgcgcatc    2460
aggggcaagt cctacgtcca gtgccagggg atcccgcagg gctccatcct ctccacgctg    2520
ctctgcagcc tgtgctacgg cgacatggag aacaagctgt tgcggggat cggcgggac    2580 gggctgctcc tgcgtttggt ggatgatttc ttgttggtga cacctcacct cacccacgcg    2640
aaaaccttcc tcaggaccct ggtccgaggt gtccctgagt atggctgcgt ggtgaacttg    2700
cggaagacag tggtgaactt ccctgtagaa gacgaggccc tgggtggcac ggcttttgtt    2760
cagatgccgg cccacggcct attcccctgg tgcggcctgc tgctggatac ccggaccctg    2820
gaggtgcaga gcgactactc cagctatgcc cggacctcca tcagagccag tctcaccttc    2880
aaccgcggct tcaaggctgg aggaacatg cgtcgcaaac tctttggggt cttgcggctg    2940
aagtgtcaca gcctgtttct ggatttgcag gtgaacagcc tccagacggt gtgcaccaac    3000
atctacaaga tcctcctgct gcaggcgtac aggtttcacg catgtgtgct gcagctccca    3060
tttcatcagc aagtttggaa gaaccccaca tttttcctgc gcgtcatctc tgacacggcc    3120
tccctctgct actccatcct gaaagccaag aacgcaggga tgtcgctggg ggccaagggc    3180
gccgccggcc ctctgccctc cgaggccgtg cagtggctgt gccaccaagc attcctgctc    3240
aagctgactc gacaccgtgt cacctacgtg ccactcctgg ggtcactcag gacagcccag    3300
acgcagctga gtcggaagct cccggggacg acgctgactg ccctggaggc cgcagccaac    3360
ccggcactgc cctcagactt caagaccatc ctggac    3396

<210> SEQ ID NO 17
<211> LENGTH: 4018
<212> TYPE: DNA
<213> ORGANISM: Homo sapiens

<400> SEQUENCE: 17
caggcagcgc tgcgtcctgc tgcgcacgtg ggaagccctg gccccggcca ccccgcgat     60 gccgcgcgct cccgctgcc gagccgtgcg ctccctgctg cgcagccact accgcgaggt    120
gctgccgctg ccacgttcg tgcggcgcct ggggcccag ggctggcggc tggtgcagcg    180
cggggacccg gcgctttcc gcgcgctggt ggccagtgtc ctggtgtgcg tgccctggga    240
cgcacggccg cccccgccg ccccctcctt ccgccaggtg tcctgcctga aggagctggt    300 ggccgagtg ctgcagaggc tgtgcgagcg cggcgcgaag aacgtgctgg ccttcggctt    360
cgcgctgctg acggggccc gcggggccc ccccgaggcc ttcaccacca gcgtgcgcag    420
ctacctgccc aacacggtga ccgacgcact gcggggagc ggggcgtggg ggctgctgct    480
gcgccgcgtg ggcgacgacg tgctggttca cctgctggca cgctgcgcgc tctttgtgct    540
ggtggctccc agctgcgcct accaggtgtg cgggccgccg ctgtaccagc tcggcgctgc    600
cactcaggcc cggcccccgc cacacgctag tggacccga aggcgtctgg gatgcgaacg    660
ggcctggaac catagcgtca gggaggccgg ggtcccctg ggcctgccag ccccgggtgc    720
gaggaggcgc gggggcagtg ccagccgaag tctgccgttg cccaagaggc ccaggcgtgg    780
cgctgcccct gagccggagc ggacgcccgt tgggcagggg tcctgggccc acccgggcag    840
```

```
gacgcgtgga ccgagtgacc gtggtttctg tgtggtgtca cctgccagac ccgccgaaga    900
agccacctct ttggagggtg cgctctctgg cacgcgccac tcccacccat ccgtgggccg    960
ccagcaccac gcgggccccc catccacatc gcggccacca cgtccctggg acacgccttg   1020
tcccccggtg tacgccgaga ccaagcactt cctctactcc tcaggcgaca aggagcagct   1080
gcggccctcc ttcctactca gctctctgag gcccagcctg actggcgctc ggaggctcgt   1140
ggagaccatc tttctggggtt ccaggccctg gatgccaggg actccccgca ggttgccccg   1200
cctgccccag cgctactggc aaatgcggcc cctgtttctg gagctgcttg gaaccacgc    1260 gcagtgcccc tacggggtgc tcctcaagac gcactgcccg ctgcgagctg cggtcacccc   1320
agcagccggt gtctgtgccc gggagaagcc ccagggctct gtggcggccc ccgaggagga   1380
ggacacagac ccccgtcgcc tggtgcagct gctccgccag cacagcagcc cctggcaggt   1440
gtacggcttc gtgcgggcct gcctgcgccg gctggtgccc ccaggcctct ggggctccag   1500
gcacaacgaa cgccgcttcc tcaggaacac caagaagttc atctccctgg ggaagcatgc   1560
caagctctcg ctgcaggagc tgacgtggaa gatgagcgtg cgggactgcg cttggctgcg   1620
caggagccca ggggttggct gtgttccggc cgcagagcac cgtctgcgtg aggagatcct   1680
ggccaagttc ctgcactggc tgatgagtgt gtacgtcgtc gagctgctca ggtctttctt   1740
ttatgtcacg gagaccacgt ttcaaaagaa caggctctttt ttctaccgga agagtgtctg   1800
gagcaagttg caaagcattg gaatcagaca gcacttgaag agggtgcagc tgcgggagct   1860
gtcggaagca gaggtcaggc agcatcggga agccaggccc gccctgctga cgtccagact   1920
ccgcttcatc cccaagcctg acgggctgcg gccgattgtg aacatggact acgtcgtggg   1980
agccagaacg ttccgcagag aaaagagggc cgagcgtctc acctcgaggg tgaaggcact   2040
gttcagcgtg ctcaactacg agcgggcgcg gcgccccggc ctcctgggcg cctctgtgct   2100
gggcctggac gatatccaca gggcctggcg caccttcgtg ctgcgtgtgc gggcccagga   2160
cccgccgcct gagctgtact ttgtcaaggt ggatgtgacg ggcgcgtacg acaccatccc   2220
ccaggacagg ctcacggagg tcatcgccag catcatcaaa ccccagaaca cgtactgcgt   2280
gcgtcggtat gccgtggtcc agaaggccgc ccatgggcac gtccgcaagg ccttcaagag   2340
ccacgtctct accttgacag acctccagcc gtacatgcga cagttcgtgg ctcacctgca   2400
ggagaccagc ccgctgaggg atgccgtcgt catcgagcag agctcctccc tgaatgaggc   2460
cagcagtggc ctcttcgacg tcttcctacg cttcatgtgc caccacgccg tgcgcatcag   2520
gggcaagtcc tacgtccagt gccagggggat cccgcagggc tccatcctct ccacgctgct   2580
ctgcagcctg tgctacggcg acatggagaa caagctgttt gcggggattc ggcgggacgg   2640
gctgctcctg cgtttggtgg atgatttctt gttggtgaca cctcacctca cccacgcgaa   2700
aaccttcctc aggaccctgg tccgaggtgt ccctgagtat ggctgcgtgg tgaacttgcg   2760
gaagacagtg gtgaacttcc ctgtagaaga cgaggccctg ggtggcacgg cttttgttca   2820
gatgccggcc cacggcctat tcccctggtg cggcctgctg ctggataccc ggaccctgga   2880
ggtgcagagc gactactcca gctatgcccg gacctccatc agagccagtc tcaccttcaa   2940
ccgcggcttc aaggctggga ggaacatgcg tcgcaaactc tttggggtct gcggctgaa    3000 gtgtcacagc ctgtttctgg atttgcaggt gaacagcctc cagacggtgt gcaccaacat   3060
ctacaagatc ctcctgctgc aggcgtacag gtttcacgca tgtgtgctgc agctcccatt   3120
tcatcagcaa gtttggaaga accccacatt tttcctgcgc gtcatctctg acacggcctc   3180
cctctgctac tccatcctga aagccaagaa cgcagggatg tcgctggggg ccaagggcgc   3240
```

-continued

```
cgccggccct ctgccctccg aggccgtgca gtggctgtgc caccaagcat tcctgctcaa    3300
gctgactcga caccgtgtca cctacgtgcc actcctgggg tcactcagga cagcccagac    3360
gcagctgagt cggaagctcc cggggacgac gctgactgcc ctggaggccg cagccaaccc    3420
ggcactgccc tcagacttca agaccatcct ggactgatgg ccacccgccc acagccaggc    3480
cgagagcaga caccagcagc cctgtcacgc cgggctctac gtcccaggga ggggggcg    3540 gcccacaccc aggcccgcac cgctgggagt ctgaggcctg agtgagtgtt tggccgaggc    3600
ctgcatgtcc ggctgaaggc tgagtgtccg gctgaggcct gagcgagtgt ccagccaagg    3660
gctgagtgtc cagcacacct gccgtcttca cttccccaca ggctggcgct cggctccacc    3720
ccagggccag cttttcctca ccaggagccc ggcttccact ccccacatag aatagtcca    3780 tccccagatt cgccattgtt caccccttgc cctgccctcc tttgccttcc accccacca    3840 tccaggtgga gaccctgaga aggaccctgg gagctctggg aatttggagt gaccaaaggt    3900
gtgccctgta cacaggcgag gaccctgcac ctggatgggg gtccctgtgg gtcaaattgg    3960
ggggaggtgc tgtgggagta aaatactgaa tatatgagtt tttcagtttt gaaaaaaa     4018
```

<210> SEQ ID NO 18
<211> LENGTH: 1132
<212> TYPE: PRT
<213> ORGANISM: Homo sapiens

<400> SEQUENCE: 18

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
                20                  25                  30

Pro Gln Gly Trp Arg Leu Val Gln Arg Gly Asp Pro Ala Ala Phe Arg
            35                  40                  45

Ala Leu Val Ala Gln Cys Leu Val Cys Val Pro Trp Asp Ala Arg Pro
        50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Arg Leu Arg Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240
```

```
Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655
```

-continued

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
            675                 680                 685

Ala Trp Arg Thr Phe Val Leu Arg Val Arg Ala Gln Asp Pro Pro Pro
            690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
            755                 760                 765

Leu Gln Pro Tyr Met Arg Gln Phe Val Ala His Leu Gln Glu Thr Ser
            770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
            805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
            835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
            885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
            915                 920                 925

Pro Trp Cys Gly Leu Leu Leu Asp Thr Arg Thr Leu Glu Val Gln Ser
930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
            965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
            995                 1000                1005

Ala Tyr Arg Phe His Ala Cys Val Leu Gln Leu Pro Phe His Gln
            1010                1015                1020

Gln Val Trp Lys Asn Pro Thr Phe Phe Leu Arg Val Ile Ser Asp
            1025                1030                1035

Thr Ala Ser Leu Cys Tyr Ser Ile Leu Lys Ala Lys Asn Ala Gly
            1040                1045                1050

Met Ser Leu Gly Ala Lys Gly Ala Ala Gly Pro Leu Pro Ser Glu
            1055                1060                1065

Ala Val Gln Trp Leu Cys His Gln Ala Phe Leu Leu Lys Leu Thr

```
              1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130

<210> SEQ ID NO 19
<211> LENGTH: 1132
<212> TYPE: PRT
<213> ORGANISM: Homo sapiens

<400> SEQUENCE: 19

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300
```

```
Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
```

```
                     725                 730                 735
Asn Thr Tyr Cys Val Arg Arg Tyr Ala Val Val Gln Lys Ala Ala His
                740                 745                 750
Gly His Val Arg Lys Ala Phe Lys Ser His Val Ser Thr Leu Thr Asp
                755                 760                 765
Leu Gln Pro Tyr Met Arg Gln Phe Val Ala His Leu Gln Glu Thr Ser
            770                 775                 780
Pro Leu Arg Asp Ala Val Val Ile Glu Gln Ser Ser Ser Leu Asn Glu
785                 790                 795                 800
Ala Ser Ser Gly Leu Phe Asp Val Phe Leu Arg Phe Met Cys His His
                805                 810                 815
Ala Val Arg Ile Arg Gly Lys Ser Tyr Val Gln Cys Gln Gly Ile Pro
                820                 825                 830
Gln Gly Ser Ile Leu Ser Thr Leu Leu Cys Ser Leu Cys Tyr Gly Asp
                835                 840                 845
Met Glu Asn Lys Leu Phe Ala Gly Ile Arg Arg Asp Gly Leu Leu Leu
            850                 855                 860
Arg Leu Val Asp Asp Phe Leu Leu Val Thr Pro His Leu Thr His Ala
865                 870                 875                 880
Lys Thr Phe Leu Arg Thr Leu Val Arg Gly Val Pro Glu Tyr Gly Cys
                885                 890                 895
Val Val Asn Leu Arg Lys Thr Val Val Asn Phe Pro Val Glu Asp Glu
            900                 905                 910
Ala Leu Gly Gly Thr Ala Phe Val Gln Met Pro Ala His Gly Leu Phe
            915                 920                 925
Pro Trp Cys Gly Leu Leu Leu Asp Thr Arg Thr Leu Glu Val Gln Ser
930                 935                 940
Asp Tyr Ser Ser Tyr Ala Arg Thr Ser Ile Arg Ala Ser Leu Thr Phe
945                 950                 955                 960
Asn Arg Gly Phe Lys Ala Gly Arg Asn Met Arg Arg Lys Leu Phe Gly
                965                 970                 975
Val Leu Arg Leu Lys Cys His Ser Leu Phe Leu Asp Leu Gln Val Asn
                980                 985                 990
Ser Leu Gln Thr Val Cys Thr Asn Ile Tyr Lys Ile Leu Leu Leu Gln
            995                 1000                1005
Ala Tyr Arg Phe His Ala Cys Val Leu Gln Leu Pro Phe His Gln
            1010                1015                1020
Gln Val Trp Lys Asn Pro Thr Phe Phe Leu Arg Val Ile Ser Asp
            1025                1030                1035
Thr Ala Ser Leu Cys Tyr Ser Ile Leu Lys Ala Lys Asn Ala Gly
            1040                1045                1050
Met Ser Leu Gly Ala Lys Gly Ala Ala Gly Pro Leu Pro Ser Glu
            1055                1060                1065
Ala Val Gln Trp Leu Cys His Gln Ala Phe Leu Leu Lys Leu Thr
            1070                1075                1080
Arg His Arg Val Thr Tyr Val Pro Leu Leu Gly Ser Leu Arg Thr
            1085                1090                1095
Ala Gln Thr Gln Leu Ser Arg Lys Leu Pro Gly Thr Thr Leu Thr
            1100                1105                1110
Ala Leu Glu Ala Ala Ala Asn Pro Ala Leu Pro Ser Asp Phe Lys
            1115                1120                1125
Thr Ile Leu Asp
            1130
```

<210> SEQ ID NO 20
<211> LENGTH: 2190
<212> TYPE: DNA
<213> ORGANISM: Homo sapiens

<400> SEQUENCE: 20

| | | | | | |
|---|---|---|---|---|---|
| atgcagctgt | ttgagcagcc | ctgtcctggg | gaggaccccc | ggccaggagg | ccagatcggt | 60 |
| gaggtggagc | tgtcctccta | cacgccccca | gccgggtcc | caggaaagcc | tgcagccccc | 120 |
| cacttccttc | cagtgctgtg | ctctgtgtca | ccatcaggct | ccagggtccc | gcacgacctc | 180 |
| ctcgggggct | ccgggggctt | cacgctggag | gacgccctct | tcgggctcct | ctttggagct | 240 |
| gatgccaccc | tcctgcagtc | acctgtggtc | ctctgtggtc | tccctgatgg | ccagctctgc | 300 |
| tgtgtgatcc | tgaaggccct | ggtcacctcc | aggtcagccc | ctggtgaccc | aaatgccctt | 360 |
| gtcaagatcc | tccatcacct | ggaggagccc | gtcatcttca | tagggccctt | gaagacagag | 420 |
| ccacaggctg | cagaagctgc | agagaatttt | ctgcctgacg | aggatgtgca | ctgtgactgc | 480 |
| ctggtggcct | ttggtcacca | cggccggatg | ctggccatca | aggccagctg | ggatgagtcc | 540 |
| gggaagctgg | tgcccgagct | gcgggagtac | tgcctcccag | gcctgtgct | ctgcgctgcc | 600 |
| tgtggcgggg | gtggccgcgt | gtaccacagc | accccttctg | acctctgtgt | ggtggatctg | 660 |
| tctcggggaa | gcaccccgct | gggccctgag | cagcccgaag | aaggcccggg | aggcctgccc | 720 |
| cccatgctgt | gcccagccag | cctgaacatc | tgcagtgtcg | tctcgctgtc | cgcgtctccc | 780 |
| aggacgcatg | aagtggcac | caagctcctg | gccctgtccg | ccaaaggccg | cctgatgacc | 840 |
| tgcagcctgg | acctggactc | tgagatgcct | ggcccagcca | ggatgaccac | agagagtgca | 900 |
| ggtcagaaaa | taaggagct | gctgtctgga | attggcaaca | tctctgagag | agtgtctttt | 960 |
| ctaaagaagg | cggttgacca | gcggaacaag | gcactgacaa | gcctcaacga | ggccatgaac | 1020 |
| gtgagctgtg | cactgctgtc | aagcggcacg | ggccccagac | ccatctcctg | caccaccagc | 1080 |
| accacctgga | gccgcctgca | gacacaggat | gtgctcatgg | ccacctgcgt | gctagagaac | 1140 |
| agcagcagct | tcagcctgga | ccaggggtgg | accctgtgca | tccaggtgct | caccagctcc | 1200 |
| tgtgctctcg | acctggactc | ggcctgctcc | gccatcacct | acaccatccc | cgtggaccag | 1260 |
| ctcggcccg | gtgctcggcg | ggaggtgacg | ctacccctgg | gccctggtga | aacggcggg | 1320 |
| ctcgacctgc | ccgtgaccgt | gtcctgcacg | ctgttctaca | gtctcaggga | ggtggtgggc | 1380 |
| ggggcccttg | cccccttaga | ctctgaggac | ccctttctgg | atgagtgccc | ctccgacgtc | 1440 |
| ctgcccgagc | aagagggtgt | tgcctgccc | ctgagcaggc | acacagtgga | catgctgcag | 1500 |
| tgtctgcgct | tccctggcct | ggccccgcca | cacacacggg | cccctcccc | actcggcccc | 1560 |
| acccgagacc | ctgtggccac | ttttctggaa | acttgtcggg | agcctggcag | ccagccagca | 1620 |
| ggacccgcct | ccctgcgggc | cgagtacctg | cccccatctg | tggcttccat | caaggtgtcg | 1680 |
| gcggagctgc | tcagagctgc | cttgaaggac | ggccactcag | gcgtgcccct | gtgctgtgcc | 1740 |
| accctgcagt | ggctccttgc | tgagaatgct | gctgtggacg | tcgtgagggc | ccgagcacta | 1800 |
| tcttccatcc | agggagtggc | ccctgatggc | ccaacgttc | acctcatcgt | ccgagaggtg | 1860 |
| gccatgaccg | acctgtgccc | agcagggccc | atccaggccc | tggagattca | agtggaaagc | 1920 |
| tcctctctgg | ccgacatttg | caggcgcac | catgccgttg | tcgggcgcat | gcagacgatg | 1980 |
| gtgacagagc | aggccgccca | gggctccagc | gctcctgatc | tccgtgtgca | gtacctccgc | 2040 |
| cagatccacg | ccaaccacga | gacactgctg | cgggaggtgc | agaccctgcg | cgaccggctc | 2100 |

```
tgcacggagg atgaggccag ctcctgtgcc accgcccaga ggctgctaca ggtgtaccgg    2160
cagctgcgcc accccagcct catcctgctg                                     2190
```

<210> SEQ ID NO 21
<211> LENGTH: 2190
<212> TYPE: DNA
<213> ORGANISM: Homo sapiens

<400> SEQUENCE: 21

```
atgcagctgt ttgagcagcc ctgtcctggg gaggacccc ggccaggagg ccagatcggt      60
gaggtggagc tgtcctccta cacgccccca gccggggtcc caggaaagcc tgcagccccc    120
cacttccttc cagtgctgtg ctctgtgtca ccatcaggct ccagggtccc gcacgacctc    180
ctcgggggct ccgggggctt cacgctggag acgccctct tcgggctcct ctttggagct    240
gatgccaccc tcctgcagtc acctgtggtc ctctgtggtc tccctgatgg ccagctctgc    300
tgtgtgatcc tgaaggccct ggtcacctcc aggtcagccc tggtgaccc aaatgccctt     360 gtcaagatcc tccatcacct ggaggagccc gtcatcttca taggggcctt gaagacagag    420
ccacaggctg cagaagctgc agagaatttt ctgcctgacg aggatgtgca ctgtgactgc    480
ctggtggcct ttggtcacca cggccggatg ctggccatca aggccagctg ggatgagtcc    540
gggaagctgg tgcccgagct gcgggagtac tgcctcccag ccctgtgct ctgcgctgcc     600 tgtggcgggg tggccgcgt gtaccacagc accccttctg acctctgtgt ggtggatctg    660
tctcggggaa gcaccccgct gggccctgag cagcccgaag aaggcccggg aggcctgccc    720
cccatgctgt gccagccag cctgaacatc tgcagtgtcg tctcgctgtc cgcgtctccc    780
aggacgcatg aaggtggcac caagctcctg gccctgtccg ccaaaggccg cctgatgacc    840
tgcagcctgg acctggactc tgagatgcct ggcccagcca ggatgaccac agagagtgca    900
ggtcagaaaa taaaggagct gctgtctgga attggcaaca tctctgagag agtgtctttt    960
ctaaagaagg cggttgacca gcggaacaag gcactgacaa gcctcaacga ggccatgaac   1020
gtgagctgtg cactgctgtc aagcggcacg ggcccagac ccatctcctg caccaccagc    1080
accacctgga gccgcctgca gacacaggat gtgctcatgg ccacctgcgt gctagagaac   1140
agcagcagct tcagcctgga ccaggggtgg accctgtgca tccaggtgct caccagctcc   1200
tgtgctctcg acctggactc ggcctgctcc gccatcacct acaccatccc cgtgaccag    1260 ctcggccccg tgctcggcg ggaggtgacg ctaccctgg gccctggtga aacggcggg      1320 ctcgacctgc ccgtgaccgt gtcctgcacg ctgttctaca gtctcaggga ggtggtgggc   1380
ggggcccttg ccccctcaga ctctgaggac ccctttctgg atgagtgccc ctccgacgtc   1440
ctgcccgagc aagagggtgt ttgcctgccc ctgagcaggc acacagtgga catgctgcag   1500
tgtctgcgct tccctggcct ggccccgcca cacacacggg cccctccc actcggcccc    1560 acccgagacc ctgtgccac ttttctggaa acttgtcggg agcctggcag ccagccagca    1620 ggaccccgcct ccctgcgggc cgagtacctg ccccatctg tggcttccat caaggtgtcg   1680
gcggagctgc tcagagctgc cttgaaggac ggccactcag gcgtgccct gtgctgtgcc    1740 accctgcagt ggctccttgc tgagaatgct gctgtggacg tcgtgagggc ccgagcacta   1800
tcttccatcc agggagtggc ccctgatggc gccaacgttc acctcatcgt ccgagaggtg   1860
gccatgaccg acctgtgccc agcagggccc atccaggccg tggagattca agtggaaagc   1920
tcctctctgg ccgacatttg cagggcgcac catgccgttg tcgggcgcat gcagacgatg   1980
gtgacagagc aggccgccca gggctccagc gctcctgatc tccgtgtgca gtacctccgc   2040
```

-continued

| | |
|---|---|
| cagatccacg ccaaccacga gacactgctg cgggaggtgc agaccctgcg cgaccggctc | 2100 |
| tgcacggagg atgaggccag ctcctgtgcc accgcccaga ggctgctaca ggtgtaccgg | 2160 |
| cagctgcgcc accccagcct catcctgctg | 2190 |

<210> SEQ ID NO 22
<211> LENGTH: 3163
<212> TYPE: DNA
<213> ORGANISM: Homo sapiens

<400> SEQUENCE: 22

| | |
|---|---|
| ggacagtgtg ctggtcaccc tggtgcaggg ccctgcccga tggaagatgc agctgtttga | 60 |
| gcagccctgt cctggggagg accccggcc aggaggccag atcggtgagg tggagctgtc | 120 |
| ctcctacacg cccccagccg ggtcccagg aaagcctgca gccccccact tccttccagt | 180 |
| gctgtgctct gtgtcaccat caggctccag ggtcccgcac gacctcctcg ggggctccgg | 240 |
| gggcttcacg ctggaggacg ccctcttcgg gctcctcttt ggagctgatg ccaccctcct | 300 |
| gcagtcacct gtggtcctct gtggtctccc tgatggccag ctctgctgtg tgatcctgaa | 360 |
| ggccctggtc acctccaggt cagccctgg tgacccaaat gcccttgtca agatcctcca | 420 |
| tcacctggag gagcccgtca tcttcatagg ggccttgaag acagagccac aggctgcaga | 480 |
| agctgcagaa aattttctgc ctgacgagga tgtgcactgt gactgcctgg tggcctttgg | 540 |
| tcaccacggc cggatgctgg ccatcaaggc cagctgggat gagtccggga gctggtgcc | 600 |
| cgagctgcgg gagtactgcc tcccaggccc tgtgctctgc gctgcctgtg gcggggtgg | 660 |
| ccgcgtgtac cacagcaccc cttctgacct ctgtgtggtg gatctgtctc ggggaagcac | 720 |
| cccgctgggc cctgagcagc ccgaagaagg cccgggaggc ctgcccccca tgctgtgccc | 780 |
| agccagcctg aacatctgca gtgtcgtctc gctgtccgcg tctcccagga cgcatgaagg | 840 |
| tggcaccaag ctcctggccc tgtccgccaa aggccgcctg atgacctgca gcctggacct | 900 |
| ggactctgag atgcctggcc cagccaggat gaccacagag agtgcaggtc agaaaataaa | 960 |
| ggagctgctg tctggaattg gcaacatctc tgagagagtg tcttttctaa agaaggcggt | 1020 |
| tgaccagcgg aacaaggcac tgacaagcct caacgaggcc atgaacgtga gctgtgcact | 1080 |
| gctgtcaagc ggcacgggcc ccagacccat ctcctgcacc accagcacca cctggagccg | 1140 |
| cctgcagaca caggatgtgc tcatggccac ctgcgtgcta gagaacagca gcagcttcag | 1200 |
| cctggaccag gggtggaccc tgtgcatcca ggtgctcacc agctcctgtg ctctcgacct | 1260 |
| ggactcggcc tgctccgcca tcacctacac catccccgtg gaccagctcg gccccggtgc | 1320 |
| tcggcgggag gtgacgctac ccctgggccc tggtgagaac ggcgggctcg acctgcccgt | 1380 |
| gaccgtgtcc tgcacgctgt tctacagtct caggaggtg gtgggcgggg cccttgcccc | 1440 |
| ctcagactct gaggacccct ttctggatga gtgccctcc gacgtcctgc ccgagcaaga | 1500 |
| gggtgtttgc ctgcccctga gcaggcacac agtggacatg ctgcagtgtc tgcgcttccc | 1560 |
| tggcctggcc ccgccacaca cacgggcccc ctccccactc ggccccaccc gagaccctgt | 1620 |
| ggccactttt ctggaaaactt gtcgggagcc tggcagccag ccagcaggac ccgcctccct | 1680 |
| gcgggccgag tacctgcccc catctgtggc ttcatcaag gtgtcggcgg agctgctcag | 1740 |
| agctgccttg aaggacggcc actcaggcgt gccctgtgc tgtgccaccc tgcagtggct | 1800 |
| ccttgctgag aatgctgctg tggacgtcgt gagggcccga gcactatctt ccatccaggg | 1860 |
| agtggcccct gatggcgcca acgttcacct catcgtccga gaggtggcca tgaccgacct | 1920 |

```
gtgcccagca gggcccatcc aggccgtgga gattcaagtg gaaagctcct ctctggccga    1980
catttgcagg gcgcaccatg ccgttgtcgg gcgcatgcag acgatggtga cagagcaggc    2040
cgcccagggc tccagcgctc ctgatctccg tgtgcagtac ctccgccaga tccacgccaa    2100
ccacgagaca ctgctgcggg aggtgcagac cctgcgcgac cggctctgca cggaggatga    2160
ggccagctcc tgtgccaccg cccagaggct gctacaggtg taccggcagc tgcgccaccc    2220
cagcctcatc ctgctgtgac caggcgggcc tgccccaggg ctctggccac gcttccagcc    2280
tctgtcacag ccccccagg cctcatgggt tagagggaaa ccgagctggc ctggccagag    2340
ccgtcaggga aggtaggacc tggccacgta ggagcagaac gctcatgaaa gtgcttggag    2400
gccgtggagc acaaagcaga ttctgattgg gagcaaccga ggcgggctct gaacctggcc    2460
ggtccagctt cgcgtcctct gctggtgtct ctccttctct gaccgcggcc gcagcccctg    2520
cactcgcctt cctcactgct gggcagcctt cccaccaccg cagcagcccc tgaggccagg    2580
aggcagtgca gggcattctg gacccggagg gccagagaaa caggatttct ggggtttgga    2640
cttggggtga gtttgtaact gttgctgcca caccaccagg agcaccggct gcccctctgg    2700
gtggcactac caggtgcccc acggtaccct tgtcacactg ttcacacctg cccggctgcc    2760
cactctggga ccccgaggta ggagggtgct ccctgagacc aaagcacaaa acagcatgca    2820
gggagctcct gcaagtgccc gtggtctcgt gccacaccaa ggaagggcca gcgggtggcc    2880
tgtggccgga atgctcaaca actaggtgcc tccggccggg gcagtaccca gcactgtgca    2940
ctattttcag ggccactcag ggtggcgctg tggcccgggg gggggccctg agccccagcc    3000
cccagcctcc tccctcagcc tgggctacgg cccacctcct ggtgctggtg ttttcatctg    3060
gggagggtgc tcgcgccgct cccgctgcag gcactgtccg cgatgagtgc gggtaggagc    3120
cgtgaggtgc ttctctgctg tgacaaacga ccctgtctgt ccg                     3163
```

<210> SEQ ID NO 23
<211> LENGTH: 730
<212> TYPE: PRT
<213> ORGANISM: Homo sapiens

<400> SEQUENCE: 23

Met Gln Leu Phe Glu Gln Pro Cys Pro Gly Glu Asp Pro Arg Pro Gly
1               5                   10                  15

Gly Gln Ile Gly Glu Val Glu Leu Ser Ser Tyr Thr Pro Pro Ala Gly
            20                  25                  30

Val Pro Gly Lys Pro Ala Ala Pro His Phe Leu Pro Val Leu Cys Ser
        35                  40                  45

Val Ser Pro Ser Gly Ser Arg Val Pro His Asp Leu Leu Gly Gly Ser
    50                  55                  60

Gly Gly Phe Thr Leu Glu Asp Ala Leu Phe Leu Leu Phe Gly Ala
65                  70                  75                  80

Asp Ala Thr Leu Leu Gln Ser Pro Val Val Leu Cys Gly Leu Pro Asp
                85                  90                  95

Gly Gln Leu Cys Cys Val Ile Leu Lys Ala Leu Val Thr Ser Arg Ser
            100                 105                 110

Ala Pro Gly Asp Pro Asn Ala Leu Val Lys Ile Leu His His Leu Glu
        115                 120                 125

Glu Pro Val Ile Phe Ile Gly Ala Leu Lys Thr Glu Pro Gln Ala Ala
    130                 135                 140

Glu Ala Ala Glu Asn Phe Leu Pro Asp Glu Asp Val His Cys Asp Cys
145                 150                 155                 160

-continued

```
Leu Val Ala Phe Gly His His Gly Arg Met Leu Ala Ile Lys Ala Ser
            165                 170                 175

Trp Asp Glu Ser Gly Lys Leu Val Pro Glu Leu Arg Glu Tyr Cys Leu
            180                 185                 190

Pro Gly Pro Val Leu Cys Ala Ala Cys Gly Gly Gly Arg Val Tyr
            195                 200                 205

His Ser Thr Pro Ser Asp Leu Cys Val Val Asp Leu Ser Arg Gly Ser
            210                 215                 220

Thr Pro Leu Gly Pro Glu Gln Pro Glu Glu Gly Pro Gly Leu Pro
225                 230                 235                 240

Pro Met Leu Cys Pro Ala Ser Leu Asn Ile Cys Ser Val Val Ser Leu
            245                 250                 255

Ser Ala Ser Pro Arg Thr His Glu Gly Gly Thr Lys Leu Leu Ala Leu
            260                 265                 270

Ser Ala Lys Gly Arg Leu Met Thr Cys Ser Leu Asp Leu Asp Ser Glu
            275                 280                 285

Met Pro Gly Pro Ala Arg Met Thr Thr Glu Ser Ala Gly Gln Lys Ile
            290                 295                 300

Lys Glu Leu Leu Ser Gly Ile Gly Asn Ile Ser Glu Arg Val Ser Phe
305                 310                 315                 320

Leu Lys Lys Ala Val Asp Gln Arg Asn Lys Ala Leu Thr Ser Leu Asn
            325                 330                 335

Glu Ala Met Asn Val Ser Cys Ala Leu Leu Ser Ser Gly Thr Gly Pro
            340                 345                 350

Arg Pro Ile Ser Cys Thr Thr Ser Thr Thr Trp Ser Arg Leu Gln Thr
            355                 360                 365

Gln Asp Val Leu Met Ala Thr Cys Val Leu Glu Asn Ser Ser Ser Phe
            370                 375                 380

Ser Leu Asp Gln Gly Trp Thr Leu Cys Ile Gln Val Leu Thr Ser Ser
385                 390                 395                 400

Cys Ala Leu Asp Leu Asp Ser Ala Cys Ser Ala Ile Thr Tyr Thr Ile
            405                 410                 415

Pro Val Asp Gln Leu Gly Pro Gly Ala Arg Arg Glu Val Thr Leu Pro
            420                 425                 430

Leu Gly Pro Gly Glu Asn Gly Gly Leu Asp Leu Pro Val Thr Val Ser
            435                 440                 445

Cys Thr Leu Phe Tyr Ser Leu Arg Glu Val Val Gly Ala Leu Ala
            450                 455                 460

Pro Leu Asp Ser Glu Asp Pro Phe Leu Asp Glu Cys Pro Ser Asp Val
465                 470                 475                 480

Leu Pro Glu Gln Glu Gly Val Cys Leu Pro Leu Ser Arg His Thr Val
            485                 490                 495

Asp Met Leu Gln Cys Leu Arg Phe Pro Gly Leu Ala Pro His Thr
            500                 505                 510

Arg Ala Pro Ser Pro Leu Gly Pro Thr Arg Asp Pro Val Ala Thr Phe
            515                 520                 525

Leu Glu Thr Cys Arg Glu Pro Gly Ser Gln Pro Ala Gly Pro Ala Ser
            530                 535                 540

Leu Arg Ala Glu Tyr Leu Pro Pro Ser Val Ala Ser Ile Lys Val Ser
545                 550                 555                 560

Ala Glu Leu Leu Arg Ala Ala Leu Lys Asp Gly His Ser Gly Val Pro
            565                 570                 575
```

```
Leu Cys Cys Ala Thr Leu Gln Trp Leu Leu Ala Glu Asn Ala Ala Val
            580                 585                 590

Asp Val Val Arg Ala Arg Ala Leu Ser Ser Ile Gln Gly Val Ala Pro
            595                 600                 605

Asp Gly Ala Asn Val His Leu Ile Val Arg Glu Val Ala Met Thr Asp
            610                 615                 620

Leu Cys Pro Ala Gly Pro Ile Gln Ala Val Glu Ile Gln Val Glu Ser
625                 630                 635                 640

Ser Ser Leu Ala Asp Ile Cys Arg Ala His His Ala Val Val Gly Arg
                645                 650                 655

Met Gln Thr Met Val Thr Glu Gln Ala Ala Gln Gly Ser Ser Ala Pro
            660                 665                 670

Asp Leu Arg Val Gln Tyr Leu Arg Gln Ile His Ala Asn His Glu Thr
            675                 680                 685

Leu Leu Arg Glu Val Gln Thr Leu Arg Asp Arg Leu Cys Thr Glu Asp
            690                 695                 700

Glu Ala Ser Ser Cys Ala Thr Ala Gln Arg Leu Leu Gly Val Tyr Arg
705                 710                 715                 720

Gln Leu Arg His Pro Ser Leu Ile Leu Leu
                725                 730

<210> SEQ ID NO 24
<211> LENGTH: 730
<212> TYPE: PRT
<213> ORGANISM: Homo sapiens

<400> SEQUENCE: 24

Met Gln Leu Phe Glu Gln Pro Cys Pro Gly Glu Asp Pro Arg Pro Gly
1               5                   10                  15

Gly Gln Ile Gly Glu Val Glu Leu Ser Ser Tyr Thr Pro Pro Ala Gly
            20                  25                  30

Val Pro Gly Lys Pro Ala Ala Pro His Phe Leu Pro Val Leu Cys Ser
        35                  40                  45

Val Ser Pro Ser Gly Ser Arg Val Pro His Asp Leu Leu Gly Gly Ser
    50                  55                  60

Gly Gly Phe Thr Leu Glu Asp Ala Leu Phe Gly Leu Leu Phe Gly Ala
65                  70                  75                  80

Asp Ala Thr Leu Leu Gln Ser Pro Val Val Leu Cys Gly Leu Pro Asp
                85                  90                  95

Gly Gln Leu Cys Cys Val Ile Leu Lys Ala Leu Val Thr Ser Arg Ser
            100                 105                 110

Ala Pro Gly Asp Pro Asn Ala Leu Val Lys Ile Leu His His Leu Glu
        115                 120                 125

Glu Pro Val Ile Phe Ile Gly Ala Leu Lys Thr Glu Pro Gln Ala Ala
    130                 135                 140

Glu Ala Ala Glu Asn Phe Leu Pro Asp Glu Asp Val His Cys Asp Cys
145                 150                 155                 160

Leu Val Ala Phe Gly His His Gly Arg Met Leu Ala Ile Lys Ala Ser
                165                 170                 175

Trp Asp Glu Ser Gly Lys Leu Val Pro Glu Leu Arg Glu Tyr Cys Leu
            180                 185                 190

Pro Gly Pro Val Leu Cys Ala Ala Cys Gly Gly Gly Arg Val Tyr
        195                 200                 205

His Ser Thr Pro Ser Asp Leu Cys Val Val Asp Leu Ser Arg Gly Ser
    210                 215                 220
```

-continued

```
Thr Pro Leu Gly Pro Glu Gln Pro Glu Glu Gly Pro Gly Gly Leu Pro
225                 230                 235                 240

Pro Met Leu Cys Pro Ala Ser Leu Asn Ile Cys Ser Val Val Ser Leu
            245                 250                 255

Ser Ala Ser Pro Arg Thr His Glu Gly Gly Thr Lys Leu Leu Ala Leu
        260                 265                 270

Ser Ala Lys Gly Arg Leu Met Thr Cys Ser Leu Asp Leu Asp Ser Glu
    275                 280                 285

Met Pro Gly Pro Ala Arg Met Thr Thr Glu Ser Ala Gly Gln Lys Ile
290                 295                 300

Lys Glu Leu Leu Ser Gly Ile Gly Asn Ile Ser Glu Arg Val Ser Phe
305                 310                 315                 320

Leu Lys Lys Ala Val Asp Gln Arg Asn Lys Ala Leu Thr Ser Leu Asn
            325                 330                 335

Glu Ala Met Asn Val Ser Cys Ala Leu Leu Ser Ser Gly Thr Gly Pro
        340                 345                 350

Arg Pro Ile Ser Cys Thr Thr Ser Thr Thr Trp Ser Arg Leu Gln Thr
    355                 360                 365

Gln Asp Val Leu Met Ala Thr Cys Val Leu Glu Asn Ser Ser Ser Phe
370                 375                 380

Ser Leu Asp Gln Gly Trp Thr Leu Cys Ile Gln Val Leu Thr Ser Ser
385                 390                 395                 400

Cys Ala Leu Asp Leu Asp Ser Ala Cys Ser Ala Ile Thr Tyr Thr Ile
            405                 410                 415

Pro Val Asp Gln Leu Gly Pro Gly Ala Arg Arg Glu Val Thr Leu Pro
        420                 425                 430

Leu Gly Pro Gly Glu Asn Gly Gly Leu Asp Leu Pro Val Thr Val Ser
    435                 440                 445

Cys Thr Leu Phe Tyr Ser Leu Arg Glu Val Val Gly Gly Ala Leu Ala
450                 455                 460

Pro Ser Asp Ser Glu Asp Pro Phe Leu Asp Glu Cys Pro Ser Asp Val
465                 470                 475                 480

Leu Pro Glu Gln Glu Gly Val Cys Leu Pro Leu Ser Arg His Thr Val
            485                 490                 495

Asp Met Leu Gln Cys Leu Arg Phe Pro Gly Leu Ala Pro Pro His Thr
        500                 505                 510

Arg Ala Pro Ser Pro Leu Gly Pro Thr Arg Asp Pro Val Ala Thr Phe
    515                 520                 525

Leu Glu Thr Cys Arg Glu Pro Gly Ser Gln Pro Ala Gly Pro Ala Ser
530                 535                 540

Leu Arg Ala Glu Tyr Leu Pro Pro Ser Val Ala Ser Ile Lys Val Ser
545                 550                 555                 560

Ala Glu Leu Leu Arg Ala Ala Leu Lys Asp Gly His Ser Gly Val Pro
            565                 570                 575

Leu Cys Cys Ala Thr Leu Gln Trp Leu Leu Ala Glu Asn Ala Ala Val
        580                 585                 590

Asp Val Val Arg Ala Arg Ala Leu Ser Ser Ile Gln Gly Val Ala Pro
    595                 600                 605

Asp Gly Ala Asn Val His Leu Ile Val Arg Glu Val Ala Met Thr Asp
610                 615                 620

Leu Cys Pro Ala Gly Pro Ile Gln Ala Val Glu Ile Gln Val Glu Ser
625                 630                 635                 640
```

-continued

```
Ser Ser Leu Ala Asp Ile Cys Arg Ala His His Ala Val Val Gly Arg
            645                 650                 655

Met Gln Thr Met Val Thr Glu Gln Ala Ala Gln Gly Ser Ser Ala Pro
            660                 665                 670

Asp Leu Arg Val Gln Tyr Leu Arg Gln Ile His Ala Asn His Glu Thr
            675                 680                 685

Leu Leu Arg Glu Val Gln Thr Leu Arg Asp Arg Leu Cys Thr Glu Asp
            690                 695                 700

Glu Ala Ser Ser Cys Ala Thr Ala Gln Arg Leu Leu Gln Val Tyr Arg
705             710                 715                 720

Gln Leu Arg His Pro Ser Leu Ile Leu Leu
                725                 730
```